US011624074B2

(12) United States Patent
Lippman et al.

(10) Patent No.: US 11,624,074 B2
(45) Date of Patent: Apr. 11, 2023

(54) MUTATIONS IN SOLANACEAE PLANTS THAT MODULATE SHOOT ARCHITECTURE AND ENHANCE YIELD-RELATED PHENOTYPES

(71) Applicant: Cold Spring Harbor Laboratory, Cold Spring Harbor, NY (US)

(72) Inventors: Zachary Lippman, North Bellmore, NY (US); Soon-Ju Park, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 423 days.

(21) Appl. No.: 14/443,357

(22) PCT Filed: Nov. 19, 2013

(86) PCT No.: PCT/US2013/070825
§ 371 (c)(1),
(2) Date: May 15, 2015

(87) PCT Pub. No.: WO2014/081730
PCT Pub. Date: May 30, 2014

(65) Prior Publication Data

US 2015/0284732 A1 Oct. 8, 2015

Related U.S. Application Data

(63) Continuation-in-part of application No. 13/799,831, filed on Mar. 13, 2013, now Pat. No. 9,732,352.

(60) Provisional application No. 61/869,052, filed on Aug. 22, 2013, provisional application No. 61/728,654, filed on Nov. 20, 2012.

(51) Int. Cl.

| | |
|---|---|
| ***C12N 15/82*** | (2006.01) |
| ***A01H 5/08*** | (2018.01) |
| ***C07K 14/415*** | (2006.01) |
| ***A01H 6/82*** | (2018.01) |
| ***A01H 1/02*** | (2006.01) |

(52) U.S. Cl.
CPC ............. *C12N 15/827* (2013.01); *A01H 1/02* (2013.01); *A01H 5/08* (2013.01); *A01H 6/825* (2018.05); *C07K 14/415* (2013.01); *C12N 15/8261* (2013.01)

(58) Field of Classification Search
None
See application file for complete search history.

(56) References Cited

U.S. PATENT DOCUMENTS

| | | | | |
|---|---|---|---|---|
| 8,865,970 | B2 | 10/2014 | Zamir et al. | |
| 9,414,553 | B2 | 8/2016 | de Haan et al. | |
| 9,732,352 | B2 | 8/2017 | Lippman et al. | |
| 2010/0212046 | A1 | 8/2010 | Heidens | |
| 2011/0247093 | A1* | 10/2011 | Zamir ...................... | A01H 1/02 800/260 |
| 2012/0144514 | A1 | 6/2012 | de Haan et al. | |
| 2014/0143898 | A1 | 5/2014 | Lippman et al. | |
| 2015/0011393 | A1 | 1/2015 | Tsuji et al. | |
| 2020/0299705 | A1 | 9/2020 | Lippman et al. | |

FOREIGN PATENT DOCUMENTS

| | | | |
|---|---|---|---|
| EP | 2647646 | A1 | 10/2013 |
| EP | 13857579.0 | | 5/2016 |
| EP | 13857579.0 | | 6/2017 |
| WO | WO 2010/041190 | A1 | 4/2010 |
| WO | PCT/US2013/070825 | | 2/2014 |
| WO | WO 2014/081730 | A1 | 5/2014 |
| WO | PCT/US2013/070825 | | 6/2015 |
| WO | WO 2017/180474 | A1 | 10/2017 |

OTHER PUBLICATIONS

Pnueli et al. Development 125.11 (1998): 1979-1989.*
Quinet et al. (International Journal of Plant Developmental Biology 1.1 (2007): 64-74). (Year: 2007).*
Pnueli et al. (Development 125, 1979-1989,1998). (Year: 1998).*
GenBank Accesssion AY186735, dated Jan. 22, 2004. (Year: 2004).*
Krieger et al. (Nature genetics 42.5 (2010): 459-463) Supplemental figures and tables. (Year: 2010).*
GenBank Accession AY186735 (dated Jan. 22, 2004). (Year: 2004).*
Pnueli, et al. (Development 125.11 (1998): 1979-1989). (Year: 1998).*
Ahn et al. (The EMBO journal 25.3 (2006): 605-614). (Year: 2006).*
Krieger et al. (Nature genetics 42.5 (2010): 459-463) (Year: 2010).*
International Preliminary Report on Patentability dated Jun. 6, 2015 for application No. PCT/US2013/070825.
International Search Report and Written Opinion dated Feb. 24, 2014 for application No. PCT/US2013/070825.
Aoki et al., Large-scale analysis of full-length cDNAs from the tomato (*Solanum lycopersicum*) cultivar Micro-Tom, a reference system for the Solanaceae genomics. BMC Genomics. Mar. 30, 2010;11:210. doi: 10.1186/1471-2164-11-210.
Genbank Submission; NIH/NCBI, Accession No. NP_0012345345. Lifschitz et al., Nov. 30, 2014. 1 page.
Krieger et al., The flowering gene Single Flower Truss drives heterosis for yield in tomato. Nat Genet. May 2010;42(5):459-63. doi:10.1038/ng.550. Epub Mar. 28, 2010.
Lee et al., Homologous recombination in plant cells after Agrobacterium-mediated transformation. Plant Cell. May 1990;2(5):415-25.
Lifschitz et al., The tomato FT ortholog triggers systemic signals that regulate growth and flowering and substitute for diverse environmental stimuli. Proc Natl Acad Sci U S A. Apr. 18, 2006;103(16):6398-403. Epub Apr. 10, 2006.
McCormick, Transformation of tomato with Agrobacterium tumefaciens. In: Plant Tissue Culture Manual, Fundamentals and Applications. 1991, Lindsey, Ed. Volume B6:1-9.

(Continued)

*Primary Examiner* — Charles Logsdon
(74) *Attorney, Agent, or Firm* — Wolf, Greenfield & Sacks, P.C.

(57) ABSTRACT

Provided herein are genetically-altered Solanaceae plants, compositions related to the Solanaceae plants, and methods of making the Solanaceae plants.

17 Claims, 13 Drawing Sheets

Specification includes a Sequence Listing.

(56) References Cited

OTHER PUBLICATIONS

Molinero-Rosales et al., Single Flower Truss regulates the transition and maintenance of flowering in tomato. Planta. Jan. 2004;218(3):427-34. Epub Sep. 23, 2003.
Park et al., Optimization of crop productivity in tomato using induced mutations in the florigen pathway. Nat Genet. Dec. 2014;46(12):1337-42. doi: 10.1038/ng.3131. Epub Nov. 2, 2014.
Pnueli et al., Tomato SP-interacting proteins define a conserved signaling system that regulates shoot architecture and flowering. Plant Cell. Dec. 2001;13(12):2687-702.
Taoka et al., 14-3-3 proteins act as intracellular receptors for rice Hd3a florigen. Nature. Jul. 31, 2011;476(7360):332-5. doi: 10.1038/nature10272.
Wigge et al., Integration of spatial and temporal information during floral induction in Arabidopsis. Science. Aug. 12, 2005;309(5737):1056-9.
Wigge et al., Supplement: integration of spatial and temporal information during floral induction in Arabidopsis. Science. Aug. 12, 2005;309(5737):S1-S8.
Extended European Search Report for Application No. EP13857579.0 dated May 30, 2016.
European Office Action for Application No. EP13857579.0 dated Jun. 7, 2017.
Abe et al., FD, a bZIP protein mediating signals from the floral pathway integrator FT at the shoot apex. Science. Aug. 12, 2005;309(5737):1052-6.
Ahn et al., A divergent external loop confers antagonistic activity on floral regulators FT and TFL1. EMBO J. Feb. 8, 2006;25(3):605-14. Epub Jan. 19, 2006.
International Search Report and Written Opinion for Application No. PCT/US2017/026635 dated Jul. 11, 2017.
International Preliminary Report on Patentability for Application No. PCT/US2017/026635 dated Oct. 25, 2018.
Extended European Search Report for Application No. EP 17782888 dated Oct. 25, 2019.
Cao et al., Four Tomato Flowering Locus T-Like Proteins Act Antagonistically to Regulate Floral Initiation. Front Plant Sci. Jan. 11, 2016;6:1213. doi: 10.3389/fpls.2015.01213.eCollection 2015.
Carmel-Goren et al., The SELF-PRUNING gene family in tomato. Plant Mol Biol. Aug. 2003;52(6):1215-22.
Jiang et al., Tomato yield heterosis is triggered by a dosage sensitivity of the florigen pathway that fine-tunes shoot architecture. PLoS Genet. 2013;9(12):e1004043. doi: 10.1371/journal.pgen. 1004043. Epub Dec. 26, 2013.
Soyk et al., Variation in the flowering gene Self Pruning 5G promotes day-neutrality and early yield in tomato. Nat Genet. Jan. 2017;49(1):162-168. doi: 10.1038/ng.3733. Epub Dec. 5, 2016.
Teo et al., New insights into the regulation of inflorescence architecture. Trends Plant Sci. Mar. 2014; 19(3):158-65. doi: 10.1016/j.tplants.2013.11.001. Epub Dec. 3, 2013.
International Search Report and Written Opinion for Application No. PCT/US2020/061613 dated Mar. 23, 2021.
Marti et al. Genetic and physiological characterization of tomato cv. Micro-Tom. J Exp Bot. 2006;57(9):2037-47. doi: 10.1093/jxb/erj154. Epub May 10, 2006.
Villagarcia et al. Modification of tomato growth by expression of truncated ERECTA protein from Arabidopsis thaliana. J Exp Bot. Nov. 2012;63(18):6493-504. doi: 10.1093/jxb/ers305. Epub Oct. 23, 2012.
Stallard. A new tomato ideal for urban gardens and even outer space. Cold Spring Harbor Laboratory. Dec. 23, 2019. Retrieved from the internet: <https://www.cshl.edu/a-new-tomato-ideal-for-urban-gardens-and-even-outer-space> on Feb. 25, 2021. 1-5.
U.S. Appl. No. 13/799,831, filed Mar. 13, 2013, Lippman et al.
U.S. Appl. No. 15/643,444, filed Jul. 6, 2017, Lippman et al.

* cited by examiner

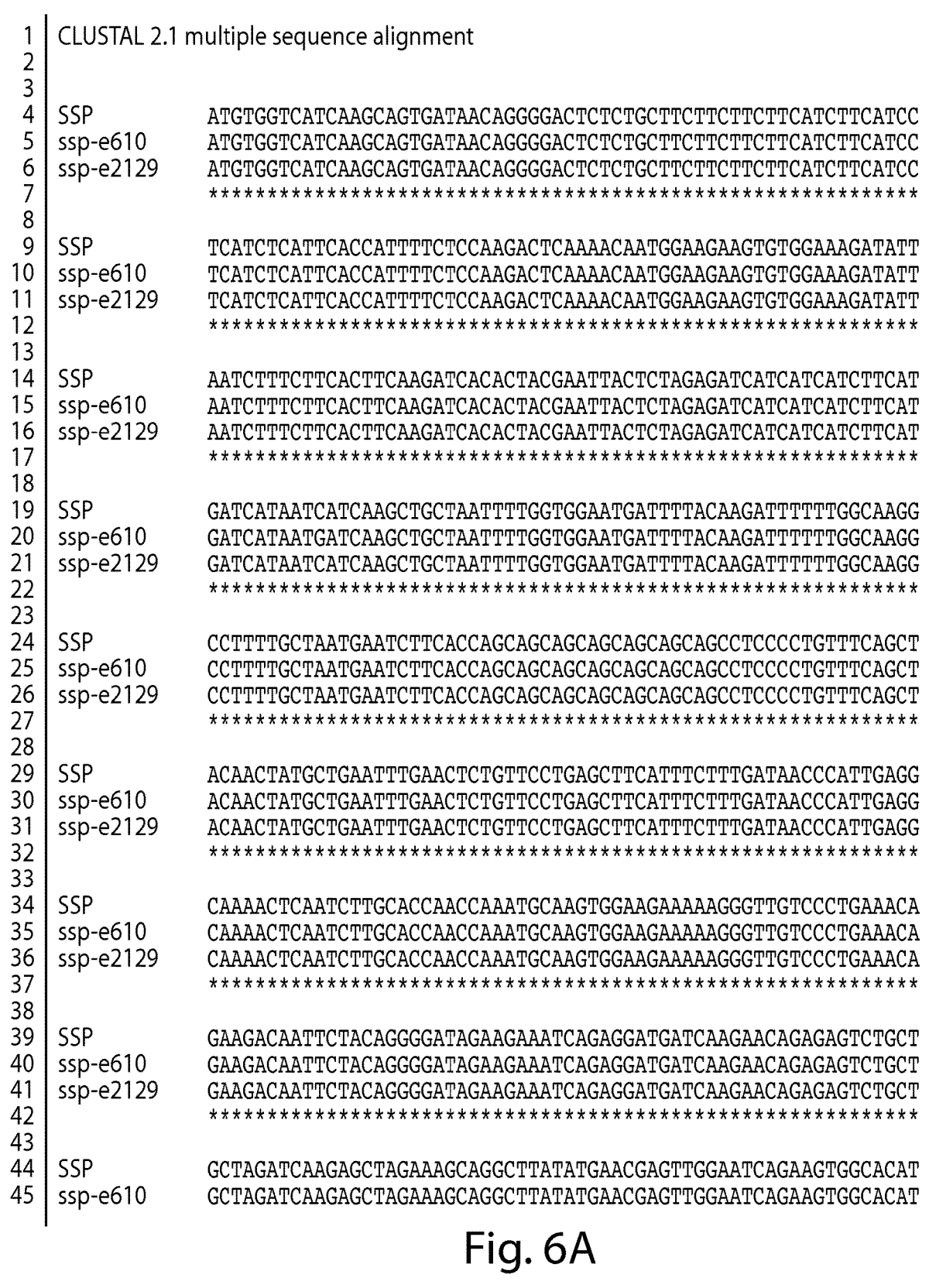

```
CLUSTAL 2.1 multiple sequence alignment


SSP          ATGTGGTCATCAAGCAGTGATAACAGGGGACTCTCTGCTTCTTCTTCTTCATCTTCATCC
ssp-e610     ATGTGGTCATCAAGCAGTGATAACAGGGGACTCTCTGCTTCTTCTTCTTCATCTTCATCC
ssp-e2129    ATGTGGTCATCAAGCAGTGATAACAGGGGACTCTCTGCTTCTTCTTCTTCATCTTCATCC
             ************************************************************

SSP          TCATCTCATTCACCATTTTCTCCAAGACTCAAAACAATGGAAGAAGTGTGGAAAGATATT
ssp-e610     TCATCTCATTCACCATTTTCTCCAAGACTCAAAACAATGGAAGAAGTGTGGAAAGATATT
ssp-e2129    TCATCTCATTCACCATTTTCTCCAAGACTCAAAACAATGGAAGAAGTGTGGAAAGATATT
             ************************************************************

SSP          AATCTTTCTTCACTTCAAGATCACACTACGAATTACTCTAGAGATCATCATCATCTTCAT
ssp-e610     AATCTTTCTTCACTTCAAGATCACACTACGAATTACTCTAGAGATCATCATCATCTTCAT
ssp-e2129    AATCTTTCTTCACTTCAAGATCACACTACGAATTACTCTAGAGATCATCATCATCTTCAT
             ************************************************************

SSP          GATCATAATCATCAAGCTGCTAATTTTGGTGGAATGATTTTACAAGATTTTTTGGCAAGG
ssp-e610     GATCATAATGATCAAGCTGCTAATTTTGGTGGAATGATTTTACAAGATTTTTTGGCAAGG
ssp-e2129    GATCATAATCATCAAGCTGCTAATTTTGGTGGAATGATTTTACAAGATTTTTTGGCAAGG
             ************************************************************

SSP          CCTTTTGCTAATGAATCTTCACCAGCAGCAGCAGCAGCAGCAGCCTCCCCTGTTTCAGCT
ssp-e610     CCTTTTGCTAATGAATCTTCACCAGCAGCAGCAGCAGCAGCAGCCTCCCCTGTTTCAGCT
ssp-e2129    CCTTTTGCTAATGAATCTTCACCAGCAGCAGCAGCAGCAGCAGCCTCCCCTGTTTCAGCT
             ************************************************************

SSP          ACAACTATGCTGAATTTGAACTCTGTTCCTGAGCTTCATTTCTTTGATAACCCATTGAGG
ssp-e610     ACAACTATGCTGAATTTGAACTCTGTTCCTGAGCTTCATTTCTTTGATAACCCATTGAGG
ssp-e2129    ACAACTATGCTGAATTTGAACTCTGTTCCTGAGCTTCATTTCTTTGATAACCCATTGAGG
             ************************************************************

SSP          CAAAACTCAATCTTGCACCAACCAAATGCAAGTGGAAGAAAAAGGGTTGTCCCTGAAACA
ssp-e610     CAAAACTCAATCTTGCACCAACCAAATGCAAGTGGAAGAAAAAGGGTTGTCCCTGAAACA
ssp-e2129    CAAAACTCAATCTTGCACCAACCAAATGCAAGTGGAAGAAAAAGGGTTGTCCCTGAAACA
             ************************************************************

SSP          GAAGACAATTCTACAGGGGATAGAAGAAATCAGAGGATGATCAAGAACAGAGAGTCTGCT
ssp-e610     GAAGACAATTCTACAGGGGATAGAAGAAATCAGAGGATGATCAAGAACAGAGAGTCTGCT
ssp-e2129    GAAGACAATTCTACAGGGGATAGAAGAAATCAGAGGATGATCAAGAACAGAGAGTCTGCT
             ************************************************************

SSP          GCTAGATCAAGAGCTAGAAAGCAGGCTTATATGAACGAGTTGGAATCAGAAGTGGCACAT
ssp-e610     GCTAGATCAAGAGCTAGAAAGCAGGCTTATATGAACGAGTTGGAATCAGAAGTGGCACAT
```

Fig. 6A

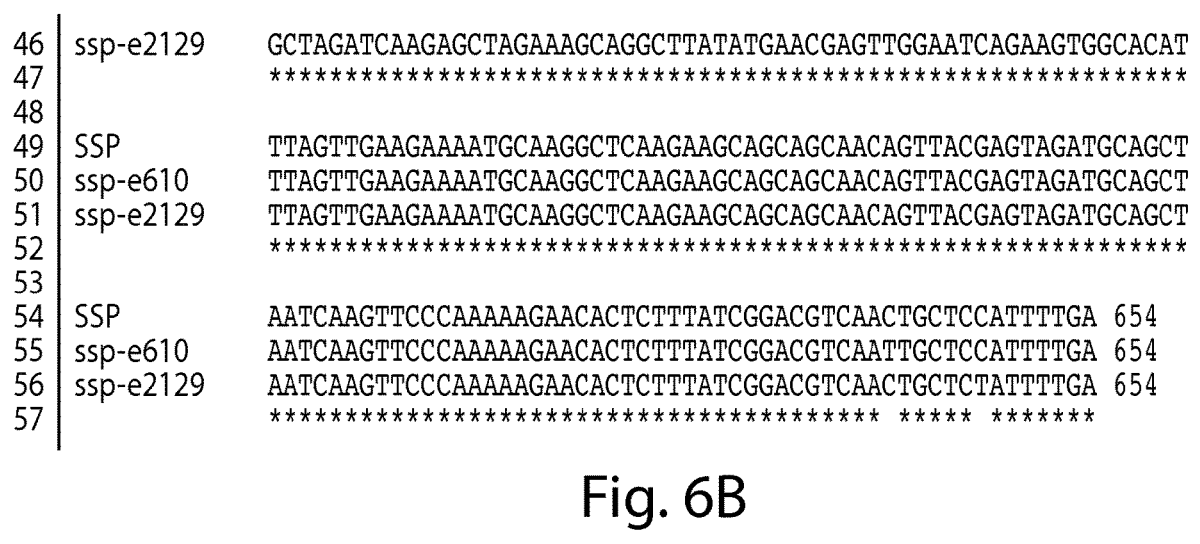

```
ssp-e2129    GCTAGATCAAGAGCTAGAAAGCAGGCTTATATGAACGAGTTGGAATCAGAAGTGGCACAT
             ************************************************************

SSP          TTAGTTGAAGAAAATGCAAGGCTCAAGAAGCAGCAGCAACAGTTACGAGTAGATGCAGCT
ssp-e610     TTAGTTGAAGAAAATGCAAGGCTCAAGAAGCAGCAGCAACAGTTACGAGTAGATGCAGCT
ssp-e2129    TTAGTTGAAGAAAATGCAAGGCTCAAGAAGCAGCAGCAACAGTTACGAGTAGATGCAGCT
             ************************************************************

SSP          AATCAAGTTCCCAAAAAGAACACTCTTTATCGGACGTCAACTGCTCCATTTTGA 654
ssp-e610     AATCAAGTTCCCAAAAAGAACACTCTTTATCGGACGTCAATTGCTCCATTTTGA 654
ssp-e2129    AATCAAGTTCCCAAAAAGAACACTCTTTATCGGACGTCAACTGCTCTATTTTGA 654
             **************************************** ***** *******
```

Fig. 6B

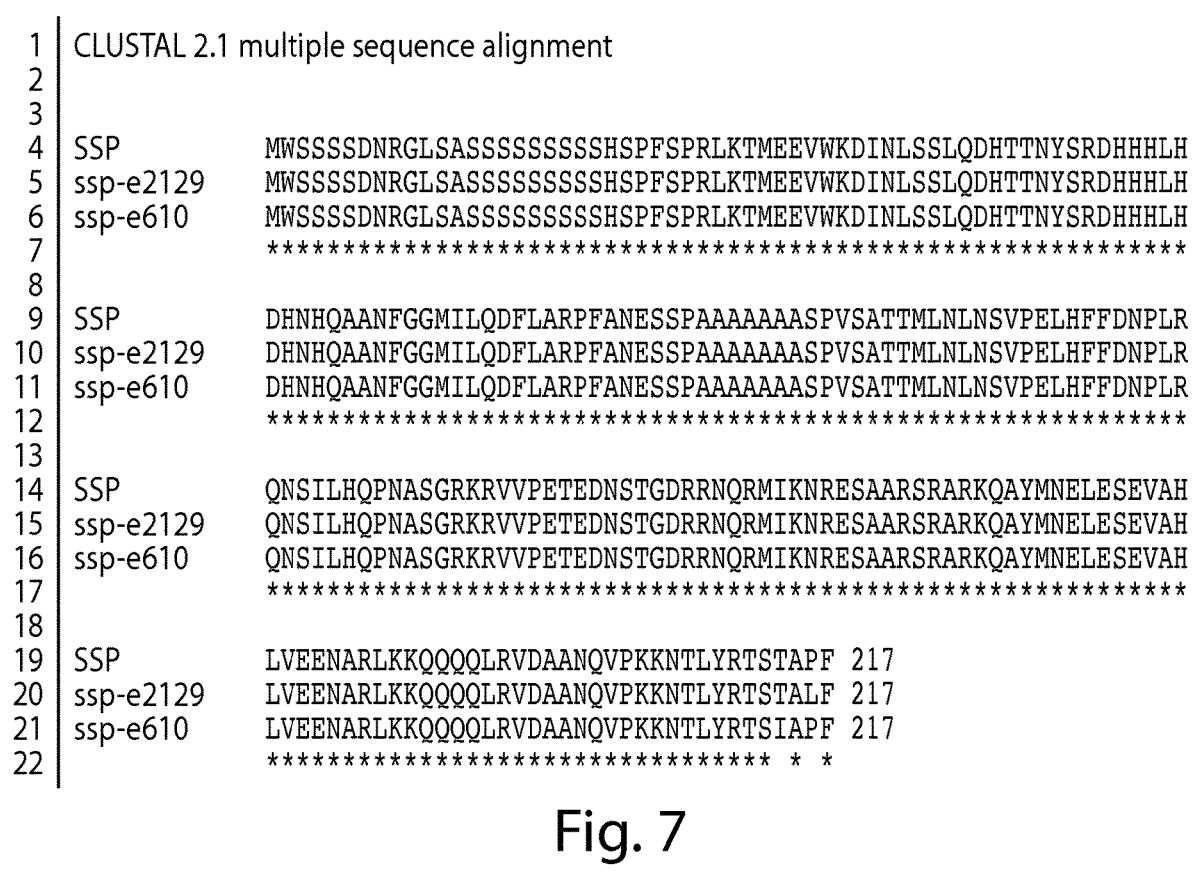

```
CLUSTAL 2.1 multiple sequence alignment


SSP          MWSSSSDNRGLSASSSSSSSSSHSPFSPRLKTMEEVWKDINLSSLQDHTTNYSRDHHHLH
ssp-e2129    MWSSSSDNRGLSASSSSSSSSSHSPFSPRLKTMEEVWKDINLSSLQDHTTNYSRDHHHLH
ssp-e610     MWSSSSDNRGLSASSSSSSSSSHSPFSPRLKTMEEVWKDINLSSLQDHTTNYSRDHHHLH
             ************************************************************

SSP          DHNHQAANFGGMILQDFLARPFANESSPAAAAAAASPVSATTMLNLNSVPELHFFDNPLR
ssp-e2129    DHNHQAANFGGMILQDFLARPFANESSPAAAAAAASPVSATTMLNLNSVPELHFFDNPLR
ssp-e610     DHNHQAANFGGMILQDFLARPFANESSPAAAAAAASPVSATTMLNLNSVPELHFFDNPLR
             ************************************************************

SSP          QNSILHQPNASGRKRVVPETEDNSTGDRRNQRMIKNRESAARSRARKQAYMNELESEVAH
ssp-e2129    QNSILHQPNASGRKRVVPETEDNSTGDRRNQRMIKNRESAARSRARKQAYMNELESEVAH
ssp-e610     QNSILHQPNASGRKRVVPETEDNSTGDRRNQRMIKNRESAARSRARKQAYMNELESEVAH
             ************************************************************

SSP          LVEENARLKKQQQQLRVDAANQVPKKNTLYRTSTAPF 217
ssp-e2129    LVEENARLKKQQQQLRVDAANQVPKKNTLYRTSTALF 217
ssp-e610     LVEENARLKKQQQQLRVDAANQVPKKNTLYRTSIAPF 217
             ********************************* * *
```

Fig. 7

CLUSTAL 2.1 multiple sequence alignment

```
SFT         ATGCCTAGAGAACGTGATCCTCTTGTTGTTGGTCGTGTGGTAGGGGATGTATTGGACCCT
sft-1906    ATGCCTAGAGAACGTGATCCTCTTGTTGTTGGTCGTGTGGTAGGGGATGTATTGGACCCT
            ************************************************************

SFT         TTCACAAGAACTATTGGCCTAAGAGTTATATATAGAGATAGAGAAGTTAATAATGGATGC
sft-1906    TTCACAAGAACTATTGGCCTAAGAGTTATATATAGAGATAGAGAAGTTAATAATGGATGC
            ************************************************************

SFT         GAGCTTAGGCCTTCCCAAGTTATTAACCAGCCAAGGGTTGAAGTTGGAGGAGATGACCTA
sft-1906    GAGCTTAGGCCTTCCCAAGTTATTAACCAGCCAAGGGTTGAAGTTGGAGGAGATGACCTA
            ************************************************************

SFT         CGTACCTTTTTCACTTTGGTTATGGTGGACCCTGATGCTCCAAGTCCGAGTGATCCAAAT
sft-1906    CGTACCTTTTTCACTTTGGTTATGGTGGACCCTGATGCTCCAAGTCCGAGTGATCCAAAT
            ************************************************************

SFT         CTGAGAGAATACCTTCACTGGTTGGTCACCGATATTCCAGCTACCACAGGTTCAAGTTTT
sft-1906    CTGAGAGAATACCTTCACTGGTTGGTCACCGATATTCCAGCTACCACAGGTTCAAGTTTT
            ************************************************************

SFT         GGGCAAGAAATAGTGAGCTATGAAAGTCCAAGACCATCAATGGGAATACATCGATTTGTA
sft-1906    GGGCAAGAAATAGTGAGCTATGAAAGTCCAAGACCATCAATGGGAATACATCGATTTGTA
            ************************************************************

SFT         TTTGTATTATTCAGACAATTAGGTCGGCAAACAGTGTATGCTCCAGGATGGCGTCAGAAT
sft-1906    TTTGTATTATTCAGACAATTAGGTCGGCAAACAATGTATGCTCCAGGATGGCGTCAGAAT
            ******************************** ***************************

SFT         TTCAACACAAGAGATTTTGCAGAACTTTATAATCTTGGTTTACCTGTTGCTGCTGTCTAT
sft-1906    TTCAACACAAGAGATTTTGCAGAACTTTATAATCTTGGTTTACCTGTTGCTGCTGTCTAT
            ************************************************************

SFT         TTTAATTGTCAAAGAGAGAGTGGCAGTGGTGGACGTAGAAGATCTGCTGATTGA
sft-1906    TTTAATTGTCAAAGAGAGAGTGGCAGTGGTGGACGTAGAAGATCTGCTGATTGA
            ******************************************************
```

Fig. 9

CLUSTAL 2.1 multiple sequence alignment

```
SFT          MPRERDPLVVGRVVGDVLDPFTRTIGLRVIYRDREVNNGCELRPSQVINQPRVEVGGDDL
sft-1906     MPRERDPLVVGRVVGDVLDPFTRTIGLRVIYRDREVNNGCELRPSQVINQPRVEVGGDDL
             ************************************************************

SFT          RTFFTLVMVDPDAPSPSDPNLREYLHWLVTDIPATTGSSFGQEIVSYESPRPSMGIHRFV
sft-1906     RTFFTLVMVDPDAPSPSDPNLREYLHWLVTDIPATTGSSFGQEIVSYESPRPSMGIHRFV
             ************************************************************

SFT          FVLFRQLGRQTVYAPGWRQNFNTRDFAELYNLGLPVAAVYFNCQRESGSGGRRRSAD
sft-1906     FVLFRQLGRQTMYAPGWRQNFNTRDFAELYNLGLPVAAVYFNCQRESGSGGRRRSAD
             ***********:*********************************************
```

Fig. 10

MUTATIONS IN SOLANACEAE PLANTS THAT MODULATE SHOOT ARCHITECTURE AND ENHANCE YIELD-RELATED PHENOTYPES

CROSS-REFERENCE TO RELATED APPLICATIONS

This application is a national phase filing under 35 U.S.C. § 371 of International Application No. PCT/US2013/070825, filed Nov. 19, 2013, which claims the benefit under 35 U.S.C § 119(e) of the filing date of U.S. Provisional Application No. 61/728,654, filed Nov. 20, 2012, and of the filing date of U.S. Provisional Application No. 61/869,052, filed Aug. 22, 2013 and is a Continuation-in-Part of U.S. application Ser. No. 13/799,831 filed Mar. 13, 2013. The entire teachings contents of each of these referenced applications are incorporated by reference herein.

FEDERALLY SPONSORED RESEARCH OR DEVELOPMENT

This invention was made with government support under federal grant number IOS-1237880 awarded by the National Science Foundation. The government has certain rights in the invention.

BACKGROUND

There are ongoing attempts to enhance yield and quality, as well as life span, of food crops and other plants, such as ornamental plants and trees, in an effort to use resources more efficiently and produce more food, flowers and trees. Additional approaches for doing so are still needed, and one of the primary targets for manipulating plant productivity is the flowering process and its corresponding effects on vegetative and reproductive shoot architecture.

SUMMARY

Described herein are novel genetic variants of Solanaceae plants, e.g., tomato plants, that (a) exhibit modified flowering time and shoot architecture; (b) exhibit higher yield, higher quality products (e.g., fruits); (c) produce products (e.g., fruits) with different compositions, (e.g., brix, also known as enhanced soluble solids or sugar concentration in the fruits); or (d) any combination of (a) to (c), compared to corresponding "wild-type (WT)" Solanaceae plants (Solanaceae plants that have not been genetically altered).

In one embodiment, a genetically-altered plant, such as a genetically-altered semi-determinate or semi-indeterminate Solanaceae plant, comprises a mutant suppressor of sp1 (ssp1) gene and a mutant single flower truss (sft) gene. Such Solanaceae plants are heterozygous or homozygous for mutant genes (e.g., heterozygous or homozygous for a mutant suppressor of sp1 (ssp1) gene or heterozygous or homozygous for a mutant single flower truss (sft) gene) or heterozygous or homozygous for both a mutant suppressor of sp1 (ssp1) gene and a mutant single flower truss (sft) gene (double heterozygotes or double homozygotes). Such plants may further comprise a mutant self pruning (sp) gene. Such plants may be heterozygous or homozygous for a mutant self pruning (sp) gene. Such plants can also be in the wild type SELF PRUNING (SP) background.

In a further embodiment, Solanaceae plants comprise a mutant self pruning (sp) gene and a mutant single flower truss (sft) gene. Such Solanaceae plants are heterozygous or homozygous for mutant genes (e.g., for a mutant self pruning (sp) gene or for a mutant single flower truss (sft) gene) or heterozygous or homozygous for both a mutant self pruning (sp) gene and a mutant single flower truss (sft) gene (double heterozygotes or double homozygotes).

In another embodiment, Solanaceae plants comprise a mutant self pruning (sp) gene and a mutant suppressor of sp1 (ssp1) gene. Such Solanaceae plants are heterozygous or homozygous for mutant genes (e.g., for a mutant self pruning (sp) gene or for a mutant suppressor of sp1 (ssp1) gene) or heterozygous or homozygous for both a mutant self pruning (sp) gene and a mutant suppressor of sp1 (ssp1) gene (double heterozygotes or double homozygotes).

In yet another embodiment, Solanaceae plants comprise a mutant suppressor of sp1 (ssp1) gene or a mutant single flower truss (sft) gene. Such Solanaceae plants are heterozygous or homozygous for a mutant suppressor of sp1 (ssp1) gene or heterozygous or homozygous for a mutant single flower truss (sft) gene. Such plants may further comprise a mutant self pruning (sp) gene. Such plants may be heterozygous or homozygous for a mutant self pruning (sp) gene. Such plants can also be in the wild type SELF PRUNING (SP) background.

In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant ssp1 gene is ssp-2129 or ssp-610. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10). SEQ ID NO: 2 is the nucleotide sequence of the coding sequence of ssp-2129, a mutant allele of SSP1. SEQ ID NO: 3 is the nucleotide sequence of the coding sequence of ssp-610, a mutant allele of SSP1. SEQ ID NO: 5 is the amino acid sequence of ssp-2129 mutant protein. SEQ ID NO: 6 is the amino acid sequence of ssp-610 mutant protein. In some embodiments, the mutant sft gene comprises a coding sequence that comprises the nucleic acid sequence of SEQ ID NO: 20. In some embodiments, the mutant sft gene comprises SEQ ID NO: 20. In some embodiments, the mutant sft gene comprises the nucleic acid sequence of SEQ ID NO: 17. In some embodiments, the mutant sft gene encodes a mutant sft polypeptide comprising the sequence of SEQ ID NO: 21. In some embodiments, the mutant sft gene comprises a nucleotide sequence that encodes a mutant sft polypeptide comprising a Val to Met mutation at position 132 of SEQ ID NO: 19. In some embodiments, the mutant sft gene is sft-1906.

In some embodiments, the genetically-altered Solanaceae plant is a genetically altered semi-determinate or semi-indeterminate Solanaceae plant, such as a tomato (*Solanum lycopersicum*) plant. In some embodiments, the genetically-altered semi-determinate or semi-indeterminate Solanaceae plant is isogenic. In some embodiments, the genetically-altered semi-determinate or semi-indeterminate Solanaceae plant is inbred. In some embodiments, the genetically-altered semi-determinate or semi-indeterminate Solanaceae plant is a hybrid.

In another aspect, the disclosure relates to a seed for producing a genetically-altered Solanaceae plant, such as a semi-determinate or semi-indeterminate genetically-altered Solanaceae plant, as described herein, e.g., a genetically-altered semi-determinate or semi-indeterminate Solanaceae plant comprising (e.g., heterozygous or homozygous for) a mutant single flower truss (sft) gene and a mutant suppressor of sp1 (ssp1) gene, a genetically-altered semi-determinate or semi-indeterminate Solanaceae plant comprising (e.g., heterozygous or homozygous for) a mutant single flower truss (sft) gene and a mutant self pruning (sp) gene, a genetically-altered semi-determinate or semi-indeterminate Solanaceae plant comprising (e.g., heterozygous or homozygous for) a mutant suppressor of sp1 (ssp1) gene and a mutant self pruning (sp) gene, or a genetically-altered semi-determinate or semi-indeterminate Solanaceae plant comprising (e.g., heterozygous or homozygous for) a mutant single flower truss (sft) gene, a mutant suppressor of sp1 (ssp1) gene, and a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif comprising SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10).

In yet another aspect, the disclosure relates to methods of producing a genetically-altered Solanaceae plant, such as a semi-determinate or semi-indeterminate Solanaceae plant. In some embodiments, the method comprises:

(a) introducing a mutant sft gene into a Solanaceae plant containing a mutant ssp1 gene (or alternatively introducing a mutant ssp1 gene into a Solanaceae plant containing a mutant sft gene), thereby producing a genetically-altered Solanaceae plant containing a mutant sft gene and a mutant ssp1 gene; and (b) self-crossing the genetically-altered Solanaceae plant produced in (a) or crossing two genetically-altered Solanaceae plants produced in (a) under conditions appropriate for producing a genetically-altered Solanaceae plant heterozygous or homozygous for the mutant sft gene and heterozygous or homozygous for the mutant ssp1 gene. In some embodiments, the plant produced in (b) is heterozygous for the mutant sft gene and heterozygous for the mutant ssp1 gene. In some embodiments, the plant produced in (b) further comprises a mutant sp gene (e.g., is heterozygous or homozygous for a mutant sp gene).

In some embodiments, the method of producing a genetically-altered Solanaceae plant comprises:

(a) introducing a mutant sft gene into a Solanaceae plant part containing a mutant ssp1 gene (or alternatively introducing a mutant ssp1 gene into a Solanaceae plant part containing a mutant sft gene), thereby producing a genetically-altered Solanaceae plant part containing the mutant sft gene and the mutant ssp1 gene;

(b) maintaining the genetically-altered Solanaceae plant part containing a mutant sft gene and a mutant ssp1 gene produced in (a) under conditions and for sufficient time for production of a genetically-altered Solanaceae plant containing the mutant sft gene and the mutant ssp1 gene from the plant part, thereby producing a genetically-altered Solanaceae plant containing the mutant sft gene and the mutant ssp1 gene;

(c) self-crossing the genetically-altered Solanaceae plant produced in (b) or crossing two genetically-altered Solanaceae plants produced in (b) under conditions appropriate for producing a genetically-altered Solanaceae plant heterozygous or homozygous for the mutant sft gene and heterozygous or homozygous for the mutant ssp1 gene, thereby producing a genetically-altered Solanaceae plant. In some embodiments, the plant produced in (c) is heterozygous for the mutant sft gene and heterozygous for the mutant ssp1 gene. In some embodiments, the plant produced in (c) further comprises a mutant sp gene (e.g., is heterozygous or homozygous for a mutant sp gene).

In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10). In some embodiments, the mutant sft gene comprises a coding sequence that comprises SEQ ID NO: 20. In some embodiments, the mutant sft gene comprises SEQ ID NO: 20. In some embodiments, the mutant sft gene comprises SEQ ID NO: 17. In some embodiments, the mutant sft gene comprises a nucleic acid sequence that encodes a mutant sft polypeptide comprising the sequence of SEQ ID NO: 21. In some embodiments, the mutant sft gene and/or mutant ssp1 gene is introduced into a plant or a plant part by a method selected from the group consisting of: *Agrobacterium*-mediated recombination, viral-vector mediated recombination, microinjection, gene gun bombardment/biolistic particle delivery, nuclease mediated recombination, and electroporation. In some embodiments, the Solanaceae plant is a tomato (*Solanum lycopersicum*) plant. In some embodiments, the genetically-altered Solanaceae plant is a plant that suppresses sp imposed determinate growth and exhibits a sympodial index of less than three and either terminates (is semi-determinate), or continues to produce sympodial shoots (is semi-indeterminate). Accordingly, in some embodiments, the Solanaceae plant is semi-determinate or semi-indeterminate. In some embodiments, the Solanaceae plant is a semi-determinate or semi-indeterminate plant with a sympodial index of less than 3, less than 2.5, less than 2, or less than 1.5. In some embodiments, the Solanaceae plant is a semi-determinate or semi-indeterminate tomato plant. In some embodiments, the Solanaceae plant is a semi-determinate or semi-indeterminate tomato plant with a sympodial index of less than 3, less than 2.5, less than 2, or less than 1.5

In some embodiments, the Solanaceae plant is inbred. In some embodiments, the genetically-altered semi-determinate Solanaceae plant is a hybrid. In another aspect, the disclosure relates to a genetically-altered Solanaceae plant produced by or producible by the methods described herein.

In another aspect, the disclosure relates to a genetically-altered Solanaceae plant, e.g., a semi-determinate or semi-indeterminate Solanaceae plant, homozygous for a mutant suppressor of sp1 (ssp1) gene and homozygous for a self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10).

In some embodiments, the genetically-altered Solanaceae plant, e.g., a semi-determinate or semi-indeterminate Solanaceae plant, is a tomato (*Solanum lycopersicum*) plant. In some embodiments, the genetically-altered Solanaceae plant, e.g., a semi-determinate or semi-indeterminate Solanaceae plant, is isogenic. In some embodiments, the genetically-altered Solanaceae plant, e.g., a semi-determinate or semi-indeterminate Solanaceae plant, is inbred. In some embodiments, the genetically-altered Solanaceae plant, e.g., a semi-determinate or semi-indeterminate Solanaceae plant, is a hybrid.

In another aspect, the disclosure relates to a genetically-altered Solanaceae plant heterozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10). In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered semi-determinate Solanaceae plant is a hybrid.

In another aspect, the disclosure relates to a genetically-altered Solanaceae plant homozygous for a mutant suppressor of sp1 (ssp1) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10). In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered semi-determinate Solanaceae plant is a hybrid. In some embodiments, the genetically-altered Solanaceae plant is homozygous for a wild-type SELF PRUNING (SP) gene.

In another aspect, the disclosure relates to a seed for producing a genetically-altered semi-determinate or semi-indeterminate Solanaceae plant as described herein, e.g. a genetically-altered semi-determinate or semi-indeterminate Solanaceae plant homozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10).

In yet another aspect, the disclosure relates to methods of producing a genetically-altered semi-determinate or semi-indeterminate Solanaceae plant. In some embodiments, the method comprises:

(a) introducing a mutant ssp1 gene into a Solanaceae plant containing a mutant sp gene, thereby producing a genetically-altered Solanaceae plant containing a mutant ssp1 gene and a mutant sp gene; and (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and the mutant sp gene, thereby producing a genetically-altered Solanaceae plant that is semi-determinate or semi-indeterminate. In some embodiments, the method of producing a genetically-altered semi-determinate or semi-indeterminate Solanaceae plant comprises:

(a) introducing a mutant ssp1 gene into a Solanaceae plant part containing a mutant sp gene, thereby producing a genetically-altered Solanaceae plant part containing the mutant ssp1 gene and the mutant sp gene;

(b) maintaining the genetically-altered Solanaceae plant part containing a mutant ssp1 and a mutant sp gene produced in (a) under conditions and for sufficient time for production of a genetically-altered Solanaceae plant containing the mutant ssp1 gene and the mutant sp gene from the plant part, thereby producing a genetically-altered Solanaceae plant containing the mutant ssp1 gene and the mutant sp gene;

(c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sp gene, thereby producing a genetically-altered Solanaceae plant that is semi-determinate or semi-indeterminate. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises a coding sequence that comprises the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant ssp1 gene comprises the nucleic acid sequence of SEQ ID NO: 25 or SEQ ID NO: 26. In some embodiments, the mutant sp gene comprises a coding sequence that comprises the nucleic acid sequence of SEQ ID NO: 8. In some embodiments, the mutant sp gene comprises the nucleic acid sequence of SEQ ID NO: 8. In some embodiments, the mutant sp gene comprises the nucleic acid sequence of SEQ ID NO: 23. In some embodiments, the mutant sp gene comprises a nucleic acid that encodes the amino acid sequence of mutant sp protein (e.g., SEQ ID NO: 10). In some embodiments, the mutant ssp1 gene is introduced into a plant or a plant part by a method selected from the group consisting of: *Agrobacterium*-mediated recombination, viral-vector mediated recombination, microinjection, gene gun bombardment/biolistic particle delivery, nuclease mediated recombination, and electroporation. In some embodiments, the Solanaceae plant is a tomato (*Solanum lycopersicum*) plant. In some embodiments, the Solanaceae plant is inbred. In some embodiments, the genetically-altered semi-determinate Solanaceae plant is a hybrid. In another aspect, the disclosure relates to a genetically-altered semi-determinate Solanaceae plant produced by or producible by the methods herein.

Other aspects of the disclosure relate to isolated polynucleotides or isolated polypeptides. In some embodiments, the isolated polynucleotide encodes a mutant ssp1 protein having the amino acid sequence of SEQ ID NO: 5 or SEQ ID NO: 6. In some embodiments, the isolated polynucleotide comprises the nucleic acid sequence of SEQ ID NO: 2 or SEQ ID NO: 3. In some embodiments, the isolated polynucleotide encodes a mutant sft protein having the amino acid sequence of SEQ ID NO: 21. In some embodiments, the isolated polynucleotide comprises the nucleic acid sequence of SEQ ID NO: 20.

Other aspects of the disclosure relate to plant cells and food products as described herein.

BRIEF DESCRIPTION OF THE DRAWINGS

FIG. 4 is a series of graphs showing shoot determinacy of the primary shoot, the inflorescence, and the sympodial shoot in M82 indeterminate (M82ID), M82 determinate (M82D), two ssp1 mutant alleles (ssp-2129 and ssp-610), the sft-1906 mutant allele, and all genotypic combinations among mutant alleles.

FIGS. 6A and 6B is a ClustalW analysis of the nucleotide sequence of the coding sequence of the wild-type SSP1gene and the coding sequences of the two mutant alleles e610 and e2129 (SEQ ID NOs: 1, 3 and 2, respectively).

FIG. 7 is a ClustalW analysis of the amino acid sequence of the wild-type SSP1gene and the two mutant alleles e610 and e2129 (SEQ ID NOs: 4, 6 and 5, respectively).

FIG. 8A shows brix-yield (brix×yield) of plants of the genotypes indicated. FIG. 8B shows (soluble solids, sugar concentration in the fruits) of plants of the genotypes indicated. FIG. 8C shows yield of red fruit for plants of the genotypes indicated. FIG. 8D shows total yield of fruit for plants of the genotypes indicated. Yield was measured by taking 15 plants from each genotype in a completely randomized design with 1 plant/meter squared. * $P<0.05$, ** $P<0.01$, students t-test against M82D. Error bars are standard error.

FIG. 9 is a ClustalW analysis of the nucleotide sequence of the wild-type SFT coding sequence and the mutant allele sft-1906 coding sequence (SEQ ID NOs: 18 and 20, respectively).

FIG. 10 is a ClustalW analysis of the amino acid sequence of the wild-type SFT gene and the mutant allele sft-1906 (SEQ ID NOs: 19 and 21, respectively).

SEQUENCES

Figure 1:
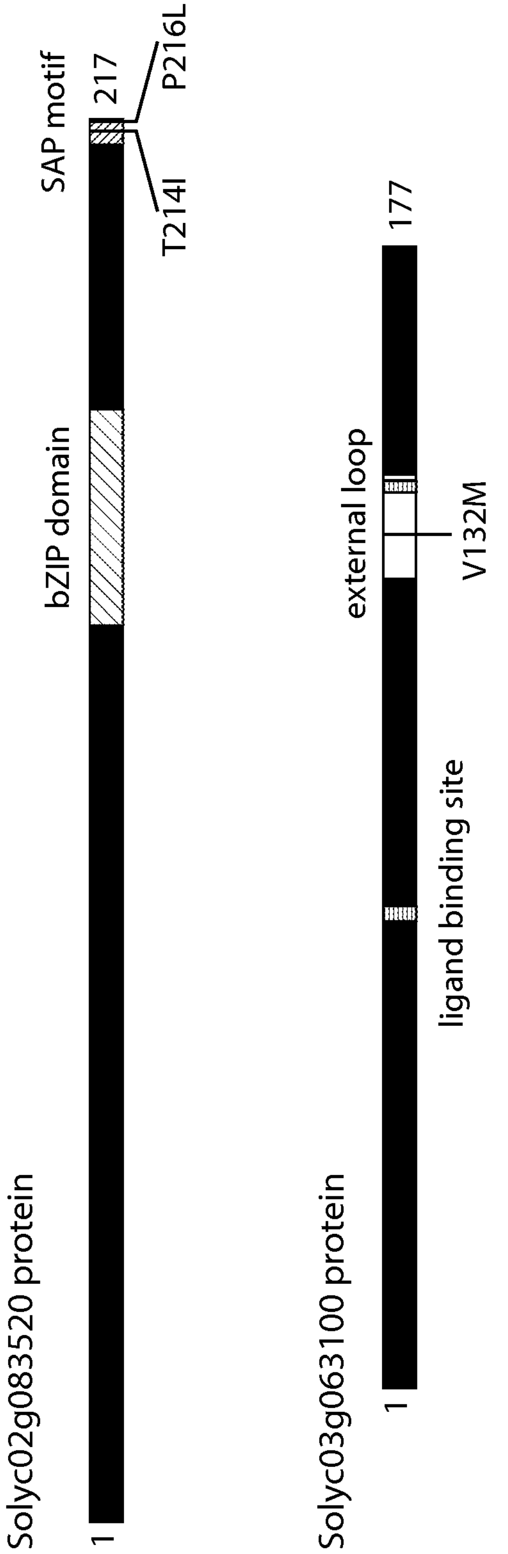
FIG. 1 shows the SSP1 protein and SFT protein. The bZIP domain and SAP motif are indicated and the two mutations (ssp-2129 and ssp-610) in the SAP motif of the SSP1 protein are indicated: Proline to Leucine (P216L) and Threonine to Isoleucine (T214I), respectively. Two putative ligand binding sites are indicated and the mutation in the external loop region of the SFT protein is indicated (se).

SEQ ID NO: 1 is the nucleotide sequence of the coding sequence of wild-type tomato SSP1.

SEQ ID NO: 2 is the nucleotide sequence of the coding sequence of ssp-2129, a mutant allele of SSP1.

SEQ ID NO: 3 is the nucleotide sequence of the coding sequence of ssp-610, a mutant allele of SSP1.

SEQ ID NO: 4 is the amino acid sequence of wild-type tomato SSP1 protein.

SEQ ID NO: 5 is the amino acid sequence of ssp-2129 mutant protein.

SEQ ID NO: 6 is the amino acid sequence of ssp-610 mutant protein.

SEQ ID NO: 7 is the nucleotide sequence of the coding sequence of wild-type tomato SP gene.

SEQ ID NO: 8 is the nucleotide sequence of the coding sequence of a mutant sp gene.

SEQ ID NO: 9 is the amino acid sequence of wild-type SP protein.

SEQ ID NO: 10 is the amino acid sequence of mutant sp protein.

SEQ ID NO: 11 is the amino acid sequence of the SAP motif of the tomato SSP1 protein.

SEQ ID NO: 12 is the nucleotide sequence of ssp-2129 that encodes the mutant SAP motif of ssp-2129 protein.

SEQ ID NO: 13 is the nucleotide sequence of ssp-610 that encodes the mutant SAP motif of ssp-610 protein.

SEQ ID NO: 14 is the amino acid sequence of the mutant SAP motif of ssp-2129 protein.

SEQ ID NO: 15 is the amino acid sequence of the mutant SAP motif of ssp-610 protein.

SEQ ID NO: 16 is the nucleic acid sequence of SFT wild-type genomic region.

SEQ ID NO: 17 is the nucleic acid sequence of sft-1906, a mutant allele of SFT, genomic region.

SEQ ID NO: 18 is the nucleic acid sequence of the coding sequence of wild-type SFT DNA.

SEQ ID NO: 19 is the amino acid sequence of wild-type SFT protein.

SEQ ID NO: 20 is the nucleic acid sequence of the coding sequence of sft-1906, a mutant of SFT.

SEQ ID NO: 21 is the amino acid sequence of mutant sft protein.

SEQ ID NO: 22 is the nucleic acid sequence of SP wild-type genomic region.

SEQ ID NO: 23 is the nucleic acid sequence of sp mutant genomic region.

SEQ ID NO: 24 is the nucleic acid sequence of SSP wild-type genomic region.

SEQ ID NO: 25 is the nucleic acid sequence of ssp-2129 mutant genomic region.

SEQ ID NO: 26 is the nucleic acid sequence of ssp-610 mutant genomic region.

DETAILED DESCRIPTION

Tomato yield, on both a per plant basis and in the context of tons per acre, depends partly on fruit size, but is mainly driven by the production of dozens of multi-flowered inflorescences and resulting fruit clusters that develop according to the "sympodial" growth habit. The defining feature of sympodial plants is that the shoot apical meristem (SAM) ends growth by differentiating into a terminal flower after producing a set number of leaves, and growth then renews from a specialized axillary (sympodial) meristem (SYM) that, in tomato, produces just three leaves before undergoing its own flowering transition and termination. Indefinite reiteration of three-leaf sympodial flowering events results in an "indeterminate" plant that continuously produces equally spaced inflorescences. The regular production of leaves between inflorescences is known as the "sympodial index" (SI).

Tomato breeding goals are multifaceted and shift according to the needs and desires of growers (e.g. improved pest resistances) and consumers (e.g. better quality), but one unwavering aim is to improve yield. Indeterminate cultivars are grown commercially to enable continuous market delivery of "round", "roma", "cocktail", "grape", and "cherry" tomato types that are eaten fresh and command a premium price. Indeterminate tomatoes are primarily grown in greenhouses where successively ripening clusters are harvested by hand multiple times over an extended period, in some cases up to a year, to maximize yield on plants that must be pruned to one or two main shoots to enable efficient greenhouse growth and maintain fresh market quality. While the necessary pruning of indeterminate tomatoes facilitates agronomic practices that maximize quality, such as size, shape, and flavor, it also limits yield. In contrast, tomatoes grown for sauces, pastes, juices, or other processed can or jar products where fruit quality is less relevant, must be managed agronomically to produce maximum yields (per acre) through once-over mechanical harvests to be economically justified. Maximal yields for processing tomatoes are achieved by growing determinate sp mutants in the open field to their full potential, because sequential sympodial shoots transition to flowering progressively faster in sp plants, which results in a compact bush-like form where fruits ripen uniformly. Thus, sp varieties lend themselves to once-over mechanical harvesting and have therefore come to dominate the processing tomato industry, although determinate varieties have also been bred for fresh market production. In a parallel to the physical pruning of indeterminate tomatoes, one drawback of sp-imposed determinate growth is that inflorescence and fruit production is restricted, because of a genetic pruning that causes sympodial cycling to stop. Thus, maximizing inflorescence and fruit production while simultaneously minimizing shoot production for the tomato industry has remained a challenging goal.

One approach to increase inflorescence production and yield is to reduce SI to less than three. As described herein, chemically induced mutant populations of tomatoes in the self pruning (sp) background were screened for mutations that suppressed sp imposed growth determinacy, with the goal of producing indeterminate tomatoes with reduced SI. Three mutants were identified. The first mutant carried a novel mutation in the gene SINGLE FLOWER TRUSS (SFT), the mutation referred to herein as sft-1906, which resulted in a weak allele. SFT is the tomato ortholog of the *Arabidopsis thaliana* gene FLOWERING LOCUS T (FT). The other two mutants were defective in a gene designated SUPPRESSOR OF SP1 (SSP1), which encodes a protein partner of SFT. SSP1 is the tomato ortholog of the *Arabidopsis thaliana* gene FLOWERING LOCUS D (FD). These other two mutants are referred to herein as ssp-2129 or ssp-610. Remarkably, each homozygous sft and ssp1 mutant transforms determinate tomato plants into indeterminate tomato plants with a SI of less than three.

As described herein, data was generated in cherry and roma tomato types that demonstrate the utility of the new SFT and SSP1 mutations to serve as novel germplasm for breeding. Specifically, it was found that mixing and matching these mutations in various homozygous and heterozygous combinations resulted in a quantitative range of sympodial indices and novel determinate, semi-determinate, and indeterminate shoot architectures that have not been possible to achieve with existing breeding germplasm. Notably, it has been also found that these mutations increase the number of flowers per inflorescence.

The SSP1 and SFT mutations were introduced into the classic mutant self-pruning (sp) determinate background (sp-classic, coding sequence is SEQ ID NO: 8), which is a prerequisite genotype for generating indeterminate plants with a SI of less than 3. SP is the tomato ortholog of the *Arabidopsis thaliana* gene TERMINAL FLOWER1 (TFL1). Data from the roma cultivar 'M82' (which is homozygous for sp-classic) showed that homozygosity for ssp-2129 or ssp-610 in the sp-classic background results in semi-indeterminate plants with an average SI of 2. Data from a determinate variety of the cherry type 'Currant' tomato (*S. pimpinellifolium*) showed that homozygosity for sft-1906 or either of the ssp1 mutations created a SI of 2. Double heterozygotes of sft-1906 and ssp-2129 or ssp-610 in hybrids resulted in an average SI less than 2, illustrating that combining mutations in either homozygous or heterozygous states can lead to subtle quantitative manipulation of sympodial shoot architecture and yield potential. Finally, all three mutants increase the number of flowers per inflorescence, with sft-1906 exhibiting the strongest effect.

Described herein are genetically-altered Solanaceae plants, such as genetically-altered semi-determinate (SD) or semi-indeterminate (SID) Solanaceae plants, e.g., a tomato plant (*Solanum lycopersicum*), that comprise a mutant gene or mutant genes and exhibit characteristics different from those of the corresponding plant that has not been genetically altered. The characteristics include any combination of the following: modified flowering time and shoot architecture; higher yield; higher quality products (e.g., fruits); and products (e.g., fruits) with different compositions (e.g., brix, also known as enhanced soluble solids or sugar concentration in the fruits), compared to corresponding "wild-type (WT)" Solanaceae plants that have not been genetically altered. In some embodiments, the genetically-altered Solanaceae plant has a sympodial index of less than 3, less than 2.5, less than 2, or less than 1.5. In some embodiments, the genetically-altered Solanaceae plant has a sympodial index of between 1 and 3 or between 1.5 and 2.5.

In some embodiments, genetically-altered heterozygous or homozygous Solanaceae plants, e.g., tomato plants (*Solanum lycopersicum*), comprise a mutant flowering gene SSP1 (ssp1) and mutant FLOWERING LOCUS gene SFT (sft). In some embodiments, the genetically-altered heterozygous plants are semi-determinate (SD) or semi-indeterminate (SID). Such plants have increased yield; higher quality products (e.g., fruits); and products (e.g., fruits) with different compositions (e.g., brix, also known as enhanced soluble solids or sugar concentration in the fruits) relative to these characteristics of corresponding plants that do not comprise such mutant genes. The plants comprise a variety of combinations of the different mutant alleles, such as mutant ssp1 (e.g., ssp-2129, ssp-610) with sft mutations (e.g., sft-1906). The genetically-altered plants are heterozygotes or homozygotes and, in some cases, are double heterozygotes or double homozygotes. In one embodiment, such plants comprise ssp-2129, described herein, and mutant SFT, such as sft-1906. In another embodiment, the plants comprise ssp-610, described herein, and mutant SFT, such as sft-1906.

Figure 8A:
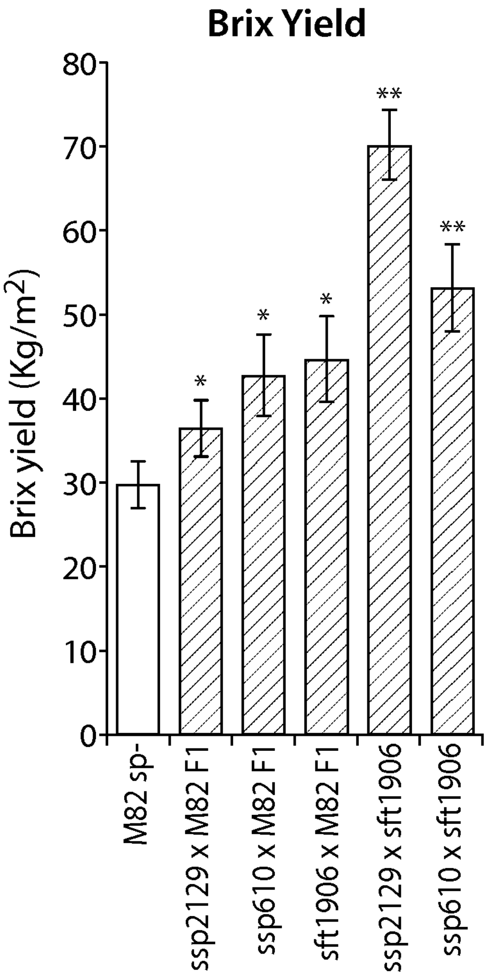
FIG. 8A-8D are graphic representations of results of assessment of characteristics of plants of the genotypes indicated.
Figure 8B:
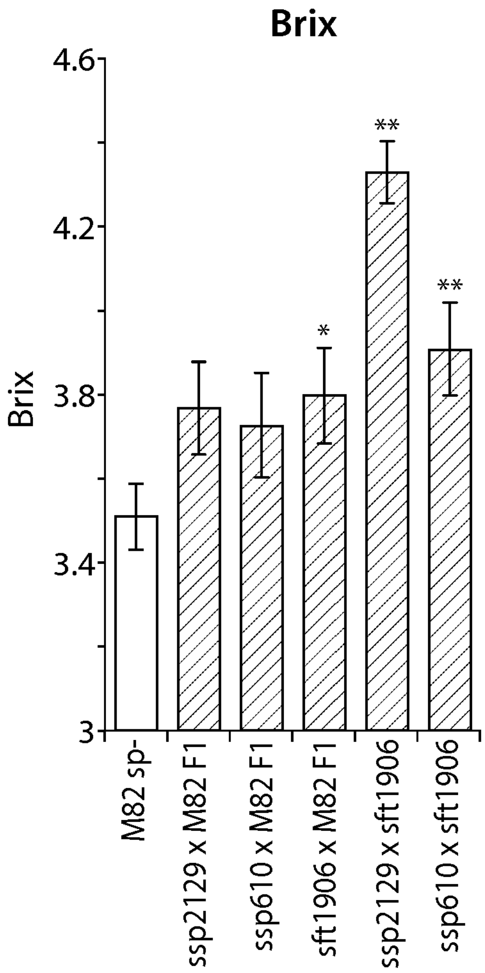
Figure 8C:
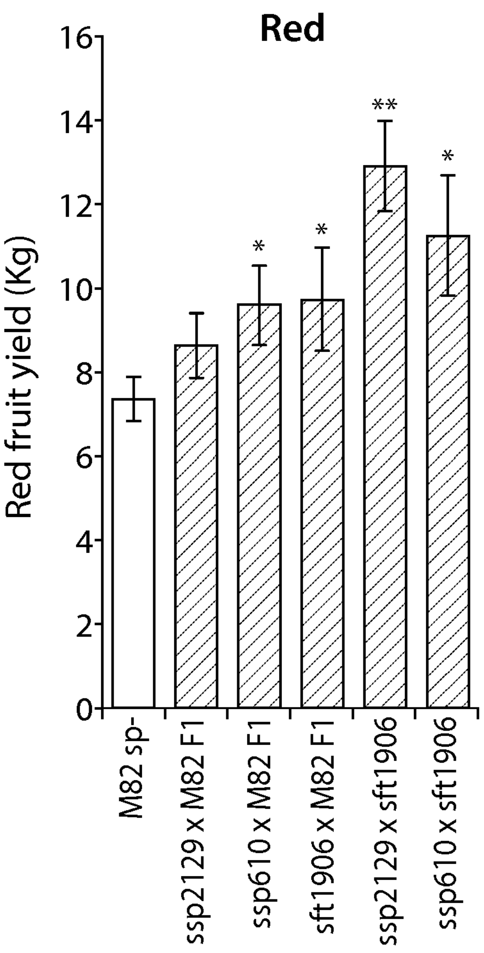
Figure 8D:
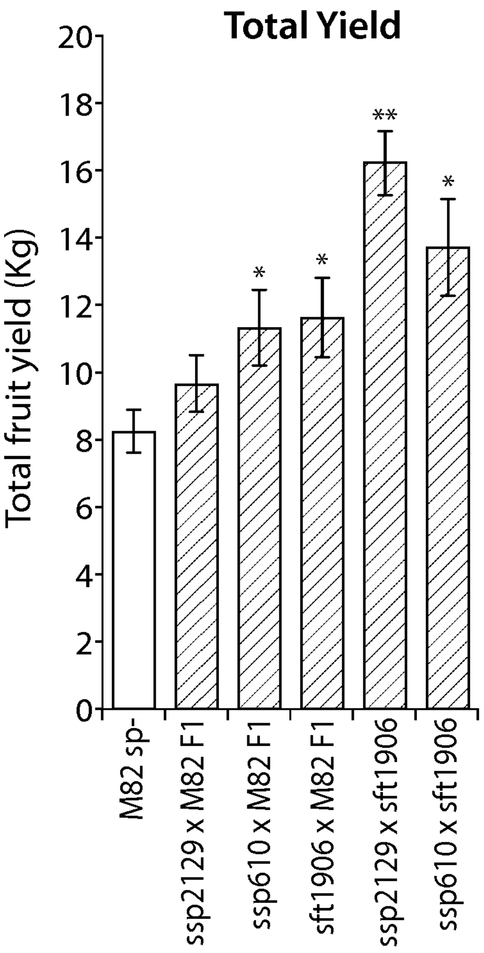

In a specific embodiment, genetically-altered Solanaceae plants, such as tomato plants designated herein as sft-1906 x M82 F1, exhibited greater yield than the corresponding wild type tomato plants. See, for example, FIG. 8D. Similarly, other genetically-engineered tomato plants produced greater yields (total fruit, red fruit, for example) than the corresponding wild-type tomato plants. See FIGS. 8C and 8D, graphic representations of yield of fruit by heterozygous tomato plants described herein (e.g., double heterozygotes ssp2129 x sft1906 and ssp610 x sft1906, as well as the three heterozygotes indicated: sft1906 x M82F1; ssf610 x M82F1; ssp2129 x M82F1).

Also described herein are semi-determinate (SD) or semi-indeterminate (SID) Solanaceae plants, e.g., a tomato plant (*Solanum lycopersicum*), that comprise a mutant of SUPPRESSOR OF SP1 (SSP1). The SSP1 gene encodes a bZIP transcription factor that physically interacts with the florigen hormone, SFT, to induce the flowering transition and flower production. SSP1 has two domains, the bZIP domain and the SAP motif (FIG. 1). The bZIP domain contains a basic leucine zipper capable of interacting with DNA. The SAP motif, "RTSTAPF" (SEQ ID NO: 11), is found in the C-terminus of SSP1 from amino acid position 211 to 217 in SEQ ID NO: 4. The SAP motif is similar to a conventional 14-3-3 recognition motif.

Mutant Ssp1 Genes, Such as Ssp-2129 and Ssp-610

In some embodiments, the mutant ssp1 gene comprises, for example, a coding sequence comprising a nucleic acid (e.g., DNA) having the sequence of SEQ ID NO: 2; a coding sequence comprising a portion of SEQ ID NO: 2 that exhibits substantially the same activity (e.g., encoding the same polypeptide or substantially the same polypeptide that has the same activity) as a nucleic acid (e.g., DNA) having the sequence of SEQ ID NO: 2; a coding sequence comprising a nucleic acid (e.g., DNA) having at least 85%, at least 90%, at least 95%, at least 96%, at least 97%, at least 98%, or at least 99% identity with the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); a coding sequence comprising an orthologue or homologue of the nucleic acid having the sequence of SEQ ID NO: 2; an orthologue or homologue of the nucleic acid sequence of positions 631 to 651 of SEQ ID NO: 2; a coding sequence comprising a nucleic acid (e.g., DNA) having the sequence of SEQ ID NO: 3; a coding sequence comprising a portion of SEQ ID NO: 3 that exhibits substantially the same activity (e.g., encoding the same polypeptide or substantially the same polypeptide that has the same activity) as a nucleic acid (e.g., DNA) having the sequence of SEQ ID NO: 3; a coding sequence comprising a nucleic acid (e.g., DNA) having at least 85%, at least 90%, at least 95%, at least 96%, at least 97%, at least 98%, or at least 99% identity with the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); a coding sequence comprising an orthologue or homologue of the nucleic acid having the sequence of SEQ ID NO: 3; or an orthologue or homologue of the nucleic acid sequence of positions 631 to 651 of SEQ ID NO: 3. In some embodiments, the mutant ssp1 gene comprises a C to T mutation at position 641 of SEQ ID NO: 1, a C to T mutation at position 647 of SEQ ID NO: 1, or a C to T mutation at position 641 and position 647 of SEQ ID NO: 1. In some embodiments, the mutant ssp1 gene comprises a nucleotide sequence that encodes a polypeptide of SEQ ID NOs: 5 or 6 or a nucleotide sequence that encodes a polypeptide that comprises SEQ ID NOs: 14 or 15. In some embodiments, the mutant ssp1 gene comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the mutant ssp1 gene comprises a nucleic acid sequence that encodes a mutant ssp1 protein that comprises at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy. In some embodiments, the mutant ssp1 gene comprises, for example, a nucleic acid (e.g., DNA) having the sequence of SEQ ID NO: 25; a portion of SEQ ID NO: 25 that exhibits substantially the same activity (e.g., encoding the same polypeptide or substantially the same polypeptide that has the same activity) as a nucleic acid (e.g., DNA) having the sequence of SEQ ID NO: 25; a nucleic acid (e.g., DNA) having at least 85%, at least 90%, at least 95%, at least 96%, at least 97%, at least 98%, or at least 99% identity with the sequence of SEQ ID NO: 25; an orthologue or homologue of the nucleic acid having the sequence of SEQ ID NO: 25; a nucleic acid (e.g., DNA) having the sequence of SEQ ID NO: 26; a portion of SEQ ID NO: 26 that exhibits substantially the same activity (e.g., encoding the same polypeptide or substantially the same polypeptide that has the same activity) as a nucleic acid (e.g., DNA) having the sequence of SEQ ID NO: 26; a nucleic acid (e.g., DNA) having at least 85%, at least 90%, at least 95%, at least 96%, at least 97%, at least 98%, or at least 99% identity with the sequence of SEQ ID NO: 26; or an orthologue or homologue of the nucleic acid having the sequence of SEQ ID NO: 26.

In some embodiments, the semi-determinate (SD) or semi-indeterminate (SID) Solanaceae plant, e.g., a tomato plant, comprises a mutant ssp1 polypeptide (e.g., a mutant ssp1 protein) encoded by a mutant ssp1 gene. In some embodiments, the mutant ssp1 polypeptide comprises the sequence of SEQ ID NO: 5; a portion of SEQ ID NO: 5 that exhibits substantially the same activity as a polypeptide (e.g., a protein) having the sequence of SEQ ID NO: 5; an amino acid sequence having at least 85%, at least 90%, at least 95%, at least 96%, at least 97%, at least 98%, or at least 99% identity with the sequence of SEQ ID NO: 5; the amino acid sequence of positions 211 to 217 in SEQ ID NO: 5 (RTSTALF, SEQ ID NO: 14); an orthologue or homologue of the polypeptide having the sequence of SEQ ID NO: 5; an orthologue or homologue of the amino acid sequence of positions 211 to 217 in SEQ ID NO: 5 (RTSTALF, SEQ ID NO: 14); a polypeptide (e.g., a protein) having the sequence of SEQ ID NO: 6; a portion of SEQ ID NO: 6 that exhibits substantially the same activity as a polypeptide (e.g., a protein) having the sequence of SEQ ID NO: 6; an amino acid sequence having at least 85%, at least 90%, at least 95%, at least 96%, at least 97%, at least 98%, or at least 99% identity with the sequence of SEQ ID NO: 6; the sequence of positions 211 to 217 in SEQ ID NO: 6 (RTSIAPF, SEQ ID NO: 15); an orthologue or homologue of the polypeptide having the sequence of SEQ ID NO: 6; or an orthologue or homologue of the polypeptide sequence of positions 211 to 217 in SEQ ID NO: 6 (RTSIAPF, SEQ ID NO: 15). In some embodiments, the polypeptide comprises a Thr to Ile mutation at position 214 of SEQ ID NO: 4 or a Pro to Leu mutation at position 216 of SEQ ID NO: 4, or a Thr to Ile mutation at position 214 and a Pro to Leu mutation at position 216 of SEQ ID NO: 4. In some embodiments, the mutant ssp1 polypeptide comprises an amino acid sequence with at least one mutation in a SAP motif, wherein the at least one mutation alters flowering time and shoot architecture of the Solanaceae plant, e.g., by conferring semi-determinacy or semi-indeterminacy. In some embodiments, the SAP motif with the at least one mutation has the amino acid sequence SEQ ID NO: 14 or SEQ ID NO: 15. In some embodiments, the mutant ssp1 polypeptide comprises an amino acid sequence with at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy or semi-indeterminacy.

Mutant Sft Gene, Such as Sft-1906

In some embodiments, the mutant sft gene comprises, for example, a coding sequence comprising a nucleic acid (e.g., DNA) having the sequence of SEQ ID NO: 20; a coding sequence comprising a portion of SEQ ID NO: 20 that exhibits substantially the same activity (e.g., encoding the same polypeptide or substantially the same polypeptide that has the same activity) as a nucleic acid (e.g., DNA) having the sequence of SEQ ID NO: 20; a coding sequence comprising a nucleic acid (e.g., DNA) having at least 85%, at least 90%, at least 95%, at least 96%, at least 97%, at least 98%, or at least 99% identity with the sequence of SEQ ID NO: 20; a coding sequence comprising an orthologue or homologue of the nucleic acid having the sequence of SEQ ID NO:20. In some embodiments, the mutant sft gene comprises a G to A mutation at position 394 of SEQ ID NO: 20. In some embodiments, the mutant sft gene comprises, for example, a nucleic acid (e.g., DNA) having the sequence of SEQ ID NO: 17; a portion of SEQ ID NO: 17 that exhibits substantially the same activity (e.g., encoding the same polypeptide or substantially the same polypeptide that has the same activity) as a nucleic acid (e.g., DNA) having the sequence of SEQ ID NO: 17; a nucleic acid (e.g., DNA) having at least 85%, at least 90%, at least 95%, at least 96%, at least 97%, at least 98%, or at least 99% identity with the sequence of SEQ ID NO: 17; or an orthologue or homologue of the nucleic acid having the sequence of SEQ ID NO: 17. In some embodiments, the mutant sft gene comprises a nucleotide sequence that encodes a mutant sft polypeptide of SEQ ID NO: 21. In some embodiments, the mutant sft gene comprises a nucleotide sequence that encodes a mutant sft polypeptide that comprises a Val to Met mutation at position 132 of SEQ ID NO: 19.

Solanaceae Plants Comprising Mutant Genes

Flowering time and shoot architecture; higher yield, higher quality products (e.g., fruits); and products (e.g., fruits) with different compositions (e.g., brix, also known as enhanced soluble solids or sugar concentration in the fruits), can be manipulated in a wide variety of types of Solanaceae plants that comprise a mutant ssp1 gene or a mutant sft gene, or two or three mutant genes—a mutant ssp1 gene and a mutant self-pruning (sp) gene; a mutant ssp1 and a mutant sft gene; a mutant sft gene and a mutant self-pruning (sp) gene; or a mutant sft gene, a mutant ssp1 gene, and a mutant self-pruning (sp) gene. The mutant ssp1 gene can comprise, for example, any of the ssp1 nucleic acids described herein. The mutant sft gene can comprise, for example, any of the sft nucleic acids described herein. The mutant sp gene can comprise, for example, any of the sp nucleic acids described herein.

In specific embodiments, the mutant ssp1 gene and/or the mutant sft gene is present along with a mutant self-pruning (sp) gene in a double mutant background and the mutant sp gene (Pnueli et al. Development. 1998; 125(11):1979-89) comprises, for example, a coding sequence comprising a nucleic acid (e.g., DNA) having the sequence of SEQ ID NO: 8; a coding sequence comprising a portion of SEQ ID NO: 8 that exhibits substantially the same activity (e.g., encoding the same polypeptide or substantially the same polypeptide that has the same activity) as a nucleic acid (e.g., DNA) having the sequence of SEQ ID NO: 8; a coding sequence comprising a nucleic acid (e.g., DNA) having at least 85%, at least 90%, at least 95%, at least 96%, at least 97%, at least 98%, or at least 99% identity with the sequence of SEQ ID NO: 8; or a coding sequence comprising an orthologue or homologue of the nucleic acid having the sequence of SEQ ID NO: 8. In some embodiments, the mutant sp gene comprises, for example, a nucleic acid (e.g., DNA) having the sequence of SEQ ID NO: 23; a portion of SEQ ID NO: 23 that exhibits substantially the same activity (e.g., encoding the same polypeptide or substantially the same polypeptide that has the same activity) as a nucleic acid (e.g., DNA) having the sequence of SEQ ID NO: 23; a nucleic acid (e.g., DNA) having at least 85%, at least 90%, at least 95%, at least 96%, at least 97%, at least 98%, or at least 99% identity with the sequence of SEQ ID NO: 23; or an orthologue or homologue of the nucleic acid having the sequence of SEQ ID NO: 23. In some embodiments, the mutant sp gene comprises a C to T mutation at position 227 of SEQ ID NO: 7. In some embodiments, the mutant sp gene comprises a nucleotide sequence with at least one mutation that reduces the activity of a sp protein encoded by the mutant sp gene. In some embodiments, the mutant sp gene comprises a nucleotide sequence that encodes a polypeptide of SEQ ID NO: 10. In some embodiments, the SD or SID Solanaceae plant comprises a mutant sp polypeptide (e.g., a protein) encoded by a mutant sp gene. In some embodiments, the mutant sp polypeptide comprises, for example, the sequence of SEQ ID NO: 10; a portion of SEQ ID NO: 10 that exhibits substantially the same activity as a polypeptide (e.g., a protein) having the sequence of SEQ ID NO: 10; an amino acid sequence having at least 85%, at least 90%, at least 95%, at least 96%, at least 97%, at least 98%, or at least 99% identity with the sequence of SEQ ID NO: 10; or an orthologue or homologue of the polypeptide having the sequence of SEQ ID NO: 10. In some embodiments, the mutant sp polypeptide comprises a Pro to Leu mutation at position 76 of SEQ ID NO: 9. In some embodiments, the mutant sp polypeptide comprises at least one mutation that reduces (partially or completely) the activity of the sp polypeptide. In some embodiments, the mutant sp polypeptide comprises at least one mutation that reduces the activity of the sp polypeptide, wherein the reduced (partially or completely) activity of the sp polypeptide can confer determinacy.

The Solanaceae plant can be, for example, inbred, isogenic or hybrid, as long as the plant comprises a mutant ssp1 gene, a mutant sft gene, a mutant ssp1 gene and a mutant sft gene, a mutant sft gene and a mutant sp gene, a mutant ssp1 gene and a mutant sp gene, or a mutant ssp1 gene, a mutant sft gene, and a mutant sp gene. Plants in the Solanaceae family include, e.g., tomato, potato, eggplant, petunia, tobacco, and pepper. In some embodiments, the Solanaceae plant is a tomato plant. In some embodiments, the Solanaceae plant, e.g. tomato plant, is not a variety.

In some embodiments, the Solanaceae plant comprises one wild-type copy of the SSP1 gene and one mutant copy of the ssp1 gene as described herein (is heterozygous for the mutant ssp1 gene). In some embodiments, the Solanaceae plant comprises two copies of a mutant ssp1 gene as described herein (is homozygous for the mutant ssp1 gene). In some embodiments, the Solanaceae plant comprises a first mutant ssp1 gene as described herein and a second mutant ssp1 gene as described herein, wherein the first mutant ssp1 gene and the second mutant ssp1 gene are different (e.g., the first mutant ssp1 gene comprises a coding sequence comprising SEQ ID NO: 2 and the second mutant ssp1 gene comprises a coding sequence comprising SEQ ID NO: 3). In some embodiments, the Solanaceae plant comprises one copy of a mutant ssp1 gene as described herein and one copy of a mutant sp gene as described herein (is heterozygous for the mutant ssp1 gene and heterozygous for the mutant sp gene). In some embodiments, the Solanaceae plant comprises one copy of a mutant ssp1 gene as described herein and two copies of a mutant sp gene as described herein (is heterozygous for the mutant ssp1 gene and homozygous for the mutant sp gene). In some embodiments, the Solanaceae plant comprises two copies of a mutant ssp1 gene as described herein and two copies of a mutant sp gene as described herein (is homozygous for the mutant ssp1 gene and homozygous for the mutant sp gene).

In some embodiments, the Solanaceae plant comprises one wild-type copy of a SFT gene and one mutant copy of a sft gene as described herein (is heterozygous for the mutant sft gene). In some embodiments, the Solanaceae plant comprises two copies of a mutant sft gene as described herein (is homozygous for the mutant sft gene). In some embodiments, the Solanaceae plant comprises one copy of a mutant sft gene as described herein and one copy of a mutant sp gene as described herein (is heterozygous for the mutant sft gene and heterozygous for the mutant sp gene). In some embodiments, the Solanaceae plant comprises one copy of a mutant sft gene as described herein and two copies of a mutant sp gene as described herein (is heterozygous for the mutant sft gene and homozygous for the mutant sp gene). In some embodiments, the Solanaceae plant comprises two copies of a mutant sft gene as described herein and two copies of a mutant sp gene as described herein (is homozygous for the mutant sft gene and homozygous for the mutant sp gene).

In some embodiments, the Solanaceae plant comprises one wild-type copy of a SFT gene and one mutant copy of a sft gene as described herein (is heterozygous for the mutant sft gene) and comprises one wild-type copy of the SSP1 gene and one mutant copy of the ssp1 gene as described herein (is heterozygous for the mutant ssp1 gene). In some embodiments, the Solanaceae plant comprises two copies of a mutant sft gene as described herein (is homozygous for the mutant sft gene) and comprises two copies of a mutant ssp1 gene as described herein (is homozygous for the mutant ssp1gene). In some embodiments, the Solanaceae plant comprising a mutant sft gene (one or two copies) as described herein and a mutant ssp1 gene (one or two copies) further comprises one copy of a mutant sp gene as described herein (is heterozygous or homozygous for the mutant sft gene and the mutant ssp1 gene and heterozygous for the mutant sp gene). In some embodiments, the Solanaceae plant further comprises two copies of a mutant sp gene as described herein (is homozygous for the mutant sp gene). Exemplary, non-limiting genotype combinations include:

| Combination # | SSP1 genotype | SFT genotype | SP genotype |
|---|---|---|---|
| 1 | ssp-2129/+ | +/+ | sp/sp |
| 2 | ssp-610/+ | +/+ | sp/sp |
| 3 | +/+ | sft-1906/+ | sp/sp |
| 4 | ssp-2129/+ | sft-1906/+ | sp/sp |
| 5 | ssp-610/+ | sft-1906/+ | sp/sp |
| 6 | ssp-2129/ssp-2129 | +/+ | sp/sp |
| 7 | ssp-610/ssp-610 | +/+ | sp/sp |
| 8 | ssp-2129/ssp-610 | +/+ | sp/sp |
| 9 | +/+ | sft-1906/sft-1906 | sp/sp |

In some embodiments, a genetically-altered Solanaceae plant (e.g., a tomato plant) provided herein is semi-determinate or semi-indeterminate. As used herein, a Solanaceae plant that is "semi-determinate" is a plant that (1) has a sympodial index that is less than 3 and (2) undergoes termination of the sympodial meristem. As used herein, a Solanaceae plant that is "semi-indeterminate" is a plant that (1) has a sympodial index that is less than 3 and (2) continuously produces sympodial shoots (the sympodial meristem does not undergo termination). The term "sympodial index", as used herein, refers to the number of leaves per sympodium (i.e., the number of leaves between successive clusters of flowers). In some embodiments, the genetically-altered Solanaceae plant has a sympodial index of less than 3, less than 2.9, less than 2.8, less than 2.7, less than 2.6, less than 2.5, less than 2.4, less than 2.3, less than 2.2, less than 2.1, less than 2, less than 1.9, less than 1.8, less than 1.7, less than 1.6, or less than 1.5. In some embodiments, the genetically-altered Solanaceae plant has a sympodial index of between 1 and 3, 1.5 and 3, 1 and 2.5, 1.5 and 2.5, 1 and 2, or 1.5 and 2.

Solanaceae plant cells are also contemplated herein. A Solanaceae plant cell may comprise any genotype described herein in the context of the Solanaceae plant (e.g., a Solanaceae plant cell heterozygous for a mutant sft gene and a mutant ssp1 gene or a Solanaceae plant cell homozygous for a mutant ssp1 gene and a mutant sp gene). In some embodiments, the Solanaceae plant cell is isolated. In some embodiments, the Solanaceae plant cell is a non-replicating plant cell.

In some embodiments, any of the Solanaceae plants described above have an altered flowering time and shoot architecture compared to a wild-type Solanaceae plant (e.g., a Solanaceae plant comprising two copies of a wild-type SP gene), to a determinate Solanaceae plant (e.g., a Solanaceae plant comprising a mutant sp gene), or to both a wild-type Solanaceae plant and a determinate Solanaceae plant. In some embodiments, any of the Solanaceae plants described above have a higher yield than a corresponding wild-type Solanaceae plant. In some embodiments, a Solanaceae plant comprising two copies of a mutant ssp1 gene as described herein and two copies of a wild-type SP gene as described herein has altered flowering time compared to a wild-type Solanaceae plant. In some embodiments, a Solanaceae plant comprising one copy of a mutant ssp1 gene as described herein and two copies of a mutant sp gene as described herein is semi-determinate or semi-indeterminate. In some embodiments, a Solanaceae plant comprising two copies of a mutant ssp1 gene as described herein and two copies of a mutant sp gene as described herein is semi-determinate or semi-indeterminate.

Food products are also contemplated herein. Such food products comprise a Solanaceae plant part, such as a fruit (e.g., a tomato fruit). Non-limiting examples of food products include sauces (e.g., tomato sauce or ketchup), purees, pastes, juices, canned fruits, and soups. Food products may be produced or producible by using methods known in the art.

Isolated polynucleotides are also described herein, including wild-type and mutant alleles of the SSP1 gene, and specifically, two mutant alleles designated herein as ssp-2129 and ssp-610. Isolated polynucleotides including wild-type and mutant alleles of the SFT gene are also contemplated, e.g., sft-1906. Isolated polynucleotides can comprise, for example, a nucleic acid (e.g., DNA) having the sequence of SEQ ID NO: 2; a portion of SEQ ID NO: 2 that exhibits substantially the same activity as a nucleic acid (e.g., DNA) having the sequence of SEQ ID NO: 2; a nucleic acid (e.g., DNA) having at least 85%, at least 90%, at least 95%, at least 96%, at least 97%, at least 98%, or at least 99% identity with the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); an orthologue or homologue of the nucleic acid having the sequence of SEQ ID NO: 2; an orthologue or homologue of the nucleic acid sequence of positions 631 to 651 of SEQ ID NO: 2; a nucleic acid (e.g., DNA) having the sequence of SEQ ID NO: 3; a portion of SEQ ID NO: 3 that exhibits substantially the same activity as a nucleic acid (e.g., DNA) having the sequence of SEQ ID NO: 3; a nucleic acid (e.g., DNA) having at least 85%, at least 90%, at least 95%, at least 96%, at least 97%, at least 98%, or at least 99% identity with the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); an orthologue or homologue of the nucleic acid having the sequence of SEQ ID NO: 3; or an orthologue or homologue of the nucleic acid sequence of positions 631 to 651 of SEQ ID NO: 3. In some embodiments, the isolated polynucleotide comprises a mutant ssp1 gene that includes a C to T mutation at position 641 of SEQ ID NO: 1, a C to T mutation at position 647 of SEQ ID NO: 1, or a C to T mutation at position 641 and position 647 of SEQ ID NO: 1. In some embodiments, the isolated polynucleotide comprises a nucleotide sequence that encodes the polypeptide of SEQ ID NOs: 5 or 6 or a nucleotide sequence that encodes a polypeptide that comprises SEQ ID NOs: 14 or 15. In some embodiments, the isolated polynucleotide comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the isolated polynucleotide comprises a nucleic acid sequence that encodes a mutant ssp1 protein that comprises at least one mutation in the SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy. In some embodiments, isolated polynucleotides can comprise, for example, a nucleic acid (e.g., DNA) having the sequence of SEQ ID NO: 20; a portion of SEQ ID NO: 20 that exhibits substantially the same activity as a nucleic acid (e.g., DNA) having the sequence of SEQ ID NO: 20; a nucleic acid (e.g., DNA) having at least 70%, at least 80%, at least 90%, at least 95%, at least 96%, at least 97%, at least 98%, or at least 99% identity with the sequence of SEQ ID NO: 20; or an orthologue or homologue of the nucleic acid having the sequence of SEQ ID NO: 20. In some embodiments, the isolated polynucleotide comprises a mutant sft gene comprising a G to A mutation at position 394 of SEQ ID NO: 20. In some embodiments, the isolated polynucleotide comprising a mutant sft gene comprises a nucleotide sequence that encodes a polypeptide of SEQ ID NO: 21. In some embodiments, the isolated polynucleotide comprises a mutant sft gene comprising a nucleotide sequence that encodes a mutant sft polypeptide that comprises a Val to Met mutation at position 132 of SEQ ID NO: 19. In some embodiments, the isolated polynucleotide is a cDNA. Such isolated polynucleotides can be used, for example, in methods of producing genetically-altered plants, such as genetically-altered semi-determinate or semi-indeterminate plants.

Isolated polypeptides (e.g., proteins) are also described herein, including wild-type and mutant ssp1 polypeptides, and specifically, the polypeptides encoded by the two mutant alleles ssp-2129 and ssp-610. Isolated polypeptides also include wild-type and mutant sft polypeptides, such as those encoded by the mutant allele sft-1906. In some embodiments, the isolated polypeptide comprises, for example, the sequence of SEQ ID NO: 5; a portion of SEQ ID NO: 5 that exhibits substantially the same activity as a polypeptide (e.g., a protein) having the sequence of SEQ ID NO: 5; an amino acid sequence having at least 85%, at least 90%, at least 95%, at least 96%, at least 97%, at least 98%, or at least 99% identity with the sequence of SEQ ID NO: 5; the amino acid sequence of positions 211 to 217 in SEQ ID NO: 5 (RTSTALF, SEQ ID NO: 14); an orthologue or homologue of the polypeptide having the sequence of SEQ ID NO: 5; an orthologue or homologue of the amino acid sequence of positions 211 to 217 in SEQ ID NO: 5 (RTSTALF, SEQ ID NO: 14); a polypeptide (e.g., a protein) having the sequence of SEQ ID NO: 6; a portion of SEQ ID NO: 6 that exhibits substantially the same activity as a polypeptide (e.g., a protein) having the sequence of SEQ ID NO: 6; an amino acid sequence having at least 85%, at least 90%, at least 95%, at least 96%, at least 97%, at least 98%, or at least 99% identity with the sequence of SEQ ID NO: 6; the sequence of positions 211 to 217 in SEQ ID NO: 6 (RTSIAPF, SEQ ID NO: 15); an orthologue or homologue of the polypeptide having the sequence of SEQ ID NO: 6; or an orthologue or homologue of the polypeptide sequence of positions 211 to 217 in SEQ ID NO: 6 (RTSIAPF, SEQ ID NO: 15). In some embodiments, the isolated polypeptide comprises a Thr to Ile mutation at position 214 of SEQ ID NO: 4 or a Pro to Leu mutation at position 216 of SEQ ID NO: 4, or a Thr to Ile mutation at position 214 and a Pro to Leu mutation at position 216 of SEQ ID NO: 4. In some embodiments, the isolated polypeptide comprises a mutant ssp1 protein comprising an amino acid sequence with at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the isolated polypeptide comprises a mutant ssp1 protein comprising an amino acid sequence with at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy. An isolated polypeptide may also comprise the sequence of SEQ ID NO: 21; a portion of SEQ ID NO: 21 that exhibits substantially the same activity as a polypeptide (e.g., a protein) having the sequence of SEQ ID NO: 21; an amino acid sequence having at least 85%, at least 90%, at least 95%, at least 96%, at least 97%, at least 98%, or at least 99% identity with the sequence of SEQ ID NO: 21; an orthologue or homologue of the polypeptide having the sequence of SEQ ID NO: 21. Such isolated polypeptides can be used, for example, in methods of producing genetically-altered plants, such as genetically-altered semi-determinate or semi-indeterminate plants.

Figure 2:
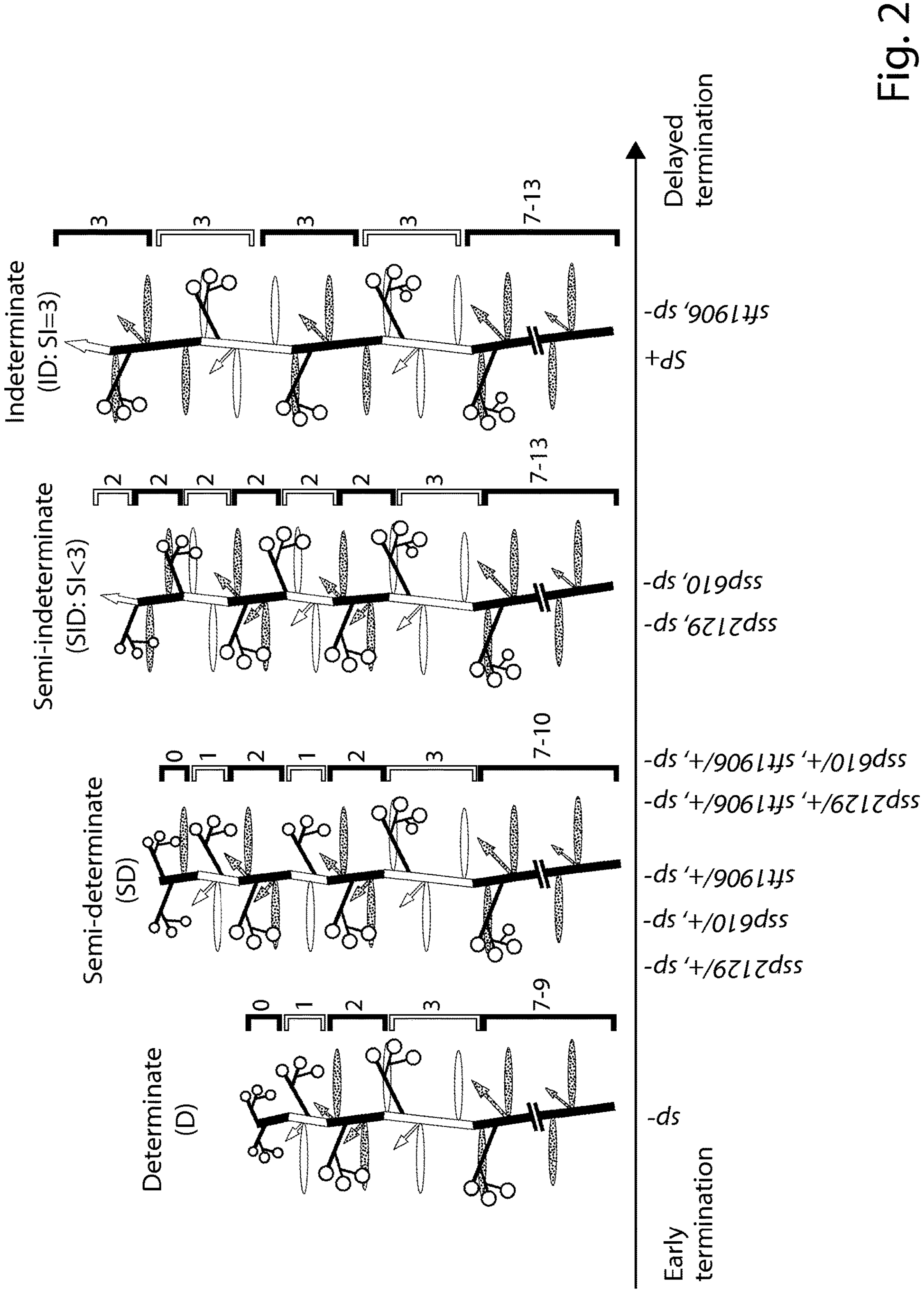
FIG. 2 shows graphical representations of the suppression of sp mutant imposed sympodial shoot termination with the ssp1 and sft mutants in the sp mutant background. Left depicts a sp "Determinate" (D) mutant plant. Right depicts the wild-type "Indeterminate" (ID) plant with fully functional SP, SSP1 and SFT genes. Note the three-leaf reiteration of vegetative sympodial shoots (SYM) after the primary shoot produces 7-9 leaves and transitions to flowering. The number of leaves in each sympodial unit, known as the Sympodial Index (SI) is consistently three. The second diagram from left depicts the "Semi-determinate" (SD) single heterozygote plants of ssp-2129, ssp610 or sft1906, and double heterozygote plants of ssp-2129, ssp610 or sft1906 in the sp mutant background. Note that shoot growth ends after a few more units of vegetative shoot (SYM) production compared to the sp determinate plants. Right middle depicts the "semi-indeterminate" ssp-2129; sp double mutant plant. Note the reduction in leaf number from three to two in each SYM (SI=2). Dots indicate flowers/fruits produced in each inflorescence. Black and gray arrows indicate axillary shoots on the leaf axils. The long horizontal arrow indicates the gradual change in determinacy due to individual and combined mutations in homozygous and heterozygous conditions.

Also described herein are methods of modifying flowering time and shoot architecture in a Solanaceae plant, such as tomato, particularly suppressing sympodial shoot termination, which results in increased number of leaves in a Solanaceae plant compared to the number of leaves in corresponding determinate (e.g., a sp mutant) plants maintained under the same conditions, but fewer leaves than the number of leaves in corresponding indeterminate wild-type plants (see, e.g., FIGS. 2 and 4).

Methods described are methods of producing a genetically-altered Solanaceae plant, such as a semi-determinate (SD) or semi-indeterminate (SID) plant; and/or a Solanaceae plant with an altered flowering time and shoot architecture, increased yield, higher quality products (e.g., fruits), and/or products (e.g., fruits) with different compositions (e.g., brix, also known as enhanced soluble solids or sugar concentration in the fruits) compared to a wild-type Solanaceae plant. In one embodiment, a method of producing a genetically-altered semi-determinate or semi-indeterminate Solanaceae plant comprises: (a) introducing a mutant ssp1 gene into a Solanaceae plant that comprises a mutant sp gene or producing a mutant ssp1 gene in a Solanaceae plant that comprises a mutant sp gene, thereby producing a genetically-altered plant that comprises the mutant ssp1 gene and the mutant sp gene; (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and homozygous for the mutant sp gene, thereby producing a genetically-altered Solanaceae plant that is homozygous for the mutant ssp1 gene and the mutant sp gene and is semi-determinate or semi-indeterminate. In another embodiment, a method of producing a genetically-altered Solanaceae plant with an altered flowering time and shoot architecture compared to a wild-type Solanaceae plant comprises: (a) introducing a mutant ssp1 gene into a Solanaceae plant that comprises a mutant sp gene or producing a mutant ssp1 gene in a Solanaceae plant that comprises a mutant sp gene, thereby producing a genetically-altered plant that comprises the mutant ssp1 gene and the mutant sp gene; (b) self-crossing the genetically-altered Solanaceae plant produced in (a) or crossing two genetically-altered Solanaceae plants produced in (a) under conditions appropriate for producing a genetically-altered Solanaceae plant heterozygous for the mutant ssp1 gene and homozygous for the mutant sp gene, thereby producing a genetically-altered Solanaceae plant that is heterozygous for the mutant ssp1 gene and homozygous for the mutant sp gene and has an altered flowering time and shoot architecture compared to a wild-type Solanaceae plant.

In other embodiments, the method comprises:

(a) introducing a mutant sft gene into a Solanaceae plant containing a mutant ssp1 gene or introducing a mutant ssp1 gene into a Solanaceae plant containing a mutant sft gene, thereby producing a genetically-altered Solanaceae plant containing a mutant sft gene and a mutant ssp1 gene; and (b) self-crossing the genetically-altered Solanaceae plant produced in (a) or crossing two genetically-altered Solanaceae plants produced in (a) under conditions appropriate for producing a genetically-altered Solanaceae plant heterozygous or homozygous for the mutant sft gene and heterozygous or homozygous for the mutant ssp1 gene. In some embodiments, the plant produced in (b) is heterozygous for the mutant sft gene and heterozygous for the mutant ssp1 gene.

In specific embodiments of the method, the mutant ssp1 gene comprises, for example, a coding sequence comprising a nucleic acid (e.g., DNA) having the sequence of SEQ ID NO: 2; a coding sequence comprising a portion of SEQ ID NO: 2 that exhibits substantially the same activity (e.g., encoding the same polypeptide or substantially the same polypeptide that has the same activity) as a nucleic acid (e.g., DNA) having the sequence of SEQ ID NO: 2; a coding sequence comprising a nucleic acid (e.g., DNA) having at least 85%, at least 90%, at least 95%, at least 96%, at least 97%, at least 98%, or at least 99% identity with the sequence of SEQ ID NO: 2; a nucleic acid (e.g., DNA) having the sequence of positions 631 to 651 of SEQ ID NO: 2 (CGGACGTCAACTGCTCTATTT, SEQ ID NO: 12); a coding sequence comprising an orthologue or homologue of the nucleic acid having the sequence of SEQ ID NO: 2; an orthologue or homologue of the nucleic acid sequence of positions 631 to 651 of SEQ ID NO: 2; a coding sequence comprising a nucleic acid (e.g., DNA) having the sequence of SEQ ID NO: 3; a coding sequence comprising a portion of SEQ ID NO: 3 that exhibits substantially the same activity (e.g., encoding the same polypeptide or substantially the same polypeptide that has the same activity) as a nucleic acid (e.g., DNA) having the sequence of SEQ ID NO: 3; a coding sequence comprising a nucleic acid (e.g., DNA) having at least 85%, at least 90%, at least 95%, at least 96%, at least 97%, at least 98%, or at least 99% identity with the sequence of SEQ ID NO: 3; a nucleic acid (e.g., DNA) having the sequence of positions 631 to 651 of SEQ ID NO: 3 (CGGACGTCAATTGCTCCATTT, SEQ ID NO: 13); a coding sequence comprising an orthologue or homologue of the nucleic acid having the sequence of SEQ ID NO: 3; or an orthologue or homologue of the nucleic acid sequence of positions 631 to 651 of SEQ ID NO: 3. In some embodiments, the mutant ssp1 gene comprises, for example, a nucleic acid (e.g., DNA) having the sequence of SEQ ID NO: 25; a portion of SEQ ID NO: 25 that exhibits substantially the same activity (e.g., encoding the same polypeptide or substantially the same polypeptide that has the same activity) as a nucleic acid (e.g., DNA) having the sequence of SEQ ID NO: 25; a nucleic acid (e.g., DNA) having at least 85%, at least 90%, at least 95%, at least 96%, at least 97%, at least 98%, or at least 99% identity with the sequence of SEQ ID NO: 25; an orthologue or homologue of the nucleic acid having the sequence of SEQ ID NO: 25; a nucleic acid (e.g., DNA) having the sequence of SEQ ID NO: 26; a portion of SEQ ID NO: 26 that exhibits substantially the same activity (e.g., encoding the same polypeptide or substantially the same polypeptide that has the same activity) as a nucleic acid (e.g., DNA) having the sequence of SEQ ID NO: 26; a nucleic acid (e.g., DNA) having at least 85%, at least 90%, at least 95%, at least 96%, at least 97%, at least 98%, or at least 99% identity with the sequence of SEQ ID NO: 26; or an orthologue or homologue of the nucleic acid having the sequence of SEQ ID NO: 26. In some embodiments, the mutant ssp1 gene comprises a C to T mutation at position 641 of SEQ ID NO: 1, a C to T mutation at position 647 of SEQ ID NO: 1, or a C to T mutation at position 641 and position 647 of SEQ ID NO: 1. In some embodiments, the mutant ssp1 gene comprises a nucleotide sequence that encodes a polypeptide of SEQ ID NOs: 5 or 6 or a nucleotide sequence that encodes a polypeptide that comprises SEQ ID NOs: 14 or 15. In some embodiments, the mutant ssp1 gene comprises a nucleic acid sequence that encodes a mutant ssp1 protein that comprises at least one mutation in a SAP motif, wherein the at least one mutation alters flowering time and shoot architecture of the Solanaceae plant, e.g., by conferring semi-determinacy. In some embodiments, the SAP motif with the at least one mutation has the amino acid sequence SEQ ID NO: 14 or SEQ ID NO: 15. In some embodiments, the mutant ssp1 gene comprises a nucleic acid sequence that encodes a mutant ssp1 protein that comprises at least one mutation in a SAP motif or in the two amino acids flanking the N-terminal position of the SAP motif and the one amino acid flanking the C-terminal position of the SAP motif, which includes the phosphorylation site for Ca-dependent protein kinases (CDPKs), wherein the at least one mutation alters flowering time and shoot architecture of the Solanaceae plant, e.g., by conferring semi-determinacy.

In some embodiments, the mutant sft gene comprises, for example, a coding sequence comprising a nucleic acid (e.g., DNA) having the sequence of SEQ ID NO: 20; a coding sequence comprising a portion of SEQ ID NO: 20 that exhibits substantially the same activity (e.g., encoding the same polypeptide or substantially the same polypeptide that has the same activity) as a nucleic acid (e.g., DNA) having the sequence of SEQ ID NO: 20; a coding sequence comprising a nucleic acid (e.g., DNA) having at least 85%, at least 90%, at least 95%, at least 96%, at least 97%, at least 98%, or at least 99% identity with the sequence of SEQ ID NO: 20; or a coding sequence comprising an orthologue or homologue of the nucleic acid having the sequence of SEQ ID NO:20. In some embodiments, the mutant sft gene comprises a G to A mutation at position 394 of SEQ ID NO: 20. In some embodiments, the mutant sft gene comprises a nucleotide sequence that encodes a polypeptide of SEQ ID NO: 21. In some embodiments, the mutant sft gene comprises a nucleotide sequence that encodes a mutant sft polypeptide comprising a Val to Met mutation at position 132 of SEQ ID NO: 19. In some embodiments, the mutant sft gene comprises, for example, a nucleic acid (e.g., DNA) having the sequence of SEQ ID NO: 17; a portion of SEQ ID NO: 17 that exhibits substantially the same activity (e.g., encoding the same polypeptide or substantially the same polypeptide that has the same activity) as a nucleic acid (e.g., DNA) having the sequence of SEQ ID NO: 17; a nucleic acid (e.g., DNA) having at least 85%, at least 90%, at least 95%, at least 96%, at least 97%, at least 98%, or at least 99% identity with the sequence of SEQ ID NO: 17; or an orthologue or homologue of the nucleic acid having the sequence of SEQ ID NO: 17.

In specific embodiments, the sp mutant gene comprises, for example, a coding sequence comprising a nucleic acid (e.g., DNA) having the sequence of SEQ ID NO: 8; a coding sequence comprising a portion of SEQ ID NO: 8 that exhibits substantially the same activity (e.g., encoding the same polypeptide or substantially the same polypeptide that has the same activity) as a nucleic acid (e.g., DNA) having the sequence of SEQ ID NO: 8; a coding sequence comprising a nucleic acid (e.g., DNA) having at least 85%, at least 90%, at least 95%, at least 96%, at least 97%, at least 98%, or at least 99% identity with the sequence of SEQ ID NO: 8; or a coding sequence comprising an orthologue or homologue of the nucleic acid having the sequence of SEQ ID NO: 8. In some embodiments, the mutant sp gene comprises a C to T mutation at position 227 of SEQ ID NO: 7. In some embodiments, the mutant sp gene comprises at least one mutation that reduces the activity of a sp protein encoded by the mutant sp gene. In some embodiments, the mutant sp gene comprises at least one mutation that reduces (partially or completely) the activity of a sp protein encoded by the mutant sp gene, wherein the reduced activity can confer determinacy. In some embodiments, the mutant sp gene comprises a nucleotide sequence that encodes a polypeptide of SEQ ID NO: 10. In some embodiments, the mutant sp gene comprises, for example, a nucleic acid (e.g., DNA) having the sequence of SEQ ID NO: 23; a portion of SEQ ID NO: 23 that exhibits substantially the same activity (e.g., encoding the same polypeptide or substantially the same polypeptide that has the same activity) as a nucleic acid (e.g., DNA) having the sequence of SEQ ID NO: 23; a nucleic acid (e.g., DNA) having at least 85%, at least 90%, at least 95%, at least 96%, at least 97%, at least 98%, or at least 99% identity with the sequence of SEQ ID NO: 23; or an orthologue or homologue of the nucleic acid having the sequence of SEQ ID NO: 23.

Alternatively, a method of producing a genetically-altered Solanaceae plant, such as a genetically-altered semi-determinate or semi-indeterminate Solanaceae plant, comprises: (a) introducing a mutant ssp1 gene into a Solanaceae plant part (e.g., a cell, a leaf or seed) that comprises a mutant sp gene or producing a mutant ssp1 gene in a Solanaceae plant part (e.g., a cell, a leaf or seed) that comprises a mutant sp gene, thereby producing a genetically-altered Solanaceae plant part that contains the mutant ssp1 gene and the mutant sp gene; (b) maintaining the genetically-altered Solanaceae plant part containing the mutant ssp1 gene produced in (a) under conditions and for sufficient time for production of a genetically-altered Solanaceae plant containing the mutant ssp1 gene and the mutant sp gene from the plant part, thereby producing a genetically-altered Solanaceae plant that contains the mutant ssp1 gene and a mutant sp gene; (c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sp gene, thereby producing a genetically-altered Solanaceae plant that is homozygous for the mutant ssp1 gene and the mutant sp gene and is semi-determinate or semi-indeterminate. In another embodiment, a method of producing a genetically-altered Solanaceae plant with an altered flowering time and shoot architecture compared to a wild-type Solanaceae plant comprises: (a) introducing a mutant ssp1 gene into a Solanaceae plant part (e.g., a cell, a leaf or seed) that comprises a mutant sp gene or producing a mutant ssp1 gene in a Solanaceae plant part (e.g., a cell, a leaf or seed) that comprises a mutant sp gene, thereby producing a genetically-altered Solanaceae plant part that contains the mutant ssp1 gene and the mutant sp gene; (b) maintaining the genetically-altered Solanaceae plant part containing the mutant ssp1 gene produced in (a) under conditions and for sufficient time for production of a genetically-altered Solanaceae plant containing the mutant ssp1 gene and the mutant sp gene from the plant part, thereby producing a genetically-altered Solanaceae plant that contains the mutant ssp1 gene and a mutant sp gene; (c) self-crossing the genetically-altered Solanaceae plant produced in (b) or crossing two genetically-altered Solanaceae plants produced in (b) under conditions appropriate for producing a genetically-altered Solanaceae plant heterozygous for the mutant ssp1 gene and homozygous for the mutant sp gene, thereby producing a genetically-altered Solanaceae plant that is heterozygous for the mutant ssp1 gene and homozygous for the sp gene and has an altered flowering time and shoot architecture compared to a wild-type Solanaceae plant. The mutant ssp1 gene and the mutant sp gene can be as described above.

In some embodiments, the method of producing a genetically-altered Solanaceae plant comprises:

(a) introducing a mutant sft gene into a Solanaceae plant part containing a mutant ssp1 gene or introducing a mutant ssp1 gene into a Solanaceae plant part containing a mutant sft gene, thereby producing a genetically-altered Solanaceae plant part containing the mutant sft gene and the mutant ssp1 gene;

(b) maintaining the genetically-altered Solanaceae plant part containing a mutant sft gene and a mutant ssp1 gene produced in (a) under conditions and for sufficient time for production of a genetically-altered Solanaceae plant containing the mutant sft gene and the mutant ssp1 gene from the plant part, thereby producing a genetically-altered Solanaceae plant containing the mutant sft gene and the mutant ssp1 gene; and (c) self-crossing the genetically-altered Solanaceae plant produced in (b) or crossing two genetically-altered Solanaceae plants produced in (b) under conditions appropriate for producing a genetically-altered Solanaceae plant heterozygous or homozygous for the mutant sft gene and heterozygous or homozygous for the mutant ssp1 gene, thereby producing a genetically-altered Solanaceae plant. In some embodiments, the plant produced in (c) is heterozygous for the mutant sft gene and heterozygous for the mutant ssp1gene.

In any of the methods described herein, the mutant ssp1 gene or the mutant sft gene can be introduced into a Solanaceae plant or a plant part or produced in a Solanaceae plant or plant part by a method known to those of skill in the art, such as *Agrobacterium*-mediated recombination, viral-vector mediated recombination, microinjection, gene gun bombardment/biolistic particle delivery, electroporation, mutagenesis (e.g., by ethyl methanesulfonate or fast neutron irradiation), TILLING (Targeting Induced Local Lesions in Genomes), conventional marker-assisted introgression, and nuclease mediated recombination (e.g., use of custom-made restriction enzymes for targeting mutagenesis by gene replacement, see, e.g., CRISPR-Cas9: Genome engineering using the CRISPR-Cas9 system. Ran F A, Hsu P D, Wright J, Agarwala V, Scott D A, Zhang F. Nat Protoc. 2013 November; 8(11):2281-308; TALEN endonucleases: Nucleic Acids Res. 2011 July; 39(12):e82. Efficient design and assembly of custom TALEN and other TAL effector-based constructs for DNA targeting. Cermak T, Doyle E L, Christian M, Wang L, Zhang Y, Schmidt C, Baller J A, Somia N V, Bogdanove A J, Voytas D F and Plant Biotechnol J. 2012 May; 10(4):373-89. Genome modifications in plant cells by custom-made restriction enzymes. Tzfira T, Weinthal D, Marton I, Zeevi V, Zuker A, Vainstein A.). Genetically-altered Solanaceae plants, such as genetically-altered semi-determinate or semi-indeterminate Solanaceae plants, produced by or producible by a method described herein are also claimed.

Alternatively, a method of producing a semi-determinate or semi-indeterminate Solanaceae plant or a Solanaceae plant having one or more other characteristics described herein (increased yield, brix, etc.) comprises: (a) reducing (partially or completely) function of a wild-type SSP1 gene comprising SEQ ID NO: 1 in a Solanaceae plant homozygous for a mutant sp gene, thereby producing a semi-determinate or semi-indeterminate Solanaceae plant. In some embodiments, reducing the function of the wild-type SSP1 gene comprising SEQ ID NO: 1 comprises performing any of the following methods of RNA-interference (e.g., administering to the Solanaceae plant a micro-RNA or a small interfering (si)-RNA or hairpin RNA) or translational blocking (e.g., administering to the Solanaceae plant a morpholino). Methods of RNA-interference and translational blocking are well-known in the art. Methods of producing micro-RNAs, si-RNAs, and morpholinos are well-known in the art and can involve use of the nucleotides sequences provided herein, e.g., SEQ ID NO: 1. The mutant sp gene can be any mutant sp gene described herein. In some embodiments, the method further comprises (b) reducing (partially or completely) function of a wild-type SFT gene comprising SEQ ID NO: 16 or a coding sequence comprising SEQ ID NO: 18. In some embodiments, reducing the function of the wild-type SFT gene comprises performing any of the above methods of RNA-interference or translational blocking.

Further aspects and embodiments of the disclosure are provided below.

In some embodiments, the disclosure provides a genetically-altered Solanaceae plant comprising a mutant suppressor of sp1 (ssp1) gene and a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant sp gene encodes a mutant sp polypeptide comprising the sequence of SEQ ID NO: 10. In some embodiments, the mutant sp gene comprises a coding sequence having the nucleic acid sequence of SEQ ID NO: 8. In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered Solanaceae plant is homozygous for the mutant ssp1 gene and homozygous for the mutant sp gene. In some embodiments, the genetically-altered Solanaceae plant is semi-determinate.

Other aspects relate to a seed for producing a genetically-altered Solanaceae plant as described in any of the embodiments provided in the preceding paragraph.

Yet other aspects relate to a method of producing a genetically-altered Solanaceae plant comprising:

(a) introducing a mutant ssp1 gene into a Solanaceae plant containing a mutant sp gene, thereby producing a genetically-altered Solanaceae plant containing a mutant ssp1 gene and a mutant sp gene; and (b) self-crossing the genetically-altered Solanaceae plant produced in (a) or crossing two genetically-altered Solanaceae plants produced in (a) under conditions appropriate for producing a genetically-altered Solanaceae plant heterozygous or homozygous for the mutant ssp1 gene and heterozygous or homozygous for the mutant sp gene, thereby producing a genetically-altered Solanaceae plant. In some embodiments, the method of producing a genetically-altered Solanaceae plant comprises:

(a) introducing a mutant ssp1 gene into a Solanaceae plant part containing a mutant sp gene, thereby producing a genetically-altered Solanaceae plant part containing the mutant ssp1 gene and the mutant sp gene;

(b) maintaining the genetically-altered Solanaceae plant part containing a mutant ssp1 and a mutant sp gene produced in (a) under conditions and for sufficient time for production of a genetically-altered Solanaceae plant containing the mutant ssp1 gene and the mutant sp gene from the plant part, thereby producing a genetically-altered Solanaceae plant containing the mutant ssp1 gene and the mutant sp gene;

(c) self-crossing the genetically-altered Solanaceae plant produced in (b) or crossing two genetically-altered Solanaceae plants produced in (b) under conditions appropriate for producing a genetically-altered Solanaceae plant heterozygous or homozygous for the mutant ssp1 gene and heterozygous or homozygous for the mutant sp gene, thereby producing a genetically-altered Solanaceae plant. In some embodiments, the genetically-altered Solanaceae plant is homozygous for the mutant ssp1 gene and homozygous for the mutant sp gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15 In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant sp gene encodes a mutant sp polypeptide comprising the sequence of SEQ ID NO: 10. In some embodiments, the mutant sp gene comprises a coding sequence having the nucleic acid sequence of SEQ ID NO: 8. In some embodiments, in (a), the mutant ssp1 gene is introduced into a plant or a plant part by a method selected from the group consisting of: *Agrobacterium*-mediated recombination, viral-vector mediated recombination, microinjection, gene gun bombardment/biolistic particle delivery, nuclease mediated recombination, and electroporation. In some embodiments, in (a), the mutant ssp1 gene is introduced into a plant or a plant part by nuclease mediated recombination. In some embodiments, the genetically-altered Solanaceae plant is a tomato (*Solanum lycopersicum*) plant. In some embodiments, the genetically-altered Solanaceae plant is inbred. In some embodiments, the genetically-altered Solanaceae plant is semi-determinate.

Another aspect relates to a genetically-altered Solanaceae plant produced by the method of any of the embodiments provided in the preceding paragraph.

Other aspects relate to a genetically-altered Solanaceae plant comprising a mutant suppressor of sp1 (ssp1) gene and a mutant single flower truss (sft) gene. In some embodiments, the genetically-altered Solanaceae plant comprises a mutant suppressor of sp1 (ssp1) gene and a mutant single flower truss (sft) gene, wherein the mutant genes are heterozygous. In some embodiments, the sft gene comprises a coding sequence having the nucleic acid sequence of SEQ ID NO: 20. In some embodiments, the sft gene comprises SEQ ID NO: 20. In some embodiments, the mutant ssp1 gene comprises a coding sequence having a nucleic acid sequence of SEQ ID NO: 2 or SEQ ID NO: 3 or encodes a mutant ssp1 protein that comprises SEQ ID NO: 5 or SEQ ID NO: 6. In some embodiments, the mutant ssp1 gene comprises a nucleic acid sequence that comprises SEQ ID NO: 2 or SEQ ID NO: 3 or encodes a mutant ssp1 protein that comprises SEQ ID NO: 5 or SEQ ID NO: 6. In some embodiments, the mutant ssp1 gene encodes a mutant ssp1 polypeptide that comprises a mutant SAP motif with a sequence of SEQ ID NO: 14 or SEQ ID NO: 15. In some embodiments, the mutant ssp1 gene comprises a C to T mutation at position 641 of SEQ ID NO: 1, a C to T mutation at position 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the genetically-altered Solanaceae plant is semi-determinate. In some embodiments, the genetically-altered semi-determinate Solanaceae plant is a tomato (*Solanum lycopersicum*) plant.

In some embodiments, the genetically-altered semi-determinate Solanaceae plant is inbred. In some embodiments, the mutant sft gene is sft-1906.

Yet another aspect relates to a seed for producing a genetically-altered Solanaceae plant as provided in any of the embodiments in the proceeding paragraph.

Other aspects relate to genetically-altered Solanaceae plant comprising a mutant self-pruning (sp) gene that comprises a coding sequence having the nucleic acid sequence of SEQ ID NO: 8. and a mutant single flower truss (sft) gene that comprises SEQ ID NO: 20. In some embodiments, the mutant self-pruning (sp) gene is heterozygous and the mutant single flower truss (sft) gene is heterozygous.

Further aspects relate to a genetically-altered Solanaceae plant comprising a mutant self-pruning (sp) gene that comprises the nucleic acid sequence of SEQ ID NO: 8. and a mutant single flower truss (sft) gene that comprises SEQ ID NO: 20, wherein the mutant genes are heterozygous.

Another aspect relates to a method of producing a genetically-altered Solanaceae plant comprising:

(a) introducing a mutant sft gene into a Solanaceae plant containing a mutant ssp1 gene, thereby producing a genetically-altered Solanaceae plant containing a mutant ssp1 gene and a mutant sft gene; and (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and the mutant sft gene, thereby producing a genetically-altered Solanaceae plant. In some embodiments, the method of producing a genetically-altered Solanaceae plant comprises:

(a) introducing a mutant sft gene into a Solanaceae plant part containing a mutant ssp1 gene, thereby producing a genetically-altered Solanaceae plant part containing the mutant ssp1 gene and the mutant sft gene;

(b) maintaining the genetically-altered Solanaceae plant part containing a mutant ssp1 and a mutant sft gene produced in (a) under conditions and for sufficient time for production of a genetically-altered Solanaceae plant containing the mutant ssp1 gene and the mutant sft gene from the plant part, thereby producing a genetically-altered Solanaceae plant containing the mutant ssp1 gene and the mutant sft gene;

(c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sft gene, thereby producing a genetically-altered Solanaceae plant that is semi-determinate.

Other aspects relate to a genetically-altered Solanaceae plant produced by a method provided in the preceding paragraph. Another aspect relates to a genetically-altered Solanaceae plant heterozygous for a mutant suppressor of sp1 (ssp1) gene and homozygous for a mutant single flower truss (sft) gene, wherein the genetically-altered Solanaceae plant has an altered yield compared to the yield of a wild-type Solanaceae plant.

Other aspects relate to a seed for producing a genetically-altered Solanaceae plant provided in the preceding paragraph.

Yet other aspects relate to a genetically-altered semi-determinate Solanaceae plant homozygous for a mutant suppressor of sp1 (ssp1) gene and homozygous for a mutant self pruning (sp) gene. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant sp gene comprises a coding sequence having the nucleic acid sequence of SEQ ID NO: 8. In some embodiments, the mutant sp gene comprises the nucleic acid sequence of SEQ ID NO: 8. In some embodiments, the genetically-altered semi-determinate Solanaceae plant is a tomato (*Solanum lycopersicum*) plant. In some embodiments, the genetically-altered semi-determinate Solanaceae plant is isogenic. In some embodiments, the genetically-altered semi-determinate Solanaceae plant is inbred.

Other aspects relate to a seed for producing a genetically-altered semi-determinate Solanaceae plant as described in any of the embodiments provided in the preceding paragraph.

Another aspect relates to a method of producing a genetically-altered semi-determinate Solanaceae plant comprising:

(a) introducing a mutant ssp1 gene into a Solanaceae plant containing a mutant sp gene, thereby producing a genetically-altered Solanaceae plant containing a mutant ssp1 gene and a mutant sp gene; and (b) self-crossing the genetically-altered Solanaceae plant produced in (a) or crossing two genetically-altered Solanaceae plants produced in (a) under conditions appropriate for producing a genetically-altered Solanaceae plant homozygous for the mutant ssp1 gene and the mutant sp gene, thereby producing a genetically-altered Solanaceae plant that is semi-determinate. In some embodiments, the method of producing a genetically-altered semi-determinate Solanaceae plant comprises:

(a) introducing a mutant ssp1 gene into a Solanaceae plant part containing a mutant sp gene, thereby producing a genetically-altered Solanaceae plant part containing the mutant ssp1 gene and the mutant sp gene;

(b) maintaining the genetically-altered Solanaceae plant part containing a mutant ssp1 and a mutant sp gene produced in (a) under conditions and for sufficient time for production of a genetically-altered Solanaceae plant containing the mutant ssp1 gene and the mutant sp gene from the plant part, thereby producing a genetically-altered Solanaceae plant containing the mutant ssp1 gene and the mutant sp gene;

(c) self-crossing the genetically-altered Solanaceae plant produced in (b) or crossing two genetically-altered Solanaceae plants produced in (b) under conditions appropriate for producing a genetically-altered Solanaceae plant homozygous for the mutant ssp1 gene and the mutant sp gene, thereby producing a genetically-altered Solanaceae plant that is semi-determinate. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant sp gene comprises a coding sequence having the nucleic acid sequence of SEQ ID NO: 8. In some embodiments, the mutant sp gene comprises the nucleic acid sequence of SEQ ID NO: 8. In some embodiments, in (a), the mutant ssp1 gene is introduced into a plant or a plant part by a method selected from the group consisting of: *Agrobacterium*-mediated recombination, viral-vector mediated recombination, microinjection, gene gun bombardment/biolistic particle delivery, nuclease mediated recombination, and electroporation. In some embodiments, the Solanaceae plant is a tomato (*Solanum lycopersicum*) plant. In some embodiments, the Solanaceae plant is inbred.

Another aspect relates to a genetically-altered semi-determinate Solanaceae plant produced by a method provided in the preceding paragraph.

Other aspects relate to a isolated polynucleotide encoding a mutant ssp1 protein having the amino acid sequence of SEQ ID NO: 5 or SEQ ID NO: 6. In some embodiments, the isolated polynucleotide comprises the nucleic acid sequence of SEQ ID NO: 2 or SEQ ID NO: 3.

Yet another aspect relates to a genetically-altered Solanaceae plant heterozygous for a mutant suppressor of sp1 (ssp1) gene and homozygous for a mutant self pruning (sp) gene, wherein the genetically-altered Solanaceae plant has an altered flowering time and shoot architecture compared to a wild-type Solanaceae plant. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant sp gene comprises a coding sequence having the nucleic acid sequence of SEQ ID NO: 8. In some embodiments, the mutant sp gene comprises the nucleic acid sequence of SEQ ID NO: 8. In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered Solanaceae plant is semi-determinate.

Other aspects relate to a seed for producing a genetically-altered Solanaceae plant of any of the embodiments provided in the preceding paragraph.

Yet another aspect relates to a genetically-altered Solanaceae plant homozygous for a mutant suppressor of sp1 (ssp1) gene, wherein the genetically-altered Solanaceae plant has an altered flowering time compared to a wild-type Solanaceae plant. In some embodiments, the mutant ssp1 gene comprises a nucleic acid sequence that encodes a mutant ssp1 protein that comprises a mutant SAP motif. In some embodiments, the mutant ssp1 gene comprises a nucleic acid sequence that encodes a mutant ssp1 protein that comprises a mutant SAP motif with a sequence of SEQ ID NO: 14 or SEQ ID NO: 15. In some embodiments, wherein the mutant ssp1 gene encodes a mutant ssp1 polypeptide comprising the sequence of SEQ ID NO: 5 or SEQ ID NO: 6. In some embodiments, the mutant ssp1 gene comprises a C to T mutation at position 641 of SEQ ID NO: 1, a C to T mutation at 647 of SEQ ID NO: 1, or a C to T mutation at position 641 and 647 of SEQ ID NO: 1. In some embodiments, the mutant ssp1 gene comprises a coding sequence having the nucleic acid sequence of SEQ ID NO: 2 or SEQ ID NO: 3. In some embodiments, the mutant ssp1 gene comprises the nucleic acid sequence of SEQ ID NO: 2 or SEQ ID NO: 3. In some embodiments, the mutant sp gene comprises a coding sequence having the nucleic acid sequence of SEQ ID NO: 8. In some embodiments, the mutant sp gene comprises the nucleic acid sequence of SEQ ID NO: 8. In some embodiments, the genetically-altered Solanaceae plant is a tomato (*Solanum lycopersicum*) plant. In some embodiments, the genetically-altered Solanaceae plant is isogenic. In some embodiments, the genetically-altered Solanaceae plant is inbred. In some embodiments, the genetically-altered Solanaceae plant is homozygous for a wild-type SELF PRUNING (SP) gene.

Other aspects relate to a seed for producing a genetically-altered Solanaceae plant of any embodiment provided in the preceding paragraph.

EXAMPLES

Example 1

Identifying Mutant Plants Providing Semi-Determinate or Semi-Indeterminate Shoot Architecture Phenotypes The crop plant tomato (*Solanum lycopersicum*) was used to identify mutant plants with a semi-determinate phenotype. The previously generated tomato EMS mutation library in the determinate M82 background was used in the methods described below (Menda N Y et al. 2004. Plant J 38.861-72). The mutation library was previously generated by treating seeds with ethyl methanesulfonate (0.5 percent EMS for 12 h; LD15), producing an M1 generation. These seeds were self-crossed to produce 13,000 M2 families with random mutations in unknown locations.

The M82 determinate (M82D) isogenic background is known to contain a mutation in the SELF PRUNING (SP) gene (Pnueli, et al. Development 1989), resulting in a tomato plant with a determinate (D) growth habit. In D-type plants, the sympodial shoots produce progressively fewer leaves until the plant terminates growth in two successive inflorescences. In contrast, indeterminate (ID) tomato plants generate successive sympodial units (SYM) that produce three leaves each, and SYMs continue to reiterate to generate an ID shoot. The M2 EMS mutation library described above was generated in an M82D background and self-crossed to produce approximately six thousand independent mutant tomato plants and many fertile mutants which contained mutations at unidentified locations which were carried over into the M3 inbred generation. These lines were screened in both the M2 and M3 generations for homozygous recessive mutant phenotypes that partially suppressed the determinate growth phenotype of the M82D background, resulting in a semi-determinate shoot architecture phenotype. In particular, flowering time, flower production per inflorescence, and shoot architecture were examined. Single lines were identified that contained at least one M3 plant with a semi-determinate phenotype.

Figure 3:
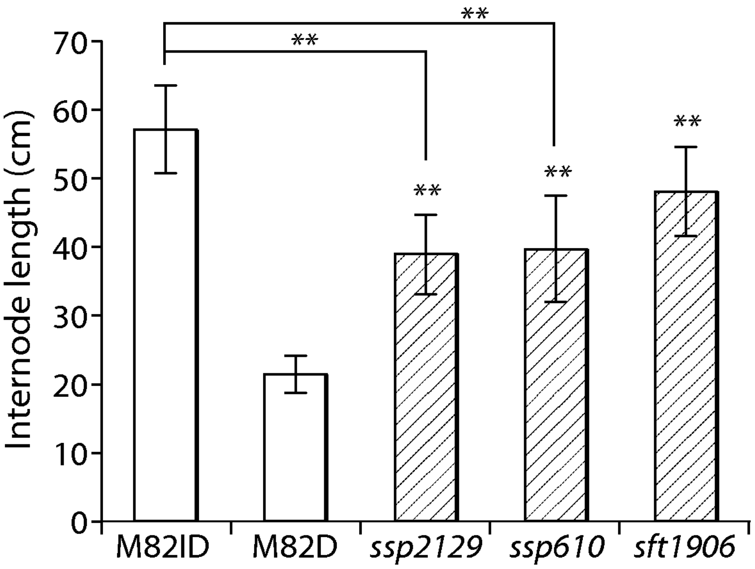
FIG. 3 shows internode length between inflorescences in sympodial units in determinate (cultivar M82D), indeterminate (cultivar M82ID and sft1906; sp) and semi-indeterminate (ssp-2129; sp and, ssp-610; sp) plants. Note the intermediate internode length for the semi-indeterminate ssp-2129; sp and ssp-610; sp double mutant plants, which reflects a reduced sympodial index to an average of two leaves. ** $P<0.01$, student t-test against M82D, and against M82ID indicated with lines.
Figure 4A:
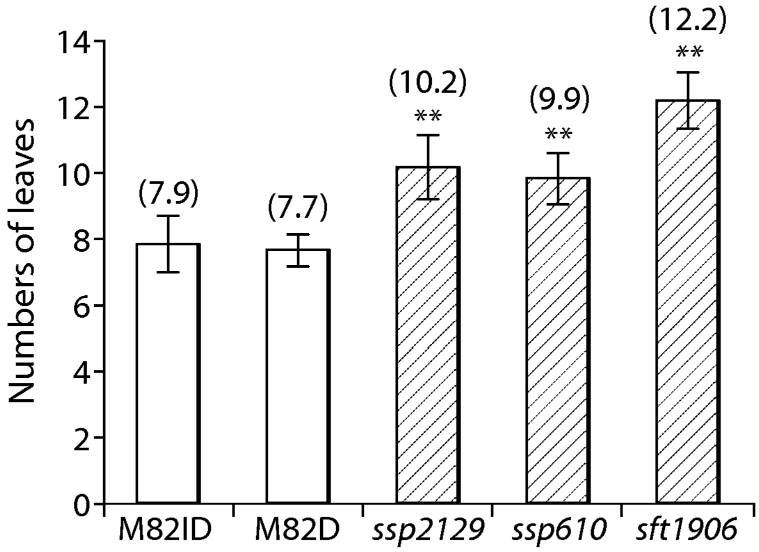
FIG. 4A shows the numbers of leaves produced by the primary shoot.
Figure 4B:
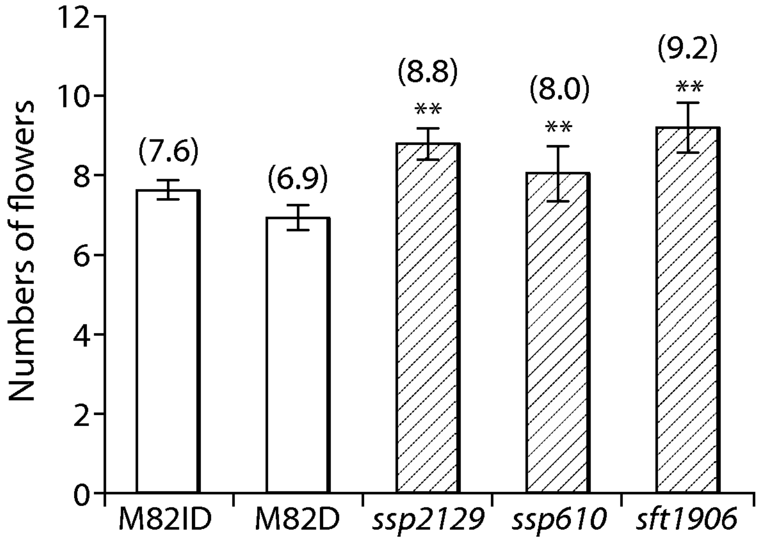
FIG. 4B shows the numbers of flowers per inflorescence.
Figure 4C:
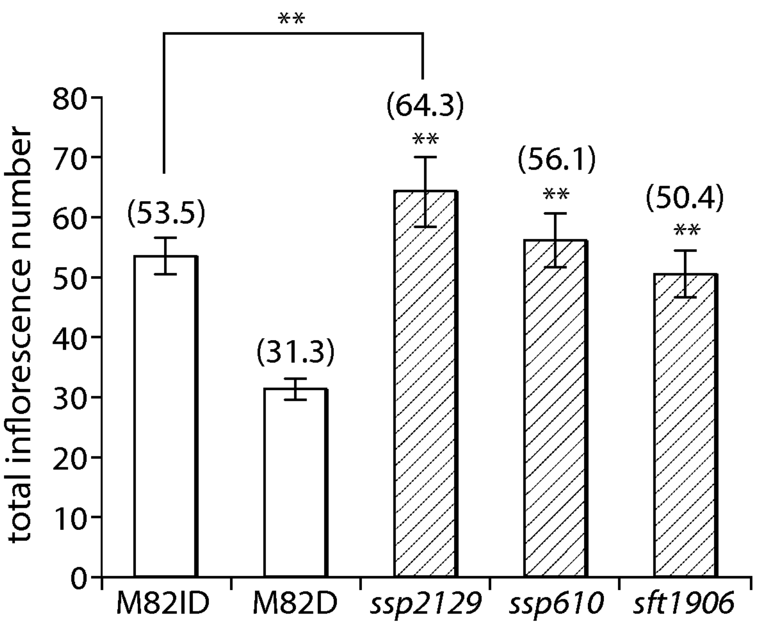
FIG. 4C shows the total number of inflorescences generated from each genotype.
Figure 4D:
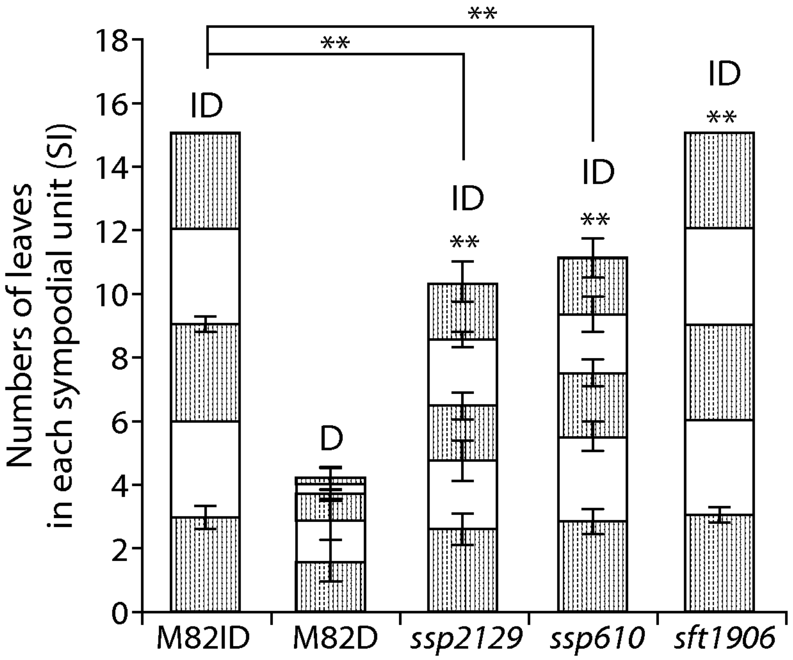
FIG. 4D shows numbers of leaves within each sympodial shoot (i.e.; sympodial index) in M82ID, M82D, ssp-2129 and ssp-610 and sft1906. Note the quantitative range of sympodial indices created by different homozygous and heterozygous mutant combinations. ID, indeterminate SYM growth; D, determinate SYM growth; SD, semi-determinate SYM growth. The font size of "D" and "ID" indicate relative values of shoot terminations from 20 plants.  $P<0.01$, students t-test against M82D indicated with asterisks above bars, and against M82ID indicated asterisks above lines. Standard error is shown for FIGS. 4**B and C, and in all other cases standard deviation.

Two M2 families, e2129 and e610, were identified that had a low frequency (less than or equal to ~25%) of plants with an altered flowering time and shoot architecture resembling a semi-determinate phenotype. FIG. 2 shows that homozygosity for the e2129 mutant (designated ssp-2129) in the $sp^{-/-}$ M82 mutant background suppressed sympodial shoot termination compared to the $sp^{-/-}$ mutant alone. FIG. 2, left, depicts a $sp^{-/-}$ determinate plant where leaf number in each sympodial shoot gradually decreases, leading to shoot termination in two successive inflorescences. FIG. 2, right, depicts an indeterminate wild-type plant where each sympodial unit produces three leaves and this process continues indefinitely. FIG. 2, center, depicts an ssp-2129; $sp^{-/-}$ double mutant with semi-determinate sympodial shoot development, such that each sympodial shoot unit now produces two leaves, instead of the typical three leaves produced in wild-type indeterminate tomato plants. FIG. 3 shows quantification of internode length among 4 inflorescences in determinate $sp^{-/-}$ mutants (M82D), semi-determinate ssp-2129; $sp^{-/-}$ double mutants and ssp-610; $sp^{-/-}$ double mutants (ssp-2129 and ssp-610, respectively), and wild-type plants (M82ID). The p-value was measured by a student's t-test against M82D and M82ID (P<0.01 for ssp-2129 and ssp-610, indicated by **).

FIG. 4 shows quantification of leaf numbers produced by the primary shoot meristem (PSM) indicating flowering time and sympodial units in both $sp^{-/-}$ and ssp-2129; $sp^{-/-}$ backgrounds. Note that ssp-2129;$sp^{-/-}$ double mutant plants displayed a delayed flowering time as indicated by the increased leaf numbers in the PSM compared to $sp^{-/-}$ single mutant plants. ssp-2129;$sp^{-/-}$ plants also displayed more leaves within sympodial units compared to $sp^{-/-}$ plants, but fewer leaves within sympodial units compared to wild-type indeterminate plants. This semi-determinacy was observed for a second mutant allele, ssp-610 in the sp mutant background.

To identify the genetic mutation(s) resulting in the altered flowering time and shoot architecture in these two families, one family, e2129, was further analyzed using previously reported map-based cloning procedures (Lippman et al, PLoS Biology 2008). A single M3 ssp-2129 mutant plant was crossed to a wild-type species, *S. piminellifolium*, with known polymorphisms throughout the genome (The Tomato Genome sequence, Nature, 2012). The F1 hybrid was then self-crossed to produce an F2 generation of progeny plants segregating for both the ssp-2129 mutation and the DNA polymorphisms between M82 and *S. pimpinellifolium*. Approximately 200 F2 plants were scored for altered flowering time and semi-determinate shoot architecture phenotypes, reflecting homozygosity of the ssp-2129 mutation.

The homozygous mutant F2 plants (those with the altered flowering time and shoot architecture) were then genotyped with evenly spaced polymorphic DNA markers spanning all 12 tomato chromosomes using the bulk segregant mapping technique. DNA was isolated from at least 20 mutant plants (those with the altered flowering time and shoot architecture phenotype) and from 20 wild-type plants. DNA from the mutant plants was pooled to form pool 1 and DNA from the wild-type plants was pooled to form pool 2. A 10 centiMorgan (cM) scan was performed to identify M82 polymorphisms that were over-represented in pool 1 relative to pool 2, reflective of the origin of the ssp-2129 mutation in the M82 background. Over-representation of polymorphisms in pool 1 was found within at 2 Mb mapping interval between PCR markers 4029 and 4230, corresponding to 40M and 42M on chromosome 2, as shown in FIG. 5.

To find the location of the mutation within this region, RNA was extracted from wild-type and mutant plants. This RNA was converted to cDNA and sequenced using Illumina sequencing. The sequencing reads were then mapped to the known gene annotations and only those within the 2 Mb region described above were analyzed. A large number of C to T mutations were observed at a single location, position 647 according to SEQ ID NO: 2 which corresponds to amino acid position 216 according to SEQ ID NO: 5, within the C-terminus of the tomato orthologue of the *Arabidopsis* FLOWERING LOCUS D (FD) gene. The tomato orthologue is referred herein as SUPPRESSOR OF SP1 (SSP1).

Following identification of the mutation present in the e2129 family, the e610 mutant, a confirmed allele in the SSP1 gene by complementation test with the ssp-2129 mutant as described below, was examined to see if the unknown mutation in that family also occurred in the SSP1 gene. Heterozygous plants with one copy of ssp-2129 and one copy of ssp-610 phenocopied the ssp-2129 homozygous mutant and the ssp-610 homozygous mutant plant, indicating that these two mutations were in the same gene. Following the complementation test, DNA was extracted from e610 mutant plants and Sanger sequencing was performed to determine if the SSP1 gene locus contained a mutation. A 'C' to 'T' mutation was identified in SSP1 at position 641 according to SEQ ID NO: 3 which corresponds to amino acid position 214 according to SEQ ID NO: 6.

Figure 5:
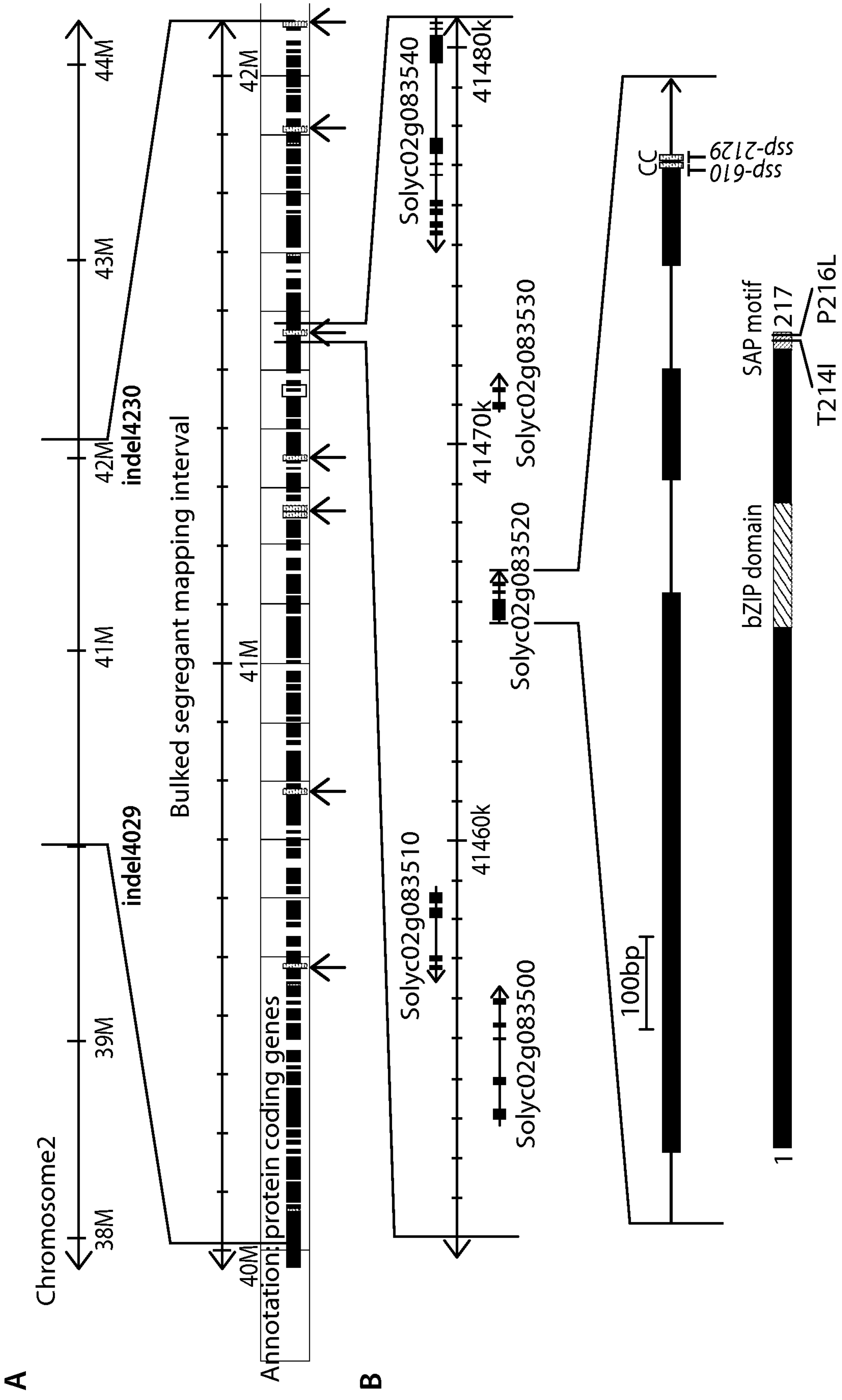
FIG. 5 is a schematic of the map-based cloning procedure used to identify the SSP1 gene. The highlighted region is the mapping interval identified using map-based cloning. Arrows indicate single nucleotide polymorphisms (SNPs). The coding region of SSP1 is shown. The C to T mutations in the protein C-terminus of ssp-2129 and ssp-610 are indicated.

FIG. 5 summarizes the map-based cloning of the SSP1 gene discussed above. FIG. 5A shows the SSP1 map position on chromosome 2 localized to a 2.1M interval between markers indel4029 (4029×10k) and indel4230 (4230×20k) was defined by bulk segragant analysis. An F2 mapping population segregating for the recessive ssp1 mutant was generated by self-pollinating an *S. pimpinellifolium* sp-x ssp1 sp- (cv. M82) F1 plant. At least four insertion-deletion (indel) PCR markers were used for each of the 12 tomato chromosomes on a pool of DNA composed of 20 ssp1 mutant individuals compared to a pool of DNA composed of 20 wild-type individuals. Deconvolution of the mutant pool revealed a recombination-defined internal of 40M-42.1M on chromosome 2. FIG. 5B depicts Illumina RNA-sequencing (RNA-seq), which was performed on RNA isolated from reproductive meristems and used to identify and reconstruct DNA protein coding sequences from expressed genes in the mapping interval. RNA-seq reads revealed eight genes (positions indicated by arrows) expressed in meristems. Single nucleotide polymorphisms (SNP) were identified relative to the reference annotation for the eight expressed genes, which revealed a C-to-T DNA change in the coding sequence of Solyc02g083520 of the ssp-2129 mutant allele. Sequencing of the ssp-610 allele revealed a C-to-T change at a nearby location in the coding sequence of Solyc02g083520. Each mutation causes a missense amino acid changes in the conserved SAP motif of the closest tomato homolog of the *Arabidopsis* flowering gene FLOWERING LOCUS D (FD), encoding a bZIP transcription factor.

A summary of the sequences of both the wild-type SSP1 gene and the two mutant alleles, ssp-2129 and ssp-610, is provided in FIGS. 6 and 7, which depict ClustalW analyses of the nucleotide and amino acid sequences, respectively. The nucleotide and amino acid sequences for wild-type SSP1, mutant ssp-2129, mutant ssp-610, wild-type SP, and mutant sp are also listed after Example 2. Mutations present in the nucleotide and amino acid sequences of each mutant nucleic acid or protein are indicated as underlined and bolded nucleotides or amino acids.

Example 2

Identifying Mutant Plants Providing Desirable Plant Traits Such as Brix, Brix Yield, Red Fruit Yield, and Total Yield A mutant SINGLE FLOWER TRUSS (SFT) gene, sft-1906, was identified in tomato plants using the same techniques described above in Example 1. sft-1906 was determined to have a mutation of Valine to Methionine at position 132. A summary of the nucleotide and amino acid sequences of the wild-type SFT gene and the mutant allele, sft-1906, is provided in FIGS. 9 and 10, which depict ClustalW analyses of the nucleotide and amino acid sequences, respectively. The nucleotide and amino acid sequences for the wild-type SFT gene and the mutant allele, sft-1906, are also listed below. Mutations present in the nucleotide and amino acid sequences of each mutant nucleic acid or protein are indicated as underlined and bolded nucleotides or amino acids.

Tomato plants carrying sft-1906 were crossed with tomato plants carrying ssp2120 or ssp610 and compared to plants having other genetic backgrounds (M82 (sp), ssp2129 x M82 F1, ssp610 x M82 F1, and sft1906 x M82 F1). It was found that all of the combined mutant tomato plants (ssp2129 x sft1906, ssp610 x sft1906, ssp2129 x M82 F1, ssp610 x M82 F1, and sft1906 x M82 F1) had improved Brix Yield, Brix, Red Fruit Yield, and Total Yield compared to M82 plants (FIG. 8). Data on red and total fruit yield were generated from replicated field trials and Brix data was obtained using a refractometer (see below). Tomato plants doubly heterozygous for both an ssp1 mutation and a sft mutation had the highest improvement in Brix Yield, Brix, Red Fruit Yield, and Total Yield (FIG. 8). Tomato plants were grown under wide (1 plant per m2) spacing using drip irrigation for field trials. When all plants have 80% or more red fruits, total fruits and total red fruits were measured by weight (kg) per plant. Ten red fruits collected randomly from each plant were used for determine Brix value, which was measured by a digital Brix refractometer (ATAGO PAL-1). Brix-yield was calculated by the multiplied output of Brix and total fruit yield measured in g/m2. Each genotype in the experiments was represented by a minimum of 15 replicates in two locations (Riverhead, N.Y. USA and Akko, Israel). All plants were transplanted in a completely randomized design.

| Nucleic Acid and Polypeptide Sequences |
| --- |

Nucleic Acid

>SSP1 coding sequence (SEQ ID NO: 1)

ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT

GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAACTGCTCCATTTTGA

>ssp-2129 coding sequence (SEQ ID NO: 2)

ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT

-continued

GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAACTGCTCTATTTTGA

>ssp-610 coding sequence (SEQ ID NO: 3)

ATGTGGTCATCAAGCAGTGATAACAGGGGACTCTCTGCTTCTTCTTCTTCATCTTCATCC

TCATCTCATTCACCATTTTCTCCAAGACTCAAAACAATGGAAGAAGTGTGGAAAGATATT

AATCTTTCTTCACTTCAAGATCACACTACGAATTACTCTAGAGATCATCATCATCTTCAT

GATCATAATCATCAAGCTGCTAATTTTGGTGGAATGATTTTACAAGATTTTTTGGCAAGG

CCTTTTGCTAATGAATCTTCACCAGCAGCAGCAGCAGCAGCAGCCTCCCCTGTTTCAGCT

ACAACTATGCTGAATTTGAACTCTGTTCCTGAGCTTCATTTCTTTGATAACCCATTGAGG

CAAAACTCAATCTTGCACCAACCAAATGCAAGTGGAAGAAAAAGGGTTGTCCCTGAAACA

GAAGACAATTCTACAGGGGATAGAAGAAATCAGAGGATGATCAAGAACAGAGAGTCTGCT

GCTAGATCAAGAGCTAGAAAGCAGGCTTATATGAACGAGTTGGAATCAGAAGTGGCACAT

TTAGTTGAAGAAAATGCAAGGCTCAAGAAGCAGCAGCAACAGTTACGAGTAGATGCAGCT

AATCAAGTTCCCAAAAAGAACACTCTTTATCGGACGTCAATTGCTCCATTTTGA

Protein
>SSP (SEQ ID NO: 4)

MWSSSSDNRGLSASSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHEFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSTAPF*

>ssp-2129

(SEQ ID NO: 5)

MWSSSSDNRGLSASSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHEFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSTALF*

>ssp-610

(SEQ ID NO: 6)

MWSSSSDNRGLSASSSSSSSSSHSPFSPRLKTMEEVWKDINLSSLQDHTTNYSRDHHHLH

DHNHQAANFGGMILQDFLARPFANESSPAAAAAAASPVSATTMLNLNSVPELHEFDNPLR

QNSILHQPNASGRKRVVPETEDNSTGDRRNQRMIKNRESAARSRARKQAYMNELESEVAH

LVEENARLKKQQQQLRVDAANQVPKKNTLYRTSIAPF*

Nucleic acid
>SP (wild-type) coding sequence (SEQ ID NO: 7)

ATGGCTTCCAAAATGTGTGAACCCCTTGTGATTGGTAGAGTGATTGGTGAAGTTGTTGATTATTTCT

GTCCAAGTGTTAAGATGTCTGTTGTTTATAACAACAACAAACATGTCTATAATGGACATGAATTCT

TTCCTTCCTCAGTAACTTCTAAACCTAGGGTTGAAGTTCATGGTGGTGATCTCAGATCCTTCTTCAC

ACTGATCATGATAGATCCAGATGTTCCTGGTCCTAGTGATCCATATCTCAGGGAACATCTACACTG

GATTGTCACAGACATTCCAGGCACTACAGATTGCTCTTTTGGAAGAGAAGTGGTTGGGTATGAAAT

GCCAAGGCCAAATATTGGAATCCACAGGTTTGTATTTTTGCTGTTTAAGCAGAAGAAAAGGCAAA

CAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

-continued

>sp (mutant) coding sequence (SEQ ID NO: 8)

ATGGCTTCCAAAATGTGTGAACCCCTTGTGATTGGTAGAGTGATTGGTGAAGTTGTTGATTATTTCT

GTCCAAGTGTTAAGATGTCTGTTGTTTATAACAACAACAAACATGTCTATAATGGACATGAATTCT

TTCCTTCCTCAGTAACTTCTAAACCTAGGGTTGAAGTTCATGGTGGTGATCTCAGATCCTTCTTCAC

ACTGATCATGATAGATCCAGATGTTCTTGGTCCTAGTGATCCATATCTCAGGGAACATCTACACTG

GATTGTCACAGACATTCCAGGCACTACAGATTGCTCTTTTGGAAGAGAAGTGGTTGGGTATGAAAT

GCCAAGGCCAAATATTGGAATCCACAGGTTTGTATTTTTGCTGTTTAAGCAGAAGAAAAGGCAAA

CAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

Protein

>SP (wild-type)

(SEQ ID NO: 9)

MASKMCEPLVIGRVIGEVVDYFCPSVKMSVVYNNNKHVYNGHEFFPSSVTSKPRVEVHGG

DLRSFFTLIMIDPDVPGPSDPYLREHLHWIVTDIPGTTDCSFGREVVGYEMPRPNIGIHR

FVFLLFKQKKRQTISSAPVSRDQFSSRKFSEENELGSPVAAVFFNCQRETAARRR*

>sp (mutant)

(SEQ ID NO: 10)

MASKMCEPLVIGRVIGEVVDYFCPSVKMSVVYNNNKHVYNGHEFFPSSVTSKPRVEVHGG

DLRSFFTLIMIDPDVLGPSDPYLREHLHWIVTDIPGTTDCSFGREVVGYEMPRPNIGIHR

FVFLLFKQKKRQTISSAPVSRDQFSSRKFSEENELGSPVAAVFFNCQRETAARRR*

Nucleic acid

>SFT (wild-type) coding sequence (SEQ ID NO: 18)

ATGCCTAGAGAACGTGATCCTCTTGTTGTTGGTCGTGTGGTAGGGGATGTATTGGACCCTTTCACA

AGAACTATTGGCCTAAGAGTTATATATAGAGATAGAGAAGTTAATAATGGATGCGAGCTTAGGCC

TTCCCAAGTTATTAACCAGCCAAGGGTTGAAGTTGGAGGAGATGACCTACGTACCTTTTTCACTTT

GGTTATGGTGGACCCTGATGCTCCAAGTCCGAGTGATCCAAATCTGAGAGAATACCTTCACTGGTT

GGTCACCGATATTCCAGCTACCACAGGTTCAAGTTTTGGGCAAGAAATAGTGAGCTATGAAAGTCC

AAGACCATCAATGGGAATACATCGATTTGTATTTGTATTATTCAGACAATTAGGTCGGCAAACAGT

GTATGCTCCAGGATGGCGTCAGAATTTCAACACAAGAGATTTTGCAGAACTTTATAATCTTGGTTT

ACCTGTTGCTGCTGTCTATTTTAATTGTCAAAGAGAGAGTGGCAGTGGTGGACGTAGAAGATCTGC

TGATTGA

>sft (mutant) coding sequence (SEQ ID NO: 20)

ATGCCTAGAGAACGTGATCCTCTTGTTGTTGGTCGTGTGGTAGGGGATGTATTGGACCCTTTCACA

AGAACTATTGGCCTAAGAGTTATATATAGAGATAGAGAAGTTAATAATGGATGCGAGCTTAGGCC

TTCCCAAGTTATTAACCAGCCAAGGGTTGAAGTTGGAGGAGATGACCTACGTACCTTTTTCACTTT

GGTTATGGTGGACCCTGATGCTCCAAGTCCGAGTGATCCAAATCTGAGAGAATACCTTCACTGGTT

GGTCACCGATATTCCAGCTACCACAGGTTCAAGTTTTGGGCAAGAAATAGTGAGCTATGAAAGTCC

AAGACCATCAATGGGAATACATCGATTTGTATTTGTATTATTCAGACAATTAGGTCGGCAAACAAT

GTATGCTCCAGGATGGCGTCAGAATTTCAACACAAGAGATTTTGCAGAACTTTATAATCTTGGTTT

ACCTGTTGCTGCTGTCTATTTTAATTGTCAAAGAGAGAGTGGCAGTGGTGGACGTAGAAGATCTGC

TGATTGA

-continued

Protein
>SFT (wild-type)
(SEQ ID NO: 19)
MPRERDPLVVGRVVGDVLDPFTRTIGLRVIYRDREVNNGCELRPSQVINQPRVEVGGDDL

RTFFTLVMVDPDAPSPSDPNLREYLHWLVTDIPATTGSSFGQEIVSYESPRPSMGIHRFV

FVLFRQLGRQTVYAPGWRQNFNTRDFAELYNLGLPVAAVYFNCQRESGSGGRRRSAD*

>sft (mutant)
(SEQ ID NO: 21)
MPRERDPLVVGRVVGDVLDPFTRTIGLRVIYRDREVNNGCELRPSQVINQPRVEVGGDDL

RTFFTLVMVDPDAPSPSDPNLREYLHWLVTDIPATTGSSFGQEIVSYESPRPSMGIHRFV

FVLFRQLGRQTMYAPGWRQNFNTRDFAELYNLGLPVAAVYFNCQRESGSGGRRRSAD*

Genomic Sequences

>SP (wild-type) genomic
(SEQ ID NO: 22)
*ATGGCTTCCAAAATGTGTGAACCCCTTGTGATTGGTAGAGTGTGATTGGTGAAGTTGTTGATTATTTCTG*

*TCCAAGTGTTAAGATGTCTGTTGTTTATAACAACAACAAACATGTCTATAATGGACATGAATTCCTTTC*

*CTTCCTCAGTAACTTCTAAACCTAGGGTTGAAGTTCATGGTGGTGATCTCAGATCCTTCTTCACACTG*

GTATATATTAATCTTCAACACTTCCAATTTACTCCGTCTGTCTGTCCTAATTTATGTCACACATTTTC

TATGATATATAGTTTTAGAAATTATTCAAGACCATAACTTTTTAAAGAAAAAATCATAGACTTTCTT

AGTCAACGTCAAATAAATTGAGACGGACAAGATGACATGATTAGTACATTTATCTTCTATTATTGA

CCTCTCATTTTCTTTTATACATTATTTGACAG*ATCATGATAGATCCAGATGTTCCTGGTCCTAGTGAT*

*CCATATCTCAGGGAACATCTACACTGG*TATAGACAACATATGCCTTAAAACTAACTCAGTCAATTTT

ATCTTCAATTGTTTACTTTGGAAGGGGAAATGACATGATCATTATATCATAGTACAAATTATTATGT

AATTTCTGTTCGTCTAAAAAATGTCACTTTAGAAAAAACTGATAATCATATACAATACCACAATAA

AGATAGAAGAACATGTACTAATATTGAACTTAAATAATGAGTACTAGGAGTATTATTAATTAACTT

TAAAAATGCTAGTCAATATACCTATGTTTATATGTTAAAAAATCCTTTATATTTGGAAACATGAGT

ACTCCTATACCATACAATGTTGTCGTACAGTTGATTAGACGGGCAAATTAAACAAATGTCCAATAA

TTGTACTAATTAATAACTACTTGTTCTCTTCATCTATTATTAGTTATTACCAAAAAAAGAGGACTGC

AAAATGGTGATATTATTATGTGTAACGGAAAAAAACGTACTCTATTTAATATGATAGAATCAAAGT

GACATATTTTGTTCTAGTTAGACAAATAAGTAACTGAAAAGAGGATTTGACCATCTTTACAGG*AT*

*TGTCACAGACATTCCAGGCACTACAGATTGCTCTTTTGG*TATGTATCCTTAACCCATAAATCAAAAT

AATGTACTTTCTTTTTATTTGCCATTAATATCTCTAGTACAAAAAAGAAATATTATAAAAAAAATTA

ATTTCAATTTTTATATTATAGGTTTAAGATAATAATATTAAACGATATTTTAGTCTCTACCAAATAG

ACGAGCAAATTAAAACTAAGAAAGCACTACATGTTTTCTTTATATTATTAGTATAAAAATATATTA

TAATTTGCCTGGTGGTAATAGGATCAAAGTATTGATTCTTAATTATTATTATATAATTAATAATAAT

GGTAAACAAAAAGATATAAAGTGCTTACCTCCTAATTCCCTATATGAAAAAATATACTTACTTAAT

TACTCTTTTTACACGTAAGCATGCATTTAAAAAAAATATTAAAAAATTATTCCAGAGGTTATATATA

ATATGTATGGATAAAAAAAAAAATTCACCTATATACATAATAATATAATTTTCGAGTGAATTGACCG

CCCTTCAGCATCATTATATAATGTTATCGATCTAGGTCTTTGTGTGAAATTAAAAGTTATTTATACG

GTTAGTACGATCGCGTAATAACGAAGGTAAAAATATTTCAGG*AAGAGAAGTGGTTGGGTATGAAAT*

*GCCAAGGCCAAATATTGGAATCCACAGGTTTGTATTTTTGCTGTTTAAGCAGAAGAAAAGGCAAACA*

*ATATCGAGTGCACCAGTGTCCAGAGATCAATTTAGTAGTAGAAAATTTTCAGAAGAAAATGAACTTG*

-continued

*GCTCACCAGTTGCTGCTGTTTTCTTCAATTGTCAGAGGGAAACTGCCGCTAGAAGGCGTTGA*

* Marker: bold with underbar, * Exon: Italics and bold,

>sp(mutant)genomic (mutation in brackets)

(SEQ ID NO: 23)

*ATGGCTTCCAAAATGTGTGAACCCCTTGTGATTGGTAGAGTGATTGGTGAAGTTGTTGATTATTTCTG*

*TCCAAGTGTTAAGATGTCTGTTGTTTATAACAACAACAAACATGTCTATAATGGACATGAATTCTTTC*

*CTTCCTCAGTAACTTCTAAACCTAGGGTTGAAGTTCATGGTGGTGATCTCAGATCCTTCTTCACACTG*

GTATATATTAATCTTCAACACTTCCAATTTACTCCGTCTGTCTGTCCTAATTTATGTCACACATTTTC

TATGATATATAGTTTTAGAAATTATTCAAGACCATAACTTTTTAAAGAAAAAATCATAGACTTTCTT

AGTCAACGTCAAATAAATTGAGACGGACAAGATGACATGATTAGTACATTTATCTTCTATTATTGA

CCTCTCATTTTCTTTTATACATTATTTGACAG*ATCATGATAGATCCAGATGTTC[[T]]TGGTCCTAGTG*

*ATCCATATCTCAGGGAACATCTACACTGG*TATAGACAACATATGCCTTAAAACTAACTCAGTCAATT

TTATCTTCAATTGTTTACTTTGGAAGGGGAAATGACATGATCATTATATCATAGTACAAATTATTAT

GTAATTTCTGTTCGTCTAAAAAATGTCACTTTAGAAAAAACTGATAATCATATACAATACCACAAT

AAAGATAGAAGAACATGTACTAATATTGAACTTAAATAATGAGTACTAGGAGTATTATTAATTAA

CTTTAAAAATGCTAGTCAATATACCTATGTTTATATGTTAAAAAATCCTTTATATTTGGAAACATGA

GTACTCCTATACCATACAATGTTGTCGTACAGTTGATTAGACGGGCAAATTAAACAAATGTCCAAT

AATTGTACTAATTAATAACTACTTGTTCTCTTCATCTATTATTAGTTATTACCAAAAAAAGAGGACT

GCAAAATGGTGATATTATTATGTGTAACGGAAAAAAACGTACTCTATTTAATATGATAGAATCAAA

GTGACATATTTTGTTCTAGTTAGACAAATAAGTAACTGAAAAGAGGATTTGACCATCTTTACAGG

*ATTGTCACAGACATTCCAGGCACTACAGATTGCTCTTTTGG*TATGTATCCTTAACCCATAAATCAAA

ATAATGTACTTTCTTTTTATTTGCCATTAATATCTCTAGTACAAAAAAGAAATATTATAAAAAAAAT

TAATTTCAATTTTTATATTATAGGTTTAAGATAATAATATTAAACGATATTTTAGTCTCTACCAAAT

AGACGAGCAAATTAAAACTAAGAAAGCACTACATGTTTTCTTTATATTATTAGTATAAAAATATAT

TATAATTTGCCTGGTGGTAATAGGATCAAAGTATTGATTCTTAATTATTATTATATAATTAATAATA

ATGGTAAACAAAAAGATATAAAGTGCTTACCTCCTAATTCCCTATATGAAAAAATATACTTACTTA

ATTACTCTTTTTACACGTAAGCATGCATTTAAAAAAATATTAAAAAATTATTCCAGAGGTTATATA

TAATATGTATGGATAAAAAAAAAAATTCACCTATATACATAATAATATAATTTTCGAGTGAATTGAC

CGCCCTTCAGCATCATTATATAATGTTATCGATCTAGGTCTTTGTGTGAAATTAAAAGTTATTTATA

CGGTTAGTACGATCGCGTAATAACGAAGGTAAAAATATTTC*AAGAGAAGTGGTTGGGTATGAA*

*ATGCCAAGGCCAAATATTGGAATCCACAGGTTTGTATTTTTGCTGTTTAAGCAGAAGAAAAGGCAAA*

*CAATATCGAGTGCACCAGTGTCCAGAGATCAATTTAGTAGTAGAAAATTTTCAGAAGAAAATGAACTT*

*GGCTCACCAGTTGCTGCTGTTTTCTTCAATTGTCAGAGGGAAACTGCCGCTAGAAGGCGTTGA*

* Marker: bold with underbar, * Exon: Italics and bold,

>SSP1 (wild-type) genomic (SEQ ID NO: 24)

*ATGTGGTCATCAAGCAGTGATAACAGGGGACTCTCTGCTTCTTCTTCTTCATCTTCATCCTCATCTCA*

*TTCACCATTTTCTCCAAGACTCAAAACAATGGAAGAAGTGTGGAAAGATATTAATCTTTCTTCACTTC*

*AAGATCACACTACGAATTACTCTAGAGATCATCATCATCTTCATGATCATAATCATCAAGCTGCTAAT*

*TTTGGTGGAATGATTTTACAAGATTTTTTTGGCAAGGCCTTTTGCTAATGAA*TCTTCACCAGCAGCAGC

AGCAGCAGCAGCCTCCCCTGTTTCAGCTACAACTATGCTGAATTTGAACTCTGTTCCTGAGCTTCAT

TTCTTTGATAACCCATTGAGGCAAAACTCAATCTTGCACCAACCAAATGCAAGTGGAAGAAAAAG

GGTTGTCCCTGAAACAGAAGACAATTCTACAGGGGATAGAAGAAATCAGAGGATGATCAAGAAC

-continued

AGAGAGTCTGCTGCTAGATCAAGAGCTAGAAAGCAGGTAAGTGACACTCAACTTTGTCTTAATCCT

GTCAATTTTGTGCTTATACATCAACTATGTTCCATATTGTTACTCTTTTGCTGCTTCTATTCTTGATT

TGAACAATATGCCGAGTTACTCTGTTTGCAG*GCTTATATGAACGAGTTGGAATCAGAAGTGGCACAT*

*TTAGTTGAAGAAAATGCAAGGCTCAAGAAGCAGCAGCAACAG*GTTCTCTTATCTTTCTTTATTTCTGT

CACTTTTAAAATTCAGTTTATAAAAAAAATGGATATAACTGATTCATAATAAATTGGTGTTTTCTTA

ATTTGTACAG*TTACGAGTAGATGCAGCTAATCAAGTTCCCAAAAAGAACACTCTTTATCGGACGTCA*

*ACTGCTCCATTTTGA*GATCTTATTATAATTTGGTTTCCTAGTGCTACATTAGTATTAAGAACAATTTC

CCATTTGGCTGTATTTTGTTTGTAATATGCACCAACTGTTGTTTTGATGGTGGCCTTGTGGGGCGAT

GAATATTCGTATGACAAAATAAGAAGGGAAAAAATAGGTTGTGAATTAAGGAAAGTGTAGGCCAT

TATTAGTACTCTATCA

>ssp-2129 genomic (mutation in brackets)

(SEQ ID NO: 25)

*ATGTGGTCATCAAGCAGTGATAACAGGGGACTCTCTGCTTCTTCTTCTTCATCTTCATCCTCATCTCA*

*TTCACCATTTTCTCCAAGACTCAAAACAATGGAAGAAGTGTGGAAAGATATTAATCTTTCTTCACTTC*

*AAGATCACACTACGAATTACTCTAGAGATCATCATCATCTTCATGATCATAATCATCAAGCTGCTAAT*

*TTTGGTGGAATGATTTTACAAGATTTTTTGGCAAGGCCTTTTGCTAATGAA*TCTTCACCAGCAGCAGC

AGCAGCAGCAGCCTCCCCTGTTTCAGCTACAACTATGCTGAATTTGAACTCTGTTCCTGAGCTTCAT

TTCTTTGATAACCCATTGAGGCAAAACTCAATCTTGCACCAACCAAATGCAAGTGGAAGAAAAAG

GGTTGTCCCTGAAACAGAAGACAATTCTACAGGGGATAGAAGAAATCAGAGGATGATCAAGAAC

AGAGAGTCTGCTGCTAGATCAAGAGCTAGAAAGCAGGTAAGTGACACTCAACTTTGTCTTAATCCT

GTCAATTTTGTGCTTATACATCAACTATGTTCCATATTGTTACTCTTTTGCTGCTTCTATTCTTGATT

TGAACAATATGCCGAGTTACTCTGTTTGCAG*GCTTATATGAACGAGTTGGAATCAGAAGTGG*

*TTAGTTGAAGAAAATGCAAGGCTCAAGAAGCAGCAGCAACAG*GTTCTCTTATCTTTCTTTATTTCTGT

CACTTTTAAAATTCAGTTTATAAAAAAAATGGATATAACTGATTCATAATAAATTGGTGTTTTCTTA

ATTTGTACAG*TTACGAGTAGATGCAGCTAATCAAGTTCCCAAAAAGAACACTCTTTATCGGACGTCA*

*ACTGCTC[[T]]ATTTTGA*GATCTTATTATAATTTGGTTTCCTAGTGCTACATTAGTATTAAGAACAATT

TCCCATTTGGCTGTATTTTGTTTGTAATATGCACCAACTGTTGTTTTGATGGTGGCCTTGTGGGGCG

ATGAATATTCGTATGACAAAATAAGAAGGGAAAAAATAGGTTGTGAATTAAGGAAAGTGTAGGCC

ATTATTAGTACTCTATCA

>ssp-610 genomic (mutation in brackets)

(SEQ ID NO: 26)

*ATGTGGTCATCAAGCAGTGATAACAGGGGACTCTCTGCTTCTTCTTCTTCATCTTCATCCTCATCTCA*

*TTCACCATTTTCTCCAAGACTCAAAACAATGGAAGAAGTGTGGAAAGATATTAATCTTTCTTCACTTC*

*AAGATCACACTACGAATTACTCTAGAGATCATCATCATCTTCATGATCATAATCATCAAGCTGCTAAT*

*TTTGGTGGAATGATTTTACAAGATTTTTTGGCAAGGCCTTTTGCTAATGAA*TCTTCACCAGCAGCAGC

AGCAGCAGCAGCCTCCCCTGTTTCAGCTACAACTATGCTGAATTTGAACTCTGTTCCTGAGCTTCAT

TTCTTTGATAACCCATTGAGGCAAAACTCAATCTTGCACCAACCAAATGCAAGTGGAAGAAAAAG

GGTTGTCCCTGAAACAGAAGACAATTCTACAGGGGATAGAAGAAATCAGAGGATGATCAAGAAC

AGAGAGTCTGCTGCTAGATCAAGAGCTAGAAAGCAGGTAAGTGACACTCAACTTTGTCTTAATCCT

GTCAATTTTGTGCTTATACATCAACTATGTTCCATATTGTTACTCTTTTGCTGCTTCTATTCTTGATT

TGAACAATATGCCGAGTTACTCTGTTTGCAG*GCTTATATGAACGAGTTGGAATCAGAAGTGGCACAT*

-continued

*TTAGTTGAAGAAAATGCAAGGCTCAAGAAGCAGCAGCAACAG*GTTCTCTTATCTTTCTTTATTTCTGT

CACTTTTAAAATTCAGTTTATAAAAAAAATGGATATAACTGATTCATAATAAATTGGTGTTTTCTTA

ATTTGTACAG*TTACGAGTAGATGCAGCTAATCAAGTTCCCAAAAAGAACACTCTTTATCGGACGTCA*

*A[[T]]TGCTCCATTTTGA*GATCTTATTATAATTTGGTTTCCTAGTGCTACATTAGTATTAAGAACAATT

TCCCATTTGGCTGTATTTTGTTTGTAATATGCACCAACTGTTGTTTTGATGGTGGCCTTGTGGGGCG

ATGAATATTCGTATGACAAAATAAGAAGGGAAAAAATAGGTTGTGAATTAAGGAAAGTGTAGGCC

ATTATTAGTACTCTATCA
* Marker: bold with underbar, * Exon: Italics and bold, * Deletion: :

>SFT (wild-type) genomic (SEQ ID NO: 16)

*ATGCCTAGAGAACGTGATCCTCTTGTTGTTGGTCGTGTGGTAGGGGATGTATTGGACCCTTTCACAA*

*GAACTATTGGCCTAAGAGTTATATATAGAGATAGAGAAGTTAATAATGGATGCGAGCTTAGGCCTTC*

*CCAAGTTATTAACCAGCCAAGGGTTGAAGTTGGAGGAGATGACCTACGTACCTTTTTCACTTTG*GTA

ATATTTCTTATATTTTTTGTTTGGGAATATAGTTAAGTTGATTTTCATAAGCAAAGTAAAAAGTATT

TTTGTCTTTTTGTAAAG*GTTATGGTGGACCCTGATGCTCCAAGTCCGAGTGATCCAAATCTGAGAGA*

*ATACCTTCACTG*GTCCGTATTTTTTCCTTATTCTCTCTTCTTTTCATCTCTTTCTTTTTTGACCTTTTTA

CTTAATTATATTCTTTAGTAATAATATATGATGATATCCTTTTTAAAAATTGGAAATACGAAAAGG

AGAAATGAAGAGGAGATTTACATGTGAGGGAGCAGATGGTAGAAATATATAAATGTGAAGATAT

ATATTCTTGAACTTAAAAACAAGCTACTAAAATAAAAATGAATAAAATATTTACTCTGTCAATATT

CTGTACTATATTGGTCAATGAATATTTATATTATTCATGACTTTAAAAATAGTCAAACGAGACATA

ACGTAAAAGTCAAAATACGTTTAAGCTCATTCATATAAATGAATATTTTTAAAATTTGTTGCATCC

ATCAAAATATCTACTTTTTAAGGAATGATATTTATTTCATAATATTCATATTTGATTCGTTGATGGA

TAGATTTTATTCTTTAAAAAATTAAATAAAAAAAATAAAATTGGCCTAGTCATATCCATCTAAAAT

GGGTGAGATTCTGGTACGCTGACCGTCTTATAATTCCCAATAAAAACTTTTGGAGAAAAAAGGGA

ACACAAAAAAATGAAGTAGTGCACCAATAGAATCACTTCTCACCTCCTTATAGCTAGTACGGATTA

TTCCCTTCATGTGTGCCACAGTCATGCACAATCCATATTATAATTTCCAAAATAATTAGTTGTTCAC

GTTTGAATTGATCATAAATGATATTACCATTTATCCTTTTTACTTATTAAGTAGATAGATTAAAAAA

TTTAAGATTTTCAAAAAGTTCTACATTTTTAAAAATAATCAATTGAAGGTATAAAAAAGTTGTCCT

TCCTTAATTTCTCAAGATGGATAAGTAATTAAGAACAACTAAAAAAAAGCGAACAAATAATTAGA

GATCGAATGAATATTTATCAATCCTCATTTCACCAAGTCATTAAATTATTTTATGACCAAAATGTTT

ACTCATTTTGCTTAAATATCAAGAAAATTGTTGAATTATTTCTTATAGAAATATCACTCAACATCAG

TATCTAAGTAGTACTCATTTCGTTTCTATTTATATATCATTTTTATTAAATATAAATGTTTTCTTGAT

ATTTATTTATTTCACAAAATCAAAATTTGACTTATGATTACTAAATAATTAATTTAATTTAATTAAT

CAAAATAAATTAATTTATCTCTTTTGCAAAAGTTAACTTTAAGAGAACACTAATTAAGAATATAAT

AATAAATTTAGTTAATTTTTTTAAAAGATATAAAATCTAAATTAGTGACATATAAATAGAAAGAGG

GGAAAGTAGTAGTTTAACTCTTATGGTTTGATAAGGTGTGTGCTAAATGACAACATCTTTCTTGTCT

CGTAAAGTTAACATCTTTGTAGGTGGTGAGTAAGTGAGTGAATGCCATTGAATGAAGAGATTATTT

GTTTTTGTCACCTTTACCACTAAAGTTTTGTCTATTTTTATTCTTCGAATTCCTCCAGTACAAGATTT

TATTTTTGATATTCCTTTCTTTGGAATTCAGTGTTGGTATAAATAGGATCTATTTGGCTATCCACAT

ATATTTTTAAATAAAAATCAGTATTTAGTCATTTAAATTACATTTCATGGATTATACTCGTTAAAAA

AAATATATTTAAGCAATTAAATATTATTTGTTGAACATAGGAAAAATGATTTGAAATATATTCAAA

-continued

CTTTGATCACAATTGTGATAACAATTTCAAATTTTGGGAAGGACCTTTTACCCCTTGCACTATTTAT

AGTATATTTTAAATGTATATATATGTCAACATAAATATAATAAATATTGCATTATTATATATAGTAA

CTTGTTCACGTGGATACATATATACCTGTAAAATATACTATTAAATAATATAGGAGATAGTAGGTC

CTGCTCAAAGTTAGAGATTGTTATAGCAATTTCGATCAAAGATATATTTCAAACTATTTTTCCTAAA

AGATATAACCAAATACAATTTTATCTTTAATTTCAATATTTGCAAATAAAGTGAAAAAATATTTAT

ACCAAGTAGGATGAATTAAAAATTAAGGGTTTTTTCCTCTTGTTATATATATAACTAATCGTCATT

TTTTTATTAATGAATCGTCGACAG*GTTGGTCACCGATATTCCAGCTACCACAGGTTCCAAGTTTTGGT*

GAGAATCCTCTTTTTGTTAATTGTTTGTTTGTTGTCTTCCCATGTTTACATTTTTTTAAAAAAAAACA

AACTAATTTTAAAGGTAGAATTAAAAAAAAATCATTATCGTATTTAAAAATATATTTTTATAATAA

TATGGACGAATAATATGAAACTAACAGAGTAATGACAAAGGAATTTATACTGAGCGGGCAATGTT

GCGTTAAATCATGTTTGTCCTAAACTTTTAAAACCTAGGAAAGGGAATGAAATCTATTCTCAATTA

ACGTGATTAAATATTCTAAACAATTGATATCCTTTAATTATGTCCCACACTACGCCAAAAGTTCTTA

AGCATTACACTCTAAAATTTGTATGCATAACATTAAAAGATCATTACCTATTTGGCTAAAATTTTTA

CAATAAGTTTATTTTAAAAAGTGTTCCTTTTTTTCCCCTCTCAAAAACACACTTGTGTTACTCTTGAT

TTTTCTCTCAAAAGTTTAGTTAAATACTTAAGTTTTTTTAAAATAATTTTTTTATGAAAAAAGAAAA

AAAACATTTTTGGCTAACCAAACAGGTTTAGGAGACTTGCGCTCTGCCATAAGTATTTCCCCATTC

ACTTTTCTTCCATTTTTATTTATGATTTTTTTTAACATATTAAGAAAGCTATTTGTTTCATGCTCTTC

AATAATTTCTTATTCTCCAAATTAACATAGATATTGTGGTAAAACACCATAATAGTTATTGTATATT

TGTATACCTTTTCAAATATATATACTCTCTAATAAGATCACAAGATAAAAAAACATTTATTGGTGA

ATAAATTTGACATAACTTTAATTTAATTATAACACAAAATTCAAAAGTTTTATTTCTCAACTTAAAA

<u>ATTTGGTGTCAAGTCAGAAGTAGATGTG</u>ATAATTTTTGTTTTTGAAATTGGAGGGAGTATCTTGT

TGAAAATATTGGATATGTACATAAGAAGTAGTCATTTGAAATGCATTGAAACTTGATAAAAACAT

AAGTAGCTAGCTAGTGCATGAAAGTTTGGTTGTTTATGTACTTTTAATATGTAG*GGCAAGAAATAGT*

*GAGCTATGAAAGTCCAAGACCATCAATGGGAATACATCGATTTGTATTTGTATTATTCAGACAATTAG*

*GTCGGCAAACAGTGTATGCTCCAGGATGGCGTCAGAATTTCAACACAAGAGATTTTGCAGAACTTTA*

*TAATCTTGGTTTACCTGTTGCTGCTGTCTATTTTAATTGTCAAAGAGAGAGTGGCAGTGGTGGACGTA*

*GAAGATCTGCTGATTGA*TCAACTCCATCTACTACAAAAAACAAAAAAACAATGATATTTTTAGCTA

ATAATAACCACCAATATCTACTACTTCTCTTACAACTTTAGTAGTATCTATAGTTATCTTTTTTAATC

TACTCTTTTACTTCTTTACTATATTGTCTTCCTCTCAATTTATTTGAATTAGTGACTTGATATCAAGT

TTCAATAAAGAAACAAAGACTGACTTTAGAATTTTGTGATTTACAATAAGTTGTACATATTTGTAT

GACTATCTTAAAAAGTTAAATCATTATTATTAAATATAAAAATATGATTAATTTAAAAGGAAGTAA

ATTATATAAAACGTTAATTTTTTTTTATAGTTTAGCTCTTAAAAAAAAATTATAACAATTAAAAGTA

TTGAATGAAAGAAGTTTGTAACTAGTCTCTGTTATTCCTCTATAAAACAGTATATTTTCTTGTTACT

TTTATAAATTTCTAAGATATGAACTTGAGT

>sft-1906 genomic(mutation in brackets)

(SEQ ID NO: 17)

ATGCCTAGAGAACGTGATCCTCTTGTTGTTGGTCGTGTGGTAGGGGATGTATTGGACCCTTTCACA

AGAACTATTGGCCTAAGAGTTATATATAGAGATAGAGAAGTTAATAATGGATGCGAGCTTAGGCC

TTCCCAAGTTATTAACCAGCCAAGGGTTGAAGTTGGAGGAGATGACCTACGTACCTTTTTCACTTT

GGTAATATTTCTTATATTTTTTGTTTGGGAATATAGTTAAGTTGATTTTCATAAGCAAAGTAAAAAG

TATTTTTGTCTTTTTGTAAAGGTTATGGTGGACCCTGATGCTCCAAGTCCGAGTGATCCAAATCTGA

-continued

GAGAATACCTTCACTGGTCCGTATTTTTTCCTTATTCTCTCTTCTTTTCATCTCTTTCTTTTTTGACCT

TTTTACTTAATTATATTCTTTAGTAATAATATATGATGATATCCTTTTTAAAAATTGGAAATACGAA

AAGGAGAAATGAAGAGGAGATTTACATGTGAGGGAGCAGATGGTAGAAATATATAAATGTGAAG

ATATATATTCTTGAACTTAAAAACAAGCTACTAAAATAAAAATGAATAAAATATTTACTCTGTCAA

TATTCTGTACTATATTGGTCAATGAATATTTATATTATTCATGACTTTAAAAATAGTCAAACGAGAC

ATAACGTAAAAGTCAAAATACGTTTAAGCTCATTCATATAAATGAATATTTTTAAAATTTGTTGCA

TCCATCAAAATATCTACTTTTTAAGGAATGATATTTATTTCATAATATTCATATTTGATTCGTTGAT

GGATAGATTTTATTCTTTAAAAAATTAAATAAAAAAAATAAAATTGGCCTAGTCATATCCATCTAA

AATGGGTGAGATTCTGGTACGCTGACCGTCTTATAATTCCCAATAAAAACTTTTGGAGAAAAAAGG

GAACACAAAAAAATGAAGTAGTGCACCAATAGAATCACTTCTCACCTCCTTATAGCTAGTACGGA

TTATTCCCTTCATGTGTGCCACAGTCATGCACAATCCATATTATAATTTCCAAAATAATTAGTTGTT

CACGTTTGAATTGATCATAAATGATATTACCATTTATCCTTTTTACTTATTAAGTAGATAGATTAAA

AAATTTAAGATTTTCAAAAAGTTCTACATTTTTAAAAATAATCAATTGAAGGTATAAAAAAGTTGT

CCTTCCTTAATTTCTCAAGATGGATAAGTAATTAAGAACAACTAAAAAAAAAGCGAACAAATAATT

AGAGATCGAATGAATATTTATCAATCCTCATTTCACCAAGTCATTAAATTATTTTATGACCAAAAT

GTTTACTCATTTTGCTTAAATATCAAGAAAATTGTTGAATTATTTCTTATAGAAATATCACTCAACA

TCAGTATCTAAGTAGTACTCATTTCGTTTCTATTTATATATCATTTTTATTAAATATAAATGTTTTCT

TGATATTTATTTATTTCACAAAATCAAAATTTGACTTATGATTACTAAATAATTAATTTAATTTAAT

TAATCAAAATAAATTAATTTATCTCTTTTGCAAAAGTTAACTTTAAGAGAACACTAATTAAGAATA

TAATAATAAATTTAGTTAATTTTTTTAAAAGATATAAAATCTAAATTAGTGACATATAAATAGAAA

GAGGGGAAAGTAGTAGTTTAACTCTTATGGTTTGATAAGGTGTGTGCTAAATGACAACATCTTTCT

TGTCTCGTAAAGTTAACATCTTTGTAGGTGGTGAGTAAGTGAGTGAATGCCATTGAATGAAGAGAT

TATTTGTTTTTGTCACCTTTACCACTAAAGTTTTGTCTATTTTTATTCTTCGAATTCCTCCAGTACAA

GATTTTATTTTTGATATTCCTTTCTTTGGAATTCAGTGTTGGTATAAATAGGATCTATTTGGCTATCC

ACATATATTTTTAAATAAAAATCAGTATTTAGTCATTTAAATTACATTTCATGGATTATACTCGTTA

AAAAAAATATATTTAAGCAATTAAATATTATTTGTTGAACATAGGAAAAATGATTTGAAATATATT

CAAACTTTGATCACAATTGTGATAACAATTTCAAATTTTGGGAAGGACCTTTTACCCCTTGCACTAT

TTATAGTATATTTTAAATGTATATATATGTCAACATAAATATAATAAATATTGCATTATTATATATA

GTAACTTGTTCACGTGGATACATATATACCTGTAAAATATACTATTAAATAATATAGGAGATAGTA

GGTCCTGCTCAAAGTTAGAGATTGTTATAGCAATTTCGATCAAAGATATATTTCAAACTATTTTTCC

TAAAAGATATAACCAAATACAATTTTATCTTTAATTTCAATATTTGCAAATAAAGTGAAAAAATAT

TTATACCAAGTAGGATGAATTAAAAATTAAGGGTTTTTTTCCTCTTGTTATATATATAACTAATCGT

CATTTTTTTATTAATGAATCGTCGACAGGTTGGTCACCGATATTCCAGCTACCACAGGTTCAAGTTT

TGGTGAGAATCCTCTTTTTGTTAATTGTTTGTTTGTTGTCTTCCCATGTTTACATTTTTTTAAAAAAA

AACAAACTAATTTTAAAGGTAGAATTAAAAAAAAATCATTATCGTATTTAAAAATATATTTTTATA

ATAATATGGACGAATAATATGAAACTAACAGAGTAATGACAAAGGAATTTATACTGAGCGGGCAA

TGTTGCGTTAAATCATGTTTGTCCTAAACTTTTAAAACCTAGGAAAGGGAATGAAATCTATTCTCA

ATTAACGTGATTAAATATTCTAAACAATTGATATCCTTTAATTATGTCCCACACTACGCCAAAAGTT

CTTAAGCATTACACTCTAAAATTTGTATGCATAACATTAAAAGATCATTACCTATTTGGCTAAAATT

-continued

```
TTTACAATAAGTTTATTTTAAAAAGTGTTCCTTTTTTTCCCCTCTCAAAAACACACTTGTGTTACTCT
TGATTTTTCTCTCAAAAGTTTAGTTAAATACTTAAGTTTTTTTAAAATAATTTTTTTATGAAAAAAG
AAAAAAAACATTTTTGGCTAACCAAACAGGTTTAGGAGACTTGCGCTCTGCCATAAGTATTTCCCC
ATTCACTTTTCTTCCATTTTTATTTATGATTTTTTTTAACATATTAAGAAAGCTATTTGTTTCATGCT
CTTCAATAATTTCTTATTCTCCAAATTAACATAGATATTGTGGTAAAACACCATAATAGTTATTGTA
TATTTGTATACCTTTTCAAATATATATACTCTCTAATAAGATCACAAGATAAAAAAACATTTATTGG
TGAATAAATTTGACATAACTTTAATTTAATTATAACACAAAATTCAAAAGTTTTATTTCTCAACTTA
AAAATTTGGTGTCAAGTCAGAAGTAGATGTGATAATTTTTGTTTTTGAAATTGGAGGGAGTATCT
TGTTGAAAATATTGGATATGTACATAAGAAGTAGTCATTTGAAATGCATTGAAACTTGATAAAAAC
ATAAGTAGCTAGCTAGTGCATGAAAGTTTGGTTGTTTATGTACTTTTAATATGTAGGGCAAGAAAT
AGTGAGCTATGAAAGTCCAAGACCATCAATGGGAATACATCGATTTGTATTTGTATTATTCAGACA
ATTAGGTCGGCAAACA[[A]]TGTATGCTCCAGGATGGCGTCAGAATTTCAACACAAGAGATTTTGCA
GAACTTTATAATCTTGGTTTACCTGTTGCTGCTGTCTATTTTAATTGTCAAAGAGAGAGTGGCAGTG
GTGGACGTAGAAGATCTGCTGATTGATCAACTCCATCTACTACAAAAAACAAAAAAACAATGATA
TTTTTAGCTAATAATAACCACCAATATCTACTACTTCTCTTACAACTTTAGTAGTATCTATAGTTAT
CTTTTTTAATCTACTCTTTTACTTCTTTACTATATTGTCTTCCTCTCAATTTATTTGAATTAGTGACTT
GATATCAAGTTTCAATAAAGAAACAAAGACTGACTTTAGAATTTTGTGATTTACAATAAGTTGTAC
ATATTTGTATGACTATCTTAAAAAGTTAAATCATTATTATTAAATATAAAAATATGATTAATTTAAA
AGGAAGTAAATTATATAAAACGTTAATTTTTTTTTATAGTTTAGCTCTTAAAAAAAAATTATAACA
ATTAAAAGTATTGAATGAAAGAAGTTTGTAACTAGTCTCTGTTATTCCTCTATAAAACAGTATATTT
TCTTGTTACTTTTATAAATTTCTAAGATATGAACTTGAGT
```

Without further elaboration, it is believed that one skilled in the art can, based on the above description, utilize the present disclosure to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A genetically-altered tomato plant homozygous for a mutant self-pruning (sp) gene and heterozygous for a mutant single flower truss (sft) gene, wherein the mutant sft gene encodes a mutant sft polypeptide comprising the amino acid sequence of SEQ ID NO: 21.

2. A genetically-altered tomato plant homozygous for a mutant self-pruning (sp) gene that encodes a mutant sp polypeptide comprising the amino acid sequence of SEQ ID NO: 10 and heterozygous for a mutant single flower truss (sft) gene comprising a coding sequence having the nucleic acid sequence of SEQ ID NO: 20.

3. A genetically-altered tomato plant homozygous for a mutant self-pruning (sp) gene and heterozygous for a mutant single flower truss (sft) gene, wherein the mutant sp gene comprises a coding sequence having the nucleic acid sequence of SEQ ID NO: 8 or a coding sequence at least 99% identical to SEQ ID NO: 8 and the mutant sft gene is sft-1906.

4. A genetically-altered tomato plant homozygous for a mutant self-pruning (sp) gene and heterozygous for a mutant single flower truss (sft) gene, wherein the mutant sft gene comprises a coding sequence having a mutation at position 394 of the nucleic acid sequence of SEQ ID NO: 18.

5. A genetically-altered tomato plant homozygous for a mutant self-pruning (sp) gene and heterozygous for a mutant single flower truss (sft) gene, wherein the mutant sft gene encodes a mutant sft polypeptide comprising an amino acid sequence having a mutation at position 132 of the amino acid sequence of SEQ ID NO: 19.

6. The genetically-altered tomato plant of claim 5, wherein the genetically-altered tomato plant is isogenic.

7. The genetically-altered tomato plant of claim 5, wherein the genetically-altered tomato plant is inbred.

8. A seed for producing the genetically-altered tomato plant of claim 5.

9. The genetically-altered tomato plant of claim 5, wherein the genetically-altered tomato plant has a sympodial index of between 1 and 3.

10. The genetically-altered tomato plant of claim 5, wherein the genetically-altered tomato plant has a sympodial index of between 1.5 and 2.5.

11. The genetically-altered tomato plant of claim 5, wherein the genetically-altered tomato plant has a sympodial index of less than 3.

12. The genetically-altered tomato plant of claim 5, wherein the genetically-altered tomato plant has a sympodial index of less than 2.5.

13. The genetically-altered tomato plant of claim 5, wherein the genetically-altered tomato plant has a sympodial index of less than 2.

14. The genetically-altered tomato plant of claim 5, wherein the genetically-altered tomato plant has a sympodial index of less than 1.

15. The genetically-altered tomato plant of claim 5, wherein the mutant sft gene encodes a mutant sft polypeptide that comprises a Val to Met mutation.

16. A genetically-altered tomato plant homozygous for a mutant self-pruning (sp) gene that comprises a coding sequence having the nucleic acid sequence of SEQ ID NO: 8 or a coding sequence having a nucleic acid sequence having at least 99% identity with the sequence of SEQ ID NO: 8 and heterozygous for a mutant single flower truss (sft) gene, wherein the mutant sft gene comprises a coding sequence having a nucleic acid sequence having at least 99% identity with the sequence of SEQ ID NO: 18 and a mutation at any position from position 379 through position 420 of the nucleic acid sequence of SEQ ID NO: 18, wherein the mutant sft gene coding sequence has a nucleic acid sequence having at least 95% identity with the sequence of SEQ ID NO: 18 from position 379 through position 420, and wherein the genetically-altered tomato plant exhibits: modified flowering time and shoot architecture, higher yield, higher brix, higher brix yield, higher red fruit yield, or any combination thereof, compared to a corresponding genetically-altered tomato plant homozygous for a mutant sp gene.

17. A genetically-altered tomato plant homozygous for a mutant self-pruning (sp) gene that comprises a coding sequence having the nucleic acid sequence of SEQ ID NO: 8 or a coding sequence having a nucleic acid sequence having at least 99% identity with the sequence of SEQ ID NO: 8 and heterozygous for a mutant single flower truss (sft) gene, wherein the mutant sft gene comprises a coding sequence having a nucleic acid sequence having at least 99% identity with the sequence of SEQ ID NO: 18 and a mutation at any position from position 379 through position 420 of the nucleic acid sequence of SEQ ID NO: 18, wherein the mutant sft gene coding sequence has a nucleic acid sequence having at least 97% identity with the sequence of SEQ ID NO: 18 from position 379 through position 420, and wherein the genetically-altered tomato plant exhibits: modified flowering time and shoot architecture, higher yield, higher brix, higher brix yield, higher red fruit yield, or any combination thereof, compared to a corresponding genetically-altered tomato plant homozygous for a mutant sp gene.

* * * * *

SEQUENCE LISTING

```
<160> NUMBER OF SEQ ID NOS: 26

<210> SEQ ID NO 1
<211> LENGTH: 654
<212> TYPE: DNA
<213> ORGANISM: S. lycopersicum

<400> SEQUENCE: 1

atgtggtcat caagcagtga taacagggga ctctctgctt cttcttcttc atcttcatcc     60

tcatctcatt caccattttc tccaagactc aaaacaatgg aagaagtgtg gaaagatatt    120

aatctttctt cacttcaaga tcacactacg aattactcta gagatcatca tcatcttcat    180

gatcataatc atcaagctgc taattttggt ggaatgattt tacaagattt tttggcaagg    240

ccttttgcta atgaatcttc accagcagca gcagcagcag cagcctcccc tgtttcagct    300

acaactatgc tgaatttgaa ctctgttcct gagcttcatt tctttgataa cccattgagg    360
```

caaaactcaa tcttgcacca accaaatgca agtggaagaa aaagggttgt ccctgaaaca 420
gaagacaatt ctacagggga tagaagaaat cagaggatga tcaagaacag agagtctgct 480
gctagatcaa gagctagaaa gcaggcttat atgaacgagt tggaatcaga agtggcacat 540
ttagttgaag aaaatgcaag gctcaagaag cagcagcaac agttacgagt agatgcagct 600
aatcaagttc ccaaaaagaa cactctttat cggacgtcaa ctgctccatt ttga 654

<210> SEQ ID NO 2
<211> LENGTH: 654
<212> TYPE: DNA
<213> ORGANISM: S. lycopersicum

<400> SEQUENCE: 2
atgtggtcat caagcagtga taacagggga ctctctgctt cttcttcttc atcttcatcc 60
tcatctcatt caccattttc tccaagactc aaaacaatgg aagaagtgtg gaaagatatt 120
aatctttctt cacttcaaga tcacactacg aattactcta gagatcatca tcatcttcat 180
gatcataatc atcaagctgc taattttggt ggaatgattt tacaagattt tttggcaagg 240
ccttttgcta atgaatcttc accagcagca gcagcagcag cagcctcccc tgtttcagct 300
acaactatgc tgaatttgaa ctctgttcct gagcttcatt tctttgataa cccattgagg 360
caaaactcaa tcttgcacca accaaatgca agtggaagaa aaagggttgt ccctgaaaca 420
gaagacaatt ctacagggga tagaagaaat cagaggatga tcaagaacag agagtctgct 480
gctagatcaa gagctagaaa gcaggcttat atgaacgagt tggaatcaga agtggcacat 540
ttagttgaag aaaatgcaag gctcaagaag cagcagcaac agttacgagt agatgcagct 600
aatcaagttc ccaaaaagaa cactctttat cggacgtcaa ctgctctatt ttga 654

<210> SEQ ID NO 3
<211> LENGTH: 654
<212> TYPE: DNA
<213> ORGANISM: S. lycopersicum

<400> SEQUENCE: 3
atgtggtcat caagcagtga taacagggga ctctctgctt cttcttcttc atcttcatcc 60
tcatctcatt caccattttc tccaagactc aaaacaatgg aagaagtgtg gaaagatatt 120
aatctttctt cacttcaaga tcacactacg aattactcta gagatcatca tcatcttcat 180
gatcataatc atcaagctgc taattttggt ggaatgattt tacaagattt tttggcaagg 240
ccttttgcta atgaatcttc accagcagca gcagcagcag cagcctcccc tgtttcagct 300
acaactatgc tgaatttgaa ctctgttcct gagcttcatt tctttgataa cccattgagg 360
caaaactcaa tcttgcacca accaaatgca agtggaagaa aaagggttgt ccctgaaaca 420
gaagacaatt ctacagggga tagaagaaat cagaggatga tcaagaacag agagtctgct 480
gctagatcaa gagctagaaa gcaggcttat atgaacgagt tggaatcaga agtggcacat 540
ttagttgaag aaaatgcaag gctcaagaag cagcagcaac agttacgagt agatgcagct 600
aatcaagttc ccaaaaagaa cactctttat cggacgtcaa ttgctccatt ttga 654

<210> SEQ ID NO 4
<211> LENGTH: 217
<212> TYPE: PRT
<213> ORGANISM: S. lycopersicum

<400> SEQUENCE: 4

Met Trp Ser Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
            20                  25                  30

Met Glu Glu Val Trp Lys Asp Ile Asn Leu Ser Ser Leu Gln Asp His
        35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
            100                 105                 110

His Phe Phe Asp Asn Pro Leu Arg Gln Asn Ser Ile Leu His Gln Pro
        115                 120                 125

Asn Ala Ser Gly Arg Lys Arg Val Val Pro Glu Thr Glu Asp Asn Ser
    130                 135                 140

Thr Gly Asp Arg Arg Asn Gln Arg Met Ile Lys Asn Arg Glu Ser Ala
145                 150                 155                 160

Ala Arg Ser Arg Ala Arg Lys Gln Ala Tyr Met Asn Glu Leu Glu Ser
                165                 170                 175

Glu Val Ala His Leu Val Glu Glu Asn Ala Arg Leu Lys Lys Gln Gln
            180                 185                 190

Gln Gln Leu Arg Val Asp Ala Ala Asn Gln Val Pro Lys Lys Asn Thr
        195                 200                 205

Leu Tyr Arg Thr Ser Thr Ala Pro Phe
    210                 215

<210> SEQ ID NO 5
<211> LENGTH: 217
<212> TYPE: PRT
<213> ORGANISM: S. lycopersicum

<400> SEQUENCE: 5

Met Trp Ser Ser Ser Ser Asp Asn Arg Gly Leu Ser Ala Ser Ser Ser
1               5                   10                  15

Ser Ser Ser Ser Ser Ser His Ser Pro Phe Ser Pro Arg Leu Lys Thr
            20                  25                  30

Met Glu Glu Val Trp Lys Asp Ile Asn Leu Ser Ser Leu Gln Asp His
        35                  40                  45

Thr Thr Asn Tyr Ser Arg Asp His His His Leu His Asp His Asn His
    50                  55                  60

Gln Ala Ala Asn Phe Gly Gly Met Ile Leu Gln Asp Phe Leu Ala Arg
65                  70                  75                  80

Pro Phe Ala Asn Glu Ser Ser Pro Ala Ala Ala Ala Ala Ala Ala Ser
                85                  90                  95

Pro Val Ser Ala Thr Thr Met Leu Asn Leu Asn Ser Val Pro Glu Leu
            100                 105                 110

His Phe Phe Asp Asn Pro Leu Arg Gln Asn Ser Ile Leu His Gln Pro
        115                 120                 125

Asn Ala Ser Gly Arg Lys Arg Val Val Pro Glu Thr Glu Asp Asn Ser
    130                 135                 140

Thr Gly Asp Arg Arg Asn Gln Arg Met Ile Lys Asn Arg Glu Ser Ala
145 150 155 160

Ala Arg Ser Arg Ala Arg Lys Gln Ala Tyr Met Asn Glu Leu Glu Ser
165 170 175

Glu Val Ala His Leu Val Glu Glu Asn Ala Arg Leu Lys Lys Gln Gln
180 185 190

Gln Gln Leu Arg Val Asp Ala Ala Asn Gln Val Pro Lys Lys Asn Thr
195 200 205

Leu Tyr Arg Thr Ser Thr Ala Leu Phe
210 215

<210> SEQ ID NO 6
<211> LENGTH: 217
<212> TYPE: PRT
<213> ORGANISM: S. lycopersicum

<400> SEQUENCE: 6

Met Trp Ser Ser Ser Ser Asp Asn Arg Gly Leu Ser Ala Ser Ser Ser
1 5 10 15

Ser Ser Ser Ser Ser Ser His Ser Pro Phe Ser Pro Arg Leu Lys Thr
20 25 30

Met Glu Glu Val Trp Lys Asp Ile Asn Leu Ser Ser Leu Gln Asp His
35 40 45

Thr Thr Asn Tyr Ser Arg Asp His His His Leu His Asp His Asn His
50 55 60

Gln Ala Ala Asn Phe Gly Gly Met Ile Leu Gln Asp Phe Leu Ala Arg
65 70 75 80

Pro Phe Ala Asn Glu Ser Ser Pro Ala Ala Ala Ala Ala Ala Ala Ser
85 90 95

Pro Val Ser Ala Thr Thr Met Leu Asn Leu Asn Ser Val Pro Glu Leu
100 105 110

His Phe Phe Asp Asn Pro Leu Arg Gln Asn Ser Ile Leu His Gln Pro
115 120 125

Asn Ala Ser Gly Arg Lys Arg Val Val Pro Glu Thr Glu Asp Asn Ser
130 135 140

Thr Gly Asp Arg Arg Asn Gln Arg Met Ile Lys Asn Arg Glu Ser Ala
145 150 155 160

Ala Arg Ser Arg Ala Arg Lys Gln Ala Tyr Met Asn Glu Leu Glu Ser
165 170 175

Glu Val Ala His Leu Val Glu Glu Asn Ala Arg Leu Lys Lys Gln Gln
180 185 190

Gln Gln Leu Arg Val Asp Ala Ala Asn Gln Val Pro Lys Lys Asn Thr
195 200 205

Leu Tyr Arg Thr Ser Ile Ala Pro Phe
210 215

<210> SEQ ID NO 7
<211> LENGTH: 528
<212> TYPE: DNA
<213> ORGANISM: S. lycopersicum

<400> SEQUENCE: 7
atggcttcca aaatgtgtga acccccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actgatcatg atagatccag atgttcctgg tcctagtgat 240
ccatatctca gggaacatct acactggatt gtcacagaca ttccaggcac tacagattgc 300
tcttttggaa gagaagtggt tgggtatgaa atgccaaggc caaatattgg aatccacagg 360
tttgtatttt tgctgtttaa gcagaagaaa aggcaaacaa tatcgagtgc accagtgtcc 420
agagatcaat ttagtagtag aaaattttca gaagaaaatg aacttggctc accagttgct 480
gctgttttct tcaattgtca gagggaaact gccgctagaa ggcgttga 528

<210> SEQ ID NO 8
<211> LENGTH: 528
<212> TYPE: DNA
<213> ORGANISM: S. lycopersicum

<400> SEQUENCE: 8
atggcttcca aaatgtgtga accccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actgatcatg atagatccag atgttcttgg tcctagtgat 240
ccatatctca gggaacatct acactggatt gtcacagaca ttccaggcac tacagattgc 300
tcttttggaa gagaagtggt tgggtatgaa atgccaaggc caaatattgg aatccacagg 360
tttgtatttt tgctgtttaa gcagaagaaa aggcaaacaa tatcgagtgc accagtgtcc 420
agagatcaat ttagtagtag aaaattttca gaagaaaatg aacttggctc accagttgct 480
gctgttttct tcaattgtca gagggaaact gccgctagaa ggcgttga 528

<210> SEQ ID NO 9
<211> LENGTH: 175
<212> TYPE: PRT
<213> ORGANISM: S. lycopersicum

<400> SEQUENCE: 9

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Val Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Ile Ser Ser Ala Pro Val Ser Arg Asp Gln Phe
    130                 135                 140

Ser Ser Arg Lys Phe Ser Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175
```

<210> SEQ ID NO 10
<211> LENGTH: 175
<212> TYPE: PRT
<213> ORGANISM: S. lycopersicum

<400> SEQUENCE: 10

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Leu Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Val Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Ile Ser Ser Ala Pro Val Ser Arg Asp Gln Phe
    130                 135                 140

Ser Ser Arg Lys Phe Ser Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175
```

<210> SEQ ID NO 11
<211> LENGTH: 7
<212> TYPE: PRT
<213> ORGANISM: S. lycopersicum

<400> SEQUENCE: 11

```
Arg Thr Ser Thr Ala Pro Phe
1               5
```

<210> SEQ ID NO 12
<211> LENGTH: 21
<212> TYPE: DNA
<213> ORGANISM: S. lycopersicum

<400> SEQUENCE: 12

```
cggacgtcaa ctgctctatt t                                              21
```

<210> SEQ ID NO 13
<211> LENGTH: 21
<212> TYPE: DNA
<213> ORGANISM: S. lycopersicum

<400> SEQUENCE: 13

```
cggacgtcaa ttgctccatt t                                              21
```

<210> SEQ ID NO 14
<211> LENGTH: 7
<212> TYPE: PRT
<213> ORGANISM: S. lycopersicum

<400> SEQUENCE: 14

Arg Thr Ser Thr Ala Leu Phe
1 5

<210> SEQ ID NO 15
<211> LENGTH: 7
<212> TYPE: PRT
<213> ORGANISM: S. lycopersicum

<400> SEQUENCE: 15

Arg Thr Ser Ile Ala Pro Phe
1 5

<210> SEQ ID NO 16
<211> LENGTH: 4297
<212> TYPE: DNA
<213> ORGANISM: S. lycopersicum

<400> SEQUENCE: 16
atgcctagag aacgtgatcc tcttgttgtt ggtcgtgtgg taggggatgt attggaccct 60
ttcacaagaa ctattggcct aagagttata tatagagata gagaagttaa taatggatgc 120
gagcttaggc cttcccaagt tattaaccag ccaagggttg aagttggagg agatgaccta 180
cgtacctttt tcactttggt aatatttctt atattttttg tttgggaata tagttaagtt 240
gattttcata agcaaagtaa aaagtatttt tgtctttttg taaaggttat ggtggaccct 300
gatgctccaa gtccgagtga tccaaatctg agagaatacc ttcactggtc cgtatttttt 360
ccttattctc tcttcttttc atctctttct tttttgacct ttttacttaa ttatattctt 420
tagtaataat atatgatgat atcctttttta aaaattggaa atacgaaaag gagaaatgaa 480
gaggagattt acatgtgagg gagcagatgg tagaaatata taaatgtgaa gatatatatt 540
cttgaactta aaaacaagct actaaaataa aaatgaataa aatatttact ctgtcaatat 600
tctgtactat attggtcaat gaatatttat attattcatg actttaaaaa tagtcaaacg 660
agacataacg taaaagtcaa aatacgttta agctcattca tataaatgaa tatttttaaa 720
atttgttgca tccatcaaaa tatctacttt ttaaggaatg atatttattt cataatattc 780
atatttgatt cgttgatgga tagattttat tctttaaaaa attaaataaa aaaaataaaa 840
ttggcctagt catatccatc taaaatgggt gagattctgg tacgctgacc gtcttataat 900
tcccaataaa aacttttgga gaaaaaaggg aacacaaaaa aatgaagtag tgcaccaata 960
gaatcacttc tcacctcctt atagctagta cggattattc ccttcatgtg tgccacagtc 1020
atgcacaatc catattataa tttccaaaat aattagttgt tcacgtttga attgatcata 1080
aatgatatta ccatttatcc tttttactta ttaagtagat agattaaaaa atttaagatt 1140
ttcaaaaagt tctacatttt taaaaataat caattgaagg tataaaaaag ttgtccttcc 1200
ttaatttctc aagatggata agtaattaag aacaactaaa aaaaagcgaa caaataatta 1260
gagatcgaat gaatatttat caatcctcat ttcaccaagt cattaaatta ttttatgacc 1320
aaaatgttta ctcattttgc ttaaatatca agaaaattgt tgaattattt cttatagaaa 1380
tatcactcaa catcagtatc taagtagtac tcatttcgtt tctatttata tatcattttt 1440
attaaatata aatgttttct tgatatttat ttatttcaca aaatcaaaat ttgacttatg 1500
attactaaat aattaattta atttaattaa tcaaaataaa ttaatttatc tcttttgcaa 1560
aagttaactt taagagaaca ctaattaaga atataataat aaatttagtt aattttttta 1620
aaagatataa aatctaaatt agtgacatat aaatagaaag aggggaaagt agtagtttaa 1680

-continued

```
ctcttatggt ttgataaggt gtgtgctaaa tgacaacatc tttcttgtct cgtaaagtta   1740
acatctttgt aggtggtgag taagtgagtg aatgccattg aatgaagaga ttatttgttt   1800
ttgtcacctt taccactaaa gttttgtcta tttttattct tcgaattcct ccagtacaag   1860
attttatttt tgatattcct ttctttggaa ttcagtgttg gtataaatag gatctatttg   1920
gctatccaca tatattttta aataaaaatc agtatttagt catttaaatt acatttcatg   1980
gattatactc gttaaaaaaa atatatttaa gcaattaaat attatttgtt gaacatagga   2040
aaaatgattt gaaatatatt caaactttga tcacaattgt gataacaatt tcaaattttg   2100
ggaaggacct tttacccctt gcactattta tagtatattt taaatgtata tatatgtcaa   2160
cataaatata ataaatattg cattattata tatagtaact tgttcacgtg gatacatata   2220
tacctgtaaa atatactatt aaataatata ggagatagta ggtcctgctc aaagttagag   2280
attgttatag caatttcgat caaagatata tttcaaacta tttttcctaa aagatataac   2340
caaatacaat tttatcttta atttcaatat ttgcaaataa agtgaaaaaa tatttatacc   2400
aagtaggatg aattaaaaat taagggtttt tttcctcttg ttatatatat aactaatcgt   2460
catttttta ttaatgaatc gtcgacaggt tggtcaccga tattccagct accacaggtt   2520
caagttttgg tgagaatcct ctttttgtta attgtttgtt tgttgtcttc ccatgtttac   2580
atttttttaa aaaaaaacaa actaatttta aaggtagaat taaaaaaaaa tcattatcgt   2640
atttaaaaat atatttttat aataatatgg acgaataata tgaaactaac agagtaatga   2700
caaaggaatt tatactgagc gggcaatgtt gcgttaaatc atgtttgtcc taaactttta   2760
aaacctagga aagggaatga aatctattct caattaacgt gattaaatat tctaaacaat   2820
tgatatcctt taattatgtc ccacactacg ccaaaagttc ttaagcatta cactctaaaa   2880
tttgtatgca taacattaaa agatcattac ctatttggct aaaattttta caataagttt   2940
attttaaaaa gtgttccttt ttttcccctc tcaaaaacac acttgtgtta ctcttgattt   3000
ttctctcaaa agtttagtta aatacttaag tttttttaaa ataatttttt tatgaaaaaa   3060
gaaaaaaaac atttttggct aaccaaacag gtttaggaga cttgcgctct gccataagta   3120
tttccccatt cacttttctt ccatttttat ttatgatttt ttttaacata ttaagaaagc   3180
tatttgtttc atgctcttca ataatttctt attctccaaa ttaacataga tattgtggta   3240
aaacaccata atagttattg tatatttgta taccttttca aatatatata ctctctaata   3300
agatcacaag ataaaaaaac atttattggt gaataaattt gacataactt taatttaatt   3360
ataacacaaa attcaaaagt tttatttctc aacttaaaaa tttggtgtca agtcagaagt   3420
agatgtgata atttttgttt ttgaaattgg agggagtatc ttgttgaaaa tattggatat   3480
gtacataaga agtagtcatt tgaaatgcat tgaaacttga taaaaacata agtagctagc   3540
tagtgcatga aagtttggtt gtttatgtac ttttaatatg tagggcaaga aatagtgagc   3600
tatgaaagtc caagaccatc aatgggaata catcgatttg tatttgtatt attcagacaa   3660
ttaggtcggc aaacagtgta tgctccagga tggcgtcaga atttcaacac aagagatttt   3720
gcagaacttt ataatcttgg tttacctgtt gctgctgtct attttaattg tcaaagagag   3780
agtggcagtg gtggacgtag aagatctgct gattgatcaa ctccatctac tacaaaaaac   3840
aaaaaaacaa tgatattttt agctaataat aaccaccaat atctactact tctcttacaa   3900
ctttagtagt atctatagtt atcttttta atctactctt ttacttcttt actatattgt   3960
cttcctctca atttatttga attagtgact tgatatcaag tttcaataaa gaaacaaaga   4020
```

```
ctgactttag aattttgtga tttacaataa gttgtacata tttgtatgac tatcttaaaa   4080

agttaaatca ttattattaa atataaaaat atgattaatt taaaaggaag taaattatat   4140

aaaacgttaa ttttttttta tagtttagct cttaaaaaaa aattataaca attaaaagta   4200

ttgaatgaaa gaagtttgta actagtctct gttattcctc tataaaacag tatattttct   4260

tgttactttt ataaatttct aagatatgaa cttgagt                            4297
```

<210> SEQ ID NO 17
<211> LENGTH: 4297
<212> TYPE: DNA
<213> ORGANISM: S. lycopersicum

<400> SEQUENCE: 17

```
atgcctagag aacgtgatcc tcttgttgtt ggtcgtgtgg taggggatgt attggaccct     60

ttcacaagaa ctattggcct aagagttata tatagagata gagaagttaa taatggatgc    120

gagcttaggc cttcccaagt tattaaccag ccaagggttg aagttggagg agatgaccta    180

cgtacctttt tcactttggt aatatttctt atatttttg tttgggaata tagttaagtt    240

gattttcata agcaaagtaa aaagtatttt tgtctttttg taaaggttat ggtggaccct    300

gatgctccaa gtccgagtga tccaaatctg agagaatacc ttcactggtc cgtatttttt    360

ccttattctc tcttcttttc atctctttct tttttgacct ttttacttaa ttatattctt    420

tagtaataat atatgatgat atccttttta aaaattggaa atacgaaaag gagaaatgaa    480

gaggagattt acatgtgagg gagcagatgg tagaaatata taaatgtgaa gatatatatt    540

cttgaactta aaaacaagct actaaaataa aaatgaataa aatatttact ctgtcaatat    600

tctgtactat attggtcaat gaatatttat attattcatg actttaaaaa tagtcaaacg    660

agacataacg taaaagtcaa aatacgttta agctcattca tataaatgaa tatttttaaa    720

atttgttgca tccatcaaaa tatctacttt ttaaggaatg atatttattt cataatattc    780

atatttgatt cgttgatgga tagattttat tctttaaaaa attaaataaa aaaaataaaa    840

ttggcctagt catatccatc taaaatgggt gagattctgg tacgctgacc gtcttataat    900

tcccaataaa aacttttgga gaaaaaaggg aacacaaaaa aatgaagtag tgcaccaata    960

gaatcacttc tcacctcctt atagctagta cggattattc ccttcatgtg tgccacagtc   1020

atgcacaatc catattataa tttccaaaat aattagttgt tcacgtttga attgatcata   1080

aatgatatta ccatttatcc tttttactta ttaagtagat agattaaaaa atttaagatt   1140

ttcaaaaagt tctacatttt taaaaataat caattgaagg tataaaaaag ttgtccttcc   1200

ttaatttctc aagatggata agtaattaag aacaactaaa aaaaagcgaa caaataatta   1260

gagatcgaat gaatatttat caatcctcat ttcaccaagt cattaaatta ttttatgacc   1320

aaaatgttta ctcattttgc ttaaatatca agaaaattgt tgaattattt cttatagaaa   1380

tatcactcaa catcagtatc taagtagtac tcatttcgtt tctatttata tatcattttt   1440

attaaatata aatgttttct tgatatttat ttatttcaca aaatcaaaat ttgacttatg   1500

attactaaat aattaattta atttaattaa tcaaaataaa ttaatttatc tcttttgcaa   1560

aagttaactt taagagaaca ctaattaaga atataataat aaatttagtt aattttttta   1620

aaagatataa aatctaaatt agtgacatat aaatagaaag aggggaaagt agtagtttaa   1680

ctcttatggt ttgataaggt gtgtgctaaa tgacaacatc tttcttgtct cgtaaagtta   1740

acatctttgt aggtggtgag taagtgagtg aatgccattg aatgaagaga ttatttgttt   1800

ttgtcacctt taccactaaa gttttgtcta tttttattct tcgaattcct ccagtacaag   1860
```

```
attttatttt tgatattcct ttctttggaa ttcagtgttg gtataaatag gatctatttg   1920
gctatccaca tatattttta aataaaaatc agtatttagt catttaaatt acatttcatg   1980
gattatactc gttaaaaaaa atatatttaa gcaattaaat attatttgtt gaacatagga   2040
aaaatgattt gaaatatatt caaactttga tcacaattgt gataacaatt tcaaattttg   2100
ggaaggacct tttacccctt gcactattta tagtatattt taaatgtata tatatgtcaa   2160
cataaatata ataaatattg cattattata tatagtaact tgttcacgtg gatacatata   2220
tacctgtaaa atatactatt aaataatata ggagatagta ggtcctgctc aaagttagag   2280
attgttatag caatttcgat caaagatata tttcaaacta tttttcctaa aagatataac   2340
caaatacaat tttatcttta atttcaatat ttgcaaataa agtgaaaaaa tatttatacc   2400
aagtaggatg aattaaaaat taagggtttt tttcctcttg ttatatatat aactaatcgt   2460
cattttttta ttaatgaatc gtcgacaggt tggtcaccga tattccagct accacaggtt   2520
caagttttgg tgagaatcct ctttttgtta attgtttgtt tgttgtcttc ccatgtttac   2580
atttttttaa aaaaaaacaa actaatttta aaggtagaat taaaaaaaaa tcattatcgt   2640
atttaaaaat atatttttat aataatatgg acgaataata tgaaactaac agagtaatga   2700
caaaggaatt tatactgagc gggcaatgtt gcgttaaatc atgtttgtcc taaactttta   2760
aaacctagga aagggaatga aatctattct caattaacgt gattaaatat tctaaacaat   2820
tgatatcctt taattatgtc ccacactacg ccaaaagttc ttaagcatta cactctaaaa   2880
tttgtatgca taacattaaa agatcattac ctatttggct aaaattttta caataagttt   2940
atttaaaaaa gtgttccttt ttttcccctc tcaaaaacac acttgtgtta ctcttgattt   3000
ttctctcaaa agtttagtta aatacttaag ttttttttaaa ataatttttt tatgaaaaaa   3060
gaaaaaaaac atttttggct aaccaaacag gtttaggaga cttgcgctct gccataagta   3120
tttccccatt cacttttctt ccatttttat ttatgatttt ttttaacata ttaagaaagc   3180
tatttgtttc atgctcttca ataatttctt attctccaaa ttaacataga tattgtggta   3240
aaacaccata atagttattg tatatttgta taccttttca aatatatata ctctctaata   3300
agatcacaag ataaaaaaac atttattggt gaataaattt gacataactt taatttaatt   3360
ataacacaaa attcaaaagt tttatttctc aacttaaaaa tttggtgtca agtcagaagt   3420
agatgtgata atttttgttt ttgaaattgg agggagtatc ttgttgaaaa tattggatat   3480
gtacataaga agtagtcatt tgaaatgcat tgaaacttga taaaaacata agtagctagc   3540
tagtgcatga aagtttggtt gtttatgtac ttttaatatg tagggcaaga aatagtgagc   3600
tatgaaagtc caagaccatc aatgggaata catcgatttg tatttgtatt attcagacaa   3660
ttaggtcggc aaacaatgta tgctccagga tggcgtcaga atttcaacac aagagatttt   3720
gcagaacttt ataatcttgg tttacctgtt gctgctgtct attttaattg tcaaagagag   3780
agtggcagtg gtggacgtag aagatctgct gattgatcaa ctccatctac tacaaaaaac   3840
aaaaaaacaa tgatattttt agctaataat aaccaccaat atctactact tctcttacaa   3900
ctttagtagt atctatagtt atctttttta atctactctt ttacttcttt actatattgt   3960
cttcctctca atttatttga attagtgact tgatatcaag tttcaataaa gaaacaaaga   4020
ctgactttag aattttgtga tttacaataa gttgtacata tttgtatgac tatcttaaaa   4080
agttaaatca ttattattaa atataaaaat atgattaatt taaaaggaag taaattatat   4140
aaaacgttaa ttttttttta tagtttagct cttaaaaaaa aattataaca attaaaagta   4200
```

-continued

```
ttgaatgaaa gaagtttgta actagtctct gttattcctc tataaaacag tatattttct   4260

tgttactttt ataaatttct aagatatgaa cttgagt                            4297


<210> SEQ ID NO 18
<211> LENGTH: 534
<212> TYPE: DNA
<213> ORGANISM: S. lycopersicum

<400> SEQUENCE: 18

atgcctagag aacgtgatcc tcttgttgtt ggtcgtgtgg taggggatgt attggaccct     60

ttcacaagaa ctattggcct aagagttata tatagagata gagaagttaa taatggatgc    120

gagcttaggc cttcccaagt tattaaccag ccaagggttg aagttggagg agatgaccta    180

cgtacctttt tcactttggt tatggtggac cctgatgctc caagtccgag tgatccaaat    240

ctgagagaat accttcactg gttggtcacc gatattccag ctaccacagg ttcaagtttt    300

gggcaagaaa tagtgagcta tgaaagtcca agaccatcaa tgggaataca tcgatttgta    360

tttgtattat tcagacaatt aggtcggcaa acagtgtatg ctccaggatg gcgtcagaat    420

ttcaacacaa gagattttgc agaactttat aatcttggtt tacctgttgc tgctgtctat    480

tttaattgtc aaagagagag tggcagtggt ggacgtagaa gatctgctga ttga          534


<210> SEQ ID NO 19
<211> LENGTH: 177
<212> TYPE: PRT
<213> ORGANISM: S. lycopersicum

<400> SEQUENCE: 19

Met Pro Arg Glu Arg Asp Pro Leu Val Val Gly Arg Val Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Asp Leu Arg Thr Phe Phe
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Leu Tyr Asn Leu Gly Leu Pro Val Ala Ala Val Tyr
145                 150                 155                 160

Phe Asn Cys Gln Arg Glu Ser Gly Ser Gly Gly Arg Arg Arg Ser Ala
                165                 170                 175

Asp


<210> SEQ ID NO 20
<211> LENGTH: 534
<212> TYPE: DNA
<213> ORGANISM: S. lycopersicum
```

<400> SEQUENCE: 20
atgcctagag aacgtgatcc tcttgttgtt ggtcgtgtgg taggggatgt attggaccct 60
ttcacaagaa ctattggcct aagagttata tatagagata gagaagttaa taatggatgc 120
gagcttaggc cttcccaagt tattaaccag ccaagggttg aagttggagg agatgaccta 180
cgtacctttt tcactttggt tatggtggac cctgatgctc caagtccgag tgatccaaat 240
ctgagagaat accttcactg gttggtcacc gatattccag ctaccacagg ttcaagtttt 300
gggcaagaaa tagtgagcta tgaaagtcca agaccatcaa tgggaataca tcgatttgta 360
tttgtattat tcagacaatt aggtcggcaa acaatgtatg ctccaggatg gcgtcagaat 420
ttcaacacaa gagattttgc agaactttat aatcttggtt tacctgttgc tgctgtctat 480
tttaattgtc aaagagagag tggcagtggt ggacgtagaa gatctgctga ttga 534

<210> SEQ ID NO 21
<211> LENGTH: 177
<212> TYPE: PRT
<213> ORGANISM: S. lycopersicum

<400> SEQUENCE: 21

Met Pro Arg Glu Arg Asp Pro Leu Val Val Gly Arg Val Val Gly Asp
1 5 10 15

Val Leu Asp Pro Phe Thr Arg Thr Ile Gly Leu Arg Val Ile Tyr Arg
20 25 30

Asp Arg Glu Val Asn Asn Gly Cys Glu Leu Arg Pro Ser Gln Val Ile
35 40 45

Asn Gln Pro Arg Val Glu Val Gly Gly Asp Asp Leu Arg Thr Phe Phe
50 55 60

Thr Leu Val Met Val Asp Pro Asp Ala Pro Ser Pro Ser Asp Pro Asn
65 70 75 80

Leu Arg Glu Tyr Leu His Trp Leu Val Thr Asp Ile Pro Ala Thr Thr
85 90 95

Gly Ser Ser Phe Gly Gln Glu Ile Val Ser Tyr Glu Ser Pro Arg Pro
100 105 110

Ser Met Gly Ile His Arg Phe Val Phe Val Leu Phe Arg Gln Leu Gly
115 120 125

Arg Gln Thr Met Tyr Ala Pro Gly Trp Arg Gln Asn Phe Asn Thr Arg
130 135 140

Asp Phe Ala Glu Leu Tyr Asn Leu Gly Leu Pro Val Ala Ala Val Tyr
145 150 155 160

Phe Asn Cys Gln Arg Glu Ser Gly Ser Gly Gly Arg Arg Arg Ser Ala
165 170 175

Asp

<210> SEQ ID NO 22
<211> LENGTH: 1930
<212> TYPE: DNA
<213> ORGANISM: S. lycopersicum

<400> SEQUENCE: 22
atggcttcca aaatgtgtga accccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actggtatat attaatcttc aacacttcca atttactccg 240

-continued

```
tctgtctgtc ctaatttatg tcacacattt tctatgatat atagttttag aaattattca    300

agaccataac tttttaaaga aaaaatcata gactttctta gtcaacgtca aataaattga    360

gacggacaag atgacatgat tagtacattt atcttctatt attgacctct cattttcttt    420

tatacattat ttgacagatc atgatagatc cagatgttcc tggtcctagt gatccatatc    480

tcagggaaca tctacactgg tatagacaac atatgcctta aaactaactc agtcaatttt    540

atcttcaatt gtttactttg gaaggggaaa tgacatgatc attatatcat agtacaaatt    600

attatgtaat ttctgttcgt ctaaaaaatg tcactttaga aaaaactgat aatcatatac    660

aataccacaa taaagataga agaacatgta ctaatattga acttaaataa tgagtactag    720

gagtattatt aattaacttt aaaaatgcta gtcaatatac ctatgtttat atgttaaaaa    780

atcctttata tttggaaaca tgagtactcc tataccatac aatgttgtcg tacagttgat    840

tagacgggca aattaaacaa atgtccaata attgtactaa ttaataacta cttgttctct    900

tcatctatta ttagttatta ccaaaaaaag aggactgcaa aatggtgata ttattatgtg    960

taacggaaaa aaacgtactc tatttaatat gatagaatca aagtgacata ttttgttcta   1020

gttagacaaa taagtaactg aaaagaggat ttgaccatct ttacaggatt gtcacagaca   1080

ttccaggcac tacagattgc tcttttggta tgtatcctta acccataaat caaaataatg   1140

tactttcttt ttatttgcca ttaatatctc tagtacaaaa aagaaatatt ataaaaaaaa   1200

ttaatttcaa tttttatatt ataggtttaa gataataata ttaaacgata ttttagtctc   1260

taccaaatag acgagcaaat taaaactaag aaagcactac atgttttctt tatattatta   1320

gtataaaaat atattataat ttgcctggtg gtaataggat caaagtattg attcttaatt   1380

attattatat aattaataat aatggtaaac aaaaagatat aaagtgctta cctcctaatt   1440

ccctatatga aaaaatatac ttacttaatt actcttttta cacgtaagca tgcatttaaa   1500

aaaatattaa aaaattattc cagaggttat atataatatg tatggataaa aaaaaaattc   1560

acctatatac ataataatat aattttcgag tgaattgacc gcccttcagc atcattatat   1620

aatgttatcg atctaggtct ttgtgtgaaa ttaaaagtta tttatacggt tagtacgatc   1680

gcgtaataac gaaggtaaaa atatttcagg aagagaagtg gttgggtatg aaatgccaag   1740

gccaaatatt ggaatccaca ggtttgtatt tttgctgttt aagcagaaga aaaggcaaac   1800

aatatcgagt gcaccagtgt ccagagatca atttagtagt agaaaatttt cagaagaaaa   1860

tgaacttggc tcaccagttg ctgctgtttt cttcaattgt cagagggaaa ctgccgctag   1920

aaggcgttga                                                          1930
```

<210> SEQ ID NO 23
<211> LENGTH: 1930
<212> TYPE: DNA
<213> ORGANISM: S. lycopersicum

<400> SEQUENCE: 23

```
atggcttcca aaatgtgtga accccttgtg attggtagag tgattggtga agttgttgat     60

tatttctgtc caagtgttaa gatgtctgtt gtttataaca acaacaaaca tgtctataat    120

ggacatgaat tctttccttc ctcagtaact tctaaaccta gggttgaagt tcatggtggt    180

gatctcagat ccttcttcac actggtatat attaatcttc aacacttcca atttactccg    240

tctgtctgtc ctaatttatg tcacacattt tctatgatat atagttttag aaattattca    300

agaccataac tttttaaaga aaaaatcata gactttctta gtcaacgtca aataaattga    360

gacggacaag atgacatgat tagtacattt atcttctatt attgacctct cattttcttt    420
```

```
tatacattat ttgacagatc atgatagatc cagatgttct tggtcctagt gatccatatc    480
tcagggaaca tctacactgg tatagacaac atatgcctta aaactaactc agtcaatttt    540
atcttcaatt gtttactttg gaaggggaaa tgacatgatc attatatcat agtacaaatt    600
attatgtaat ttctgttcgt ctaaaaaatg tcactttaga aaaaactgat aatcatatac    660
aataccacaa taaagataga agaacatgta ctaatattga acttaaataa tgagtactag    720
gagtattatt aattaacttt aaaaatgcta gtcaatatac ctatgtttat atgttaaaaa    780
atcctttata tttggaaaca tgagtactcc tataccatac aatgttgtcg tacagttgat    840
tagacgggca aattaaacaa atgtccaata attgtactaa ttaataacta cttgttctct    900
tcatctatta ttagttatta ccaaaaaaag aggactgcaa aatggtgata ttattatgtg    960
taacggaaaa aaacgtactc tatttaatat gatagaatca aagtgacata ttttgttcta   1020
gttagacaaa taagtaactg aaaagaggat ttgaccatct ttacaggatt gtcacagaca   1080
ttccaggcac tacagattgc tcttttggta tgtatcctta acccataaat caaaataatg   1140
tactttcttt ttatttgcca ttaatatctc tagtacaaaa aagaaatatt ataaaaaaaa   1200
ttaatttcaa tttttatatt ataggtttaa gataataata ttaaacgata ttttagtctc   1260
taccaaatag acgagcaaat taaaactaag aaagcactac atgttttctt tatattatta   1320
gtataaaaat atattataat ttgcctggtg gtaataggat caaagtattg attcttaatt   1380
attattatat aattaataat aatggtaaac aaaaagatat aaagtgctta cctcctaatt   1440
ccctatatga aaaaatatac ttacttaatt actcttttta cacgtaagca tgcatttaaa   1500
aaaatattaa aaaattattc cagaggttat atataatatg tatggataaa aaaaaaattc   1560
acctatatac ataataatat aattttcgag tgaattgacc gcccttcagc atcattatat   1620
aatgttatcg atctaggtct ttgtgtgaaa ttaaaagtta tttatacggt tagtacgatc   1680
gcgtaataac gaaggtaaaa atatttcagg aagagaagtg gttgggtatg aaatgccaag   1740
gccaaatatt ggaatccaca ggtttgtatt tttgctgttt aagcagaaga aaaggcaaac   1800
aatatcgagt gcaccagtgt ccagagatca atttagtagt agaaaatttt cagaagaaaa   1860
tgaacttggc tcaccagttg ctgctgtttt cttcaattgt cagagggaaa ctgccgctag   1920
aaggcgttga                                                          1930
```

<210> SEQ ID NO 24
<211> LENGTH: 1087
<212> TYPE: DNA
<213> ORGANISM: S. lycopersicum

<400> SEQUENCE: 24

```
atgtggtcat caagcagtga taacagggga ctctctgctt cttcttcttc atcttcatcc     60
tcatctcatt caccattttc tccaagactc aaaacaatgg aagaagtgtg gaaagatatt    120
aatctttctt cacttcaaga tcacactacg aattactcta gagatcatca tcatcttcat    180
gatcataatc atcaagctgc taattttggt ggaatgattt tacaagattt tttggcaagg    240
ccttttgcta atgaatcttc accagcagca gcagcagcag cagcctcccc tgtttcagct    300
acaactatgc tgaatttgaa ctctgttcct gagcttcatt tctttgataa cccattgagg    360
caaaactcaa tcttgcacca accaaatgca agtggaagaa aaagggttgt ccctgaaaca    420
gaagacaatt ctacagggga tagaagaaat cagaggatga tcaagaacag agagtctgct    480
gctagatcaa gagctagaaa gcaggtaagt gacactcaac tttgtcttaa tcctgtcaat    540
```

-continued

```
tttgtgctta tacatcaact atgttccata ttgttactct tttgctgctt ctattcttga    600

tttgaacaat atgccgagtt actctgtttg caggcttata tgaacgagtt ggaatcagaa    660

gtggcacatt tagttgaaga aaatgcaagg ctcaagaagc agcagcaaca ggttctctta    720

tctttcttta tttctgtcac ttttaaaatt cagtttataa aaaaaatgga tataactgat    780

tcataataaa ttggtgtttt cttaatttgt acagttacga gtagatgcag ctaatcaagt    840

tcccaaaaag aacactcttt atcggacgtc aactgctcca ttttgagatc ttattataat    900

ttggtttcct agtgctacat tagtattaag aacaatttcc catttggctg tattttgttt    960

gtaatatgca ccaactgttg ttttgatggt ggccttgtgg ggcgatgaat attcgtatga   1020

caaaataaga agggaaaaaa taggttgtga attaaggaaa gtgtaggcca ttattagtac   1080

tctatca                                                             1087
```

<210> SEQ ID NO 25
<211> LENGTH: 1087
<212> TYPE: DNA
<213> ORGANISM: S. lycopersicum

<400> SEQUENCE: 25

```
atgtggtcat caagcagtga taacagggga ctctctgctt cttcttcttc atcttcatcc     60

tcatctcatt caccattttc tccaagactc aaaacaatgg aagaagtgtg gaaagatatt    120

aatctttctt cacttcaaga tcacactacg aattactcta gagatcatca tcatcttcat    180

gatcataatc atcaagctgc taattttggt ggaatgattt tacaagattt tttggcaagg    240

ccttttgcta atgaatcttc accagcagca gcagcagcag cagcctcccc tgtttcagct    300

acaactatgc tgaatttgaa ctctgttcct gagcttcatt tctttgataa cccattgagg    360

caaaactcaa tcttgcacca accaaatgca agtggaagaa aaagggttgt ccctgaaaca    420

gaagacaatt ctacagggga tagaagaaat cagaggatga tcaagaacag agagtctgct    480

gctagatcaa gagctagaaa gcaggtaagt gacactcaac tttgtcttaa tcctgtcaat    540

tttgtgctta tacatcaact atgttccata ttgttactct tttgctgctt ctattcttga    600

tttgaacaat atgccgagtt actctgtttg caggcttata tgaacgagtt ggaatcagaa    660

gtggcacatt tagttgaaga aaatgcaagg ctcaagaagc agcagcaaca ggttctctta    720

tctttcttta tttctgtcac ttttaaaatt cagtttataa aaaaaatgga tataactgat    780

tcataataaa ttggtgtttt cttaatttgt acagttacga gtagatgcag ctaatcaagt    840

tcccaaaaag aacactcttt atcggacgtc aactgctcta ttttgagatc ttattataat    900

ttggtttcct agtgctacat tagtattaag aacaatttcc catttggctg tattttgttt    960

gtaatatgca ccaactgttg ttttgatggt ggccttgtgg ggcgatgaat attcgtatga   1020

caaaataaga agggaaaaaa taggttgtga attaaggaaa gtgtaggcca ttattagtac   1080

tctatca                                                             1087
```

<210> SEQ ID NO 26
<211> LENGTH: 1087
<212> TYPE: DNA
<213> ORGANISM: S. lycopersicum

<400> SEQUENCE: 26

```
atgtggtcat caagcagtga taacagggga ctctctgctt cttcttcttc atcttcatcc     60

tcatctcatt caccattttc tccaagactc aaaacaatgg aagaagtgtg gaaagatatt    120

aatctttctt cacttcaaga tcacactacg aattactcta gagatcatca tcatcttcat    180
```

-continued

```
gatcataatc atcaagctgc taattttggt ggaatgattt tacaagattt tttggcaagg    240
ccttttgcta atgaatcttc accagcagca gcagcagcag cagcctcccc tgtttcagct    300
acaactatgc tgaatttgaa ctctgttcct gagcttcatt tctttgataa cccattgagg    360
caaaactcaa tcttgcacca accaaatgca agtggaagaa aaagggttgt ccctgaaaca    420
gaagacaatt ctacagggga tagaagaaat cagaggatga tcaagaacag agagtctgct    480
gctagatcaa gagctagaaa gcaggtaagt gacactcaac tttgtcttaa tcctgtcaat    540
tttgtgctta tacatcaact atgttccata ttgttactct tttgctgctt ctattcttga    600
tttgaacaat atgccgagtt actctgtttg caggcttata tgaacgagtt ggaatcagaa    660
gtggcacatt tagttgaaga aaatgcaagg ctcaagaagc agcagcaaca ggttctctta    720
tctttcttta tttctgtcac ttttaaaatt cagtttataa aaaaaatgga tataactgat    780
tcataataaa ttggtgtttt cttaatttgt acagttacga gtagatgcag ctaatcaagt    840
tcccaaaaag aacactcttt atcggacgtc aattgctcca ttttgagatc ttattataat    900
ttggtttcct agtgctacat tagtattaag aacaatttcc catttggctg tattttgttt    960
gtaatatgca ccaactgttg ttttgatggt ggccttgtgg ggcgatgaat attcgtatga   1020
caaaataaga agggaaaaaa taggttgtga attaaggaaa gtgtaggcca ttattagtac   1080
tctatca                                                             1087
```